United States Patent
Forgie et al.

(10) Patent No.: US 9,248,189 B2
(45) Date of Patent: Feb. 2, 2016

(54) ANTI-GLUCAGON RECEPTOR ANTIBODIES AND PHARMACEUTICAL COMPOSITIONS THEREOF

(71) Applicant: RINAT NEUROSCIENCE CORP., South San Francisco, CA (US)

(72) Inventors: Alison Jane Forgie, Redwood City, CA (US); Javier Fernando Chaparro Riggers, San Mateo, CA (US); Edward Roland Lavallie, Harvard, MA (US); Chia-Yang Lin, Palo Alto, CA (US); Lidia Mosyak, Newton, MA (US); Andrea Rossi, San Francisco, CA (US); Thomas John Van Blarcom, Oakland, CA (US)

(73) Assignee: PFIZER INC., New York, NY (US)

( * ) Notice: Subject to any disclaimer, the term of this patent is extended or adjusted under 35 U.S.C. 154(b) by 0 days.

(21) Appl. No.: 14/268,933

(22) Filed: May 2, 2014

(65) Prior Publication Data
US 2014/0335091 A1  Nov. 13, 2014

Related U.S. Application Data

(60) Provisional application No. 61/820,604, filed on May 7, 2013, provisional application No. 61/981,115, filed on Apr. 17, 2014.

(51) Int. Cl.

| | |
|---|---|
| *A61K 45/06* | (2006.01) |
| *A61K 31/155* | (2006.01) |
| *A61K 39/395* | (2006.01) |
| *C07K 16/28* | (2006.01) |
| *A61K 39/00* | (2006.01) |

(52) U.S. Cl.
CPC .............. *A61K 45/06* (2013.01); *A61K 31/155* (2013.01); *A61K 39/39541* (2013.01); *C07K 16/2869* (2013.01); *A61K 2039/505* (2013.01); *C07K 2317/33* (2013.01); *C07K 2317/55* (2013.01); *C07K 2317/76* (2013.01); *C07K 2317/92* (2013.01)

(58) Field of Classification Search
CPC ........... A61K 31/155; A61K 39/39541; A61K 45/06; A61K 2039/505; A61K 2300/00; C07K 16/2869; C07K 2317/33; C07K 2317/55; C07K 2317/76; C07K 2317/92
See application file for complete search history.

(56) References Cited

U.S. PATENT DOCUMENTS 5,770,445 A   6/1998  Kindsvogel et al.
8,545,847 B2  10/2013  Okamoto et al.

FOREIGN PATENT DOCUMENTS

| WO | 2008036341 A2 | 3/2008 |
| WO | 2009120530 A1 | 10/2009 |
| WO | 2011030935 A1 | 3/2011 |

OTHER PUBLICATIONS

Paul, WE. Fundamental Immunology, 3rd ed. Raven Press, NY, Chap. 9, pp. 292-295, 1993.*
Buggy, J., et al., "Human Glucagon Receptor Monoclonal Antibodies: Antagonism of Glucagon Action and Use in Receptor Characterization," Hormone and Metabolic Research, 1996, 215-219, vol. 28, No. 5.
Casadevall, A., et al., "Immunoglobulin Isotype Influences Affinity and Specificity," PNAS, 2012, 12272-12273, vol. 109, No. 31.
Gelling, R., et al., "Lower Blood Glucose, Hyperglucagonemia, and Pancreatic α Cell Hyperplasia in Glucagon Receptor Knockout Mice," PNAS, 2003, 1438-1443, vol. 100, No. 3.
Gu, W., et al., "Long-Term Inhibition of the Glucagon Receptor with a Monoclonal Antibody in Mice Causes Sustained Improvement in Glycemic Control, with Reversible α-Cell Hyperplasia and Hyperglucagonemia," The Journal of Pharmacology and Experimental Therapeutics, 2009, 871-881, vol. 331, No. 3.
International Search Report for International Application No. PCT/IB2014/061166 completed on Aug. 1, 2014.
Kim, W., et al., "Human Monoclonal Antibodies against Glucagon Receptor Improve Glucose Homeostasis by Suppression of Hepatic Glucose Output in Diet-Induced Obese Mice," PLOS One, 2012, e50954, vol. 7, No. 12.
Koth, C., et al., "Molecular Basis for Negative Regulation of the Glucagon Receptor," PNAS, 2012, 14393-14398, vol. 109, No. 36.
MacNeil, D., et al., "Cloning and Expression of a Human Glucagon Receptor," Biochemical and Biophysical Research Communications, 1994, 328-334, vol. 198, No. 1.
Moller, "New Drug Targets for Type 2 Diabetes and the Metabolic Syndrome," Nature, 2001, 821-827, vol. 414.
Rudikoff, S., et al., "Single Amino Acid Substitution Altering Antigen-Binding Specificity," PNAS, 1982, 1979-1983, vol. 79.
Unson, C. et al., "Antibodies against Specific Extracellular Epitopes of the Glucagon Receptor Block Glucagon Binding," PNAS, 1996, 310-315, vol. 93, No. 1.
Unson, C., et al., "Roles of Specific Extracellular Domains of the Glucagon Receptor in Ligand Binding and Signaling," Biochemistry, 2002, 11795-11803, vol. 41., No. 39.
Wright, L., et al., "Structure of Fab hGR-2 F6, a Competitive Antagonist of the Glucagon Receptor," Acta Crystallographica Section D Biological Crystallography, 2000, 573-580, vol. 56, No. 5.

(Continued)

Primary Examiner — Robert Landsman

(57) ABSTRACT

The present invention provides antagonizing antibodies that bind to glucagon receptor and methods of using same. The anti-glucagon receptor antibodies can be used therapeutically to lower glucose levels in blood, and can be in the prevention and/or treatment of glucose-related disorders, including diabetes, hyperglycemia, hyperinsulinemia, impaired fasting glucose, impaired glucose tolerance, dyslipidemia, or metabolic syndrome.

14 Claims, 5 Drawing Sheets

(56) References Cited

OTHER PUBLICATIONS

Figure 1:
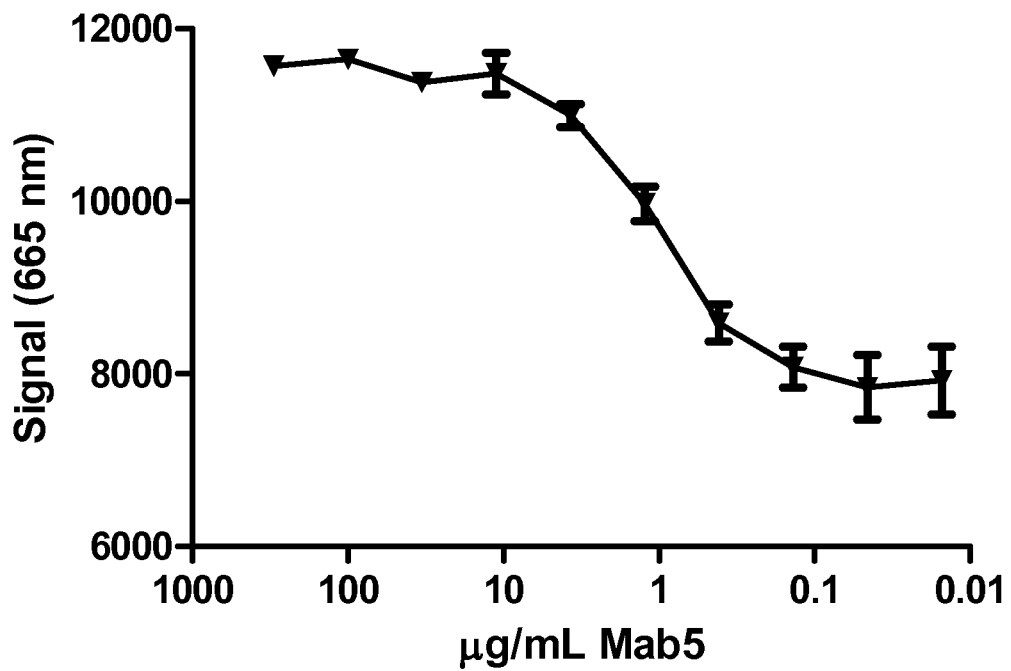

Written Opinion for International Application No. PCT/IB2014/061166 completed on Aug. 1, 2014.

Yan, H., et al., "Fully Human Monoclonal Antibodies Antagonizing the Glucagon Receptor Improve Glucose Homeostasis in Mice and Monkeys," The Journal of Pharmacology and Experimental Therapeutics, 2009, 102-111, vol. 329, No. 1.

Yu, R., et al., "Nesidioblastosis and Hyperplasia of α Cells, Microglucagonoma, and Nonfunctioning Islet Cell Tumor of the Pancreas," Pancreas, 2008, 428-431, vol. 36, No. 4.

Yu, R., et al., "Pancreatic Neuroendocrine Tumors in Glucagon Receptor-Deficient Mice," PLOS One, 2011, e23397, vol. 6, No. 8.

* cited by examiner

A

B

ANTI-GLUCAGON RECEPTOR ANTIBODIES AND PHARMACEUTICAL COMPOSITIONS THEREOF

This application claims priority, under 35 USC §119(e), to U.S. Provisional Application Ser. No. 61/820,604, filed May 7, 2013, and U.S. Provisional Application Ser. No. 61/981,115, filed Apr. 17, 2014, hereby incorporated by reference in their entireties.

REFERENCE TO SEQUENCE LISTING

This application is being filed electronically via EFS-Web and includes an electronically submitted sequence listing in .txt format. The .txt file contains a sequence listing entitled "SequenceListing_PC33992A" created on May 1, 2014 and having a size of 72 KB. The sequence listing contained in this .txt file is part of the specification and is herein incorporated by reference in its entirety.

FIELD

The present invention relates to antibodies, e.g., full length antibodies that bind glucagon receptor. The invention further relates to compositions comprising antibodies to glucagon receptor, and methods of using anti-glucagon receptor antibodies as a medicament. The anti-glucagon receptor antibodies can be used therapeutically to lower glucose levels in blood, and can be in the prevention and/or treatment of glucose-related disorders, including diabetes.

BACKGROUND

Diabetes is a major public health concern because of its increasing prevalence and associated health risks. The disease is characterized by metabolic defects in the production and utilization of carbohydrates which result in the failure to maintain appropriate plasma glucose levels. Two major forms of diabetes are recognized. Type I diabetes (T1D), or insulin-dependent diabetes mellitus, is the result of an absolute deficiency of insulin. Type II diabetes (T2D), or non-insulin dependent diabetes mellitus, often occurs with normal, or even elevated levels of insulin and appears to be the result of the inability of tissues and cells to respond appropriately to insulin. Aggressive control of T2D with medication is essential; otherwise it can progress into β-cell failure and insulin dependence.

Glucagon is a twenty-nine amino acid peptide which is secreted from the acells of the pancreas into the hepatic portal vein thereby exposing the liver to higher levels of this hormone than non-hepatic tissues. Plasma glucagon levels decrease in response to hyperglycemia, hyperinsulinemia, elevated plasma non-esterified fatty acid levels and somatostatin whereas glucagon secretion is increased in response to hypoglycemia and elevated plasma amino acid levels. Glucagon, through activation of its receptor, is a potent activator of hepatic glucose production by activating glycogenolysis and gluconeogenesis. In T2D individuals, basal glucagon levels are high and inadequately suppressed by hyperglycemia and hyperinsulinemia.

The glucagon receptor is a 62 kDa protein that is activated by glucagon and is a member of the class B G-protein coupled family of receptors. The glucagon receptor is encoded by the GCGR gene in humans and these receptors are mainly expressed in the liver with lesser amounts found in the kidney, heart, adipose tissue, spleen, thymus, adrenal glands, pancreas, cerebral cortex and gastrointestinal tract. Stimulation of the glucagon receptor results in activation of adenylate cyclase and increased levels of intracellular cAMP.

Genetic disruption of glucagon receptor expression in mice (Gcgr−/−) lowers fasting and fed glucose levels and improves glycemic control. However, the Gcgr−/− mice develop hyperglucagonemia, pancreatic a cell hyperplasia, and pancreatic neuroendocrine tumors (Gelling, R. W. et al., 2003, "Lower plasma glucose, hyperglucagonemia, and pancreatic alpha cell hyperplasia in glucagon receptor knockout mice" *Proc. Natl. Acad. Sci. U.S.A.* 100: 1438-1443; Yu, R. et al., 2011, "Pancreatic neuroendocrine tumors in glucagon receptor-deficient mice" *Plos ONE* 6(8): e23397). Similarly, a human patient born with a homozygous inactivating GCGR mutation (P86S) develops pancreatic neuroendocrine tumors and exhibits hyperglucagonemia and pancreatic a cell hyperplasia (Yu, R. et al., 2008, "Nesidioblastosis and hyperplasia of alpha cells, microglucagonoma, and nonfunctioning islet cell tumor of the pancreas" *Pancreas* 36: 428-431).

Several drugs in five major categories, each acting by different mechanisms, are available for treating hyperglycemia and subsequently, T2D (Moller, D. E., 2011, "New drug targets for Type 2 diabetes and the metabolic syndrome" *Nature* 414: 821-827): (A) Insulin secretogogues, including sulphonyl-ureas (e.g., glipizide, glimepiride, glyburide) and meglitinides (e.g., nateglidine and repaglinide) enhance secretion of insulin by acting on the pancreatic beta-cells. While this therapy can decrease plasma glucose level, it has limited efficacy and tolerability, causes weight gain and often induces hypoglycemia. (B) Biguanides (e.g., metformin) are thought to act primarily by decreasing hepatic glucose production. Biguanides often cause gastrointestinal disturbances and lactic acidosis, further limiting their use. (C) Inhibitors of alpha-glucosidase (e.g., acarbose) decrease intestinal glucose absorption. These agents often cause gastrointestinal disturbances. (D) Thiazolidinediones (e.g., pioglitazone, rosiglitazone) act on a specific receptor (peroxisome proliferator-activated receptor-gamma) in the liver, muscle and fat tissues. They regulate lipid metabolism subsequently enhancing the response of these tissues to the actions of insulin. Frequent use of these drugs may lead to weight gain and may induce edema and anemia. (E) Insulin is used in more severe cases, either alone or in combination with the above agents.

From the information available in the art, and prior to the present invention, it remained unclear whether the introduction of anti-glucagon receptor antagonist antibody into the blood circulation to selectively antagonize glucagon receptor would be safe and effective to lower plasma glucose levels and prevent and/or treat diabetes, and, if so, what properties of an anti-glucagon receptor antibody are needed for such in vivo safety and effectiveness.

SUMMARY

Antibodies that selectively interact with glucagon receptor are provided. It is demonstrated that certain anti-glucagon receptor antibodies are effective in vivo to prevent and/or treat diabetes. Advantageously, the anti-glucagon receptor antibodies provided herein do not adversely affect liver function or plasma lipids. Also advantageously, the anti-glucagon receptor antibodies provided herein are effective in vivo to reduce C-peptide levels in blood.

Isolated antagonist antibodies that specifically bind to glucagon receptor and prevent or reduce the biological effect of glucagon receptor are provided herein. In some embodiments, the antagonist antibody can be, for example, a human, humanized, or chimeric antibody.

In some embodiments, the isolated antagonist antibody may comprise, for example, a heavy chain variable region (VH) comprising a VH complementarity determining region one (CDR1), VH CDR2, and VH CDR3 of the VH having the amino acid sequence shown in SEQ ID NO: 3, 5, 7, 9 or 11; and/or a light chain variable region (VL) comprising a VL CDR1, VL CDR2, and VL CDR3 of the VL having the amino acid sequence shown in SEQ ID NO: 2, 4, 6, 8 or 10. Each CDR of the antibody can be defined in accordance with, for example, the Kabat definition, the Chothia definition, the combination of the Kabat definition and the Chothia definition, the AbM definition, and/or the contact definition of CDR.

In some embodiments, the antibody may comprise, for example, a heavy chain variable region (VH) selected group the group consisting of: (a) a VH comprising a VH complementarity determining region one (CDR1), VH CDR2, and VH CDR3 of the VH having the amino acid sequence shown in SEQ ID NO: 3; (b) a VH comprising a VH CDR1, VH CDR2, and VH CDR3 of the VH having the amino acid sequence shown in SEQ ID NO: 5; (c) a VH comprising a VH CDR1, VH CDR2, and VH CDR3 of the VH having the amino acid sequence shown in SEQ ID NO: 7; (d) a VH comprising a VH CDR1, VH CDR2, and VH CDR3 of the VH having the amino acid sequence shown in SEQ ID NO: 9; and (e) a VH comprising a VH CDR1, VH CDR2, and VH CDR3 of the VH having the amino acid sequence shown in SEQ ID NO: 11; and a light chain variable region (VL) selected from the group consisting of: (f) a VL comprising a VL CDR1, VL CDR2, and VL CDR3 of the VL having the amino acid sequence shown in SEQ ID NO: 2; (g) a VL comprising a VL CDR1, VL CDR2, and VL CDR3 of the VH having the amino acid sequence shown in SEQ ID NO: 4; (h) a VL comprising a VL CDR1, VL CDR2, and VL CDR3 of the VH having the amino acid sequence shown in SEQ ID NO: 6; (i) a VL comprising a VL CDR1, VL CDR2, and VL CDR3 of the VH having the amino acid sequence shown in SEQ ID NO: 8; and (j) a VL comprising a VL CDR1, VL CDR2, and VL CDR3 of the VH having the amino acid sequence shown in SEQ ID NO: 10.

In some embodiments, the antibody may comprise, for example, a VH CDR1 comprising the amino acid sequence of SEQ ID NO: 24, 16 or 25, a VH CDR2 comprising the amino acid sequence of SEQ ID NO: 18 or 26, a VH CDR3 comprising the amino acid sequence shown in SEQ ID NO: 41, a VL CDR1 comprising the amino acid sequence shown in SEQ ID NO: 40, a VL CDR2 comprising the amino acid sequence shown in SEQ ID NO: 13, and/or a VL CDR3 comprising the amino acid sequence shown in SEQ ID NO: 14.

In some embodiments, the antibody may comprise, for example, a VH comprising the amino acid sequence shown in SEQ ID NO: 3, 5, 7, 9 or 11 or a variant thereof with one or several conservative amino acid substitutions in residues that are not within a CDR. In some embodiments, the antibody may comprise, for example, a VL comprising the amino acid sequence shown in SEQ ID NO: 2, 4, 6, 8 or 10 or a variant thereof with one or several amino acid substitutions in amino acids that are not within a CDR.

In some embodiments, the antibody may comprise, for example, a VH comprising the amino acid sequence shown in SEQ ID NO: 11 and/or a VL comprising the amino acid sequence shown in SEQ ID NO: 10. In some embodiments, the antibody may comprise, for example, a heavy chain comprising the amino acid sequence shown in SEQ ID NO: 87 or 88 and/or a light chain comprising the amino acid sequence shown in SEQ ID NO: 89.

In some embodiments, the antibody may comprise an immunologically inert constant region. In some embodiments, the constant region may be, for example, aglycosylated Fc. In some embodiments, the antibody may comprise an isotype that is selected from the group consisting of IgG$_2$, IgG$_{2\Delta a}$, IgG$_4$, IgG$_{4\Delta b}$, IgG$_{4\Delta c}$, IgG$_4$ S228P, IgG$_{4\Delta b}$ S228P and IgG$_{4\Delta c}$ S228P.

Also provided herein are isolated anti-glucagon receptor antagonist antibodies that specifically bind to an epitope that is the same as or overlaps with the epitope on glucagon receptor recognized by the monoclonal antibody mAb1, mAb2, mAb3, mAb4 or mAb5. In some embodiments, the antibody may comprise a VH CDR1 comprising the amino acid sequence of SEQ ID NO: 17, a VH CDR2 comprising the amino acid sequence of SEQ ID NO: 93, a VH CDR3 comprising the amino acid sequence shown in SEQ ID NO: 94, a VL CDR1 comprising the amino acid sequence shown in SEQ ID NO: 90, a VL CDR2 comprising the amino acid sequence shown in SEQ ID NO: 91, and/or a VL CDR3 comprising the amino acid sequence shown in SEQ ID NO: 92. In some embodiments, the epitope is a structural epitope. In some embodiments, the epitope comprises amino acid residues 31, 33-38, 40-42, 44-45, 48, 62, and 64 of the glucagon receptor amino acid sequence shown in SEQ ID NO: 1. In some embodiments, the epitope is a functional epitope. In some embodiments, the functional epitope comprises amino acid residues 33, 36, 38, 41, 44 and 45 of the glucagon receptor amino acid sequence shown in SEQ ID NO: 1. In some embodiments, the functional epitope comprises amino acid residues 33, 36, 38, 41, 44, 45 and 60 of the glucagon receptor amino acid sequence shown in SEQ ID NO: 1.

Also provided are cell lines that produce one or more antibodies provided herein.

Also provided are isolated nucleic acids encoding the antibodies provided herein. In some embodiments the isolated nucleic acids can be operably linked to a control sequence. In some embodiments, the isolated nucleic acids can comprise a polynucleotide sequence encoding the light chain variable domain, the heavy chain variable domain, or both, of an antibody provided herein.

Also provided are recombinant expression vectors comprising nucleic acids provided herein. Also provided are host cells comprising any of the expression vectors provided herein. Also provided are hybridomas capable of producing any of the antibodies provided herein.

Also provided are methods of producing an anti-glucagon receptor antagonist antibody provided herein. In some embodiments, the method comprises: culturing a cell line that produces the antibody under conditions wherein the antibody is produced; and recovering the antibody. In some embodiments, the method comprises: culturing a cell line comprising nucleic acid encodihyrng an antibody comprising a heavy chain comprising the amino acid sequence shown in SEQ ID NO: 87 or 88 and a light chain comprising the amino acid sequence shown in SEQ ID NO: 89 under conditions wherein the antibody is produced; and recovering the antibody. In some embodiments, the heavy and light chains are encoded on separate vectors. In other embodiments, the heavy and light chains are encoded on the same vector.

Also provided are pharmaceutical compositions comprising one or more antibodies provided herein, and a pharmaceutically acceptable carrier. Also provided are kits for the treatment of a condition mediated by glucagon receptor comprising a pharmaceutical composition comprising one or more antibodies provided herein.

Also provided are methods for lowering blood glucose, improving glucose tolerance, lowering C-peptide levels, preventing significant increase in blood levels of C-peptide, and/or treating or preventing a condition mediated by glucagon receptor in an individual in need thereof. In some embodiments, the method comprises administering to the individual an effective amount of an anti-glucagon receptor antagonist antibody provided herein, such that a blood glucose level is lowered, glucose tolerance is improved, and/or one or more symptoms associated with the condition is ameliorated in the individual. In other embodiments, the method comprises administering to the individual an effective amount of an anti-glucagon receptor antagonist antibody provided herein, such that a C-peptide level is lowered in the individual. In other embodiments, the method comprises administering to the individual an effective amount of an anti-glucagon receptor antagonist antibody provided herein, and an mTor inhibitor, such that a blood glucose level is lowered, glucose tolerance is improved, and/or one or more symptoms associated with the condition is ameliorated in the individual. The individual can be, for example without limitation, a mammal. In some embodiments, the individual is a human. In some embodiments, the anti-glucagon receptor antagonist antibody reduces weight gain in the individual.

In some embodiments, the condition is, for example, type 1 diabetes, type 2 diabetes, hyperglycemia, hyperinsulinemia, impaired fasting glucose, impaired glucose tolerance, dyslipidemia, diabetic ketoacidosis, long-term complications associated with diabetes, metabolic syndrome, or other metabolic disorders characterized in part by elevated blood glucose levels.

In some embodiments, changes in the alpha cells of the pancreatic islets after anti-glucagon receptor antagonist antibody treatment are reversed after levels of anti-glucagon receptor antagonist antibody in the individual fall below a minimally efficacious threshold level.

In some embodiments, changes in glycogen accumulation in hepatocytes after anti-glucagon receptor antagonist antibody treatment are reversed after levels of anti-glucagon receptor antagonist antibody in the individual fall below a minimally efficacious threshold level.

In some embodiments, the method can further comprise administering an effective amount of a second therapeutic agent. In some embodiments, the second therapeutic agent is, for example, insulin, an mTor inhibitor, a biguanide, a sulfonylurea, a PPAR gamma agonist, an alpha glucosidase inhibitor, EXENATIDE®, SYMLIN®, a glucagon antagonist, or a second glucagon receptor antagonist. In some embodiments, the biguanide is, for example, metformin. In some embodiments, mTor inhibitor is, for example, rapamycin, sirolimus, temsirolimus, everolimus, ridaforolimus, or an ATP-competitive mTOR kinase inhibitor (TKI). In some embodiments, the TKI is, for example, Torin1, Torin 2, PP242, PP30, KU0063794, WAY-600, WYE-687, WYE-354, OSI-027, AZD-8055, KU-BMCL-200908069-1, Wyeth-BMCL-200908069-2, XL-388, INK-128, and AZD-2014. In some embodiments, combination treatment with an mTOR inhibitor reduces hypertrophy and/or hyperplasia elicited by blocking glucagon receptor activity.

Also provided is the use of any of the anti-glucagon receptor antagonist antibodies provided herein in the manufacture of a medicament for the treatment or prevention of type 1 or type 2 diabetes or for achieving weight loss in a human. In some embodiments, the anti-glucagon receptor antagonist antibody reduces weight gain in the individual.

Also provided are anti-glucagon receptor antagonist antibodies for use in the treatment of a condition mediated by glucagon receptor. In some embodiments, the condition is, for example, type 1 diabetes, type 2 diabetes, hyperglycemia, hyperinsulinemia, impaired fasting glucose, impaired glucose tolerance, dyslipidemia, or metabolic syndrome.

BRIEF DESCRIPTION OF THE FIGURES/DRAWINGS

FIG. 1 depicts a graph summarizing results of a cAMP assay.

FIGS. 2A-B. Figure A depicts a graph summarizing the results of an alanine aminotransferase (ALT) test in animals administered either anti-glucagon receptor antagonist antibody mAb5 (open circles) or PBS (closed circles). Figure B depicts a graph summarizing the results of an aspartate aminotransferase (AST) test in animals administered either mAb5 (open circles) or PBS (closed circles).

FIGS. 3A-B. Figure A depicts a graph summarizing the results of an alkaline phosphatase (ALP) test in animals administered either mAb5 (open circles) or PBS (closed circles). Figure B depicts a graph summarizing the results of agamma-glutamyltransferase (GGT) test in animals administered either mAb5 (open circles) or PBS (closed circles).

FIGS. 4A-B. Figure A depicts a graph summarizing the total cholesterol levels in animals administered either mAb5 (open circles) or PBS (closed circles). Figure B depicts a graph summarizing the LDL-C levels in animals administered either mAb5 (open circles) or PBS (closed circles).

FIGS. 5A-B. Figure A depicts a graph summarizing the HDL-C levels in animals administered either mAb5 (open circles) or PBS (closed circles). Figure B depicts a graph summarizing the triglyceride levels in animals administered either mAb5 (open circles) or PBS (closed circles).

DETAILED DESCRIPTION

Disclosed herein are antibodies that specifically bind to glucagon receptor. Methods of making anti-glucagon receptor antibodies, compositions comprising these antibodies, and methods of using these antibodies as a medicament are provided. Anti-glucagon receptor antibodies can be used to lower plasma glucose levels, and can be used in the prevention and/or treatment of T1D, T2D or related disorders including hyperglycemia, impaired fasting glucose, impaired glucose tolerance, dyslipidemia, obesity, nephropathy, retinopathy, cataracts, stroke, atherosclerosis, impaired wound healing, diabetic ketoacidosis, hyperglycemic hyperosmolar syndrome, perioperative hyperglycemia, hyperglycemia in the intensive care unit patient, insulin resistance syndrome, and metabolic syndrome.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

DEFINITIONS

The following terms, unless otherwise indicated, shall be understood to have the following meanings: the term "isolated molecule" as referring to a molecule (where the molecule is, for example, a polypeptide, a polynucleotide, or an antibody) that by virtue of its origin or source of derivation (1) is not associated with naturally associated components that accompany it in its native state, (2) is substantially free of other molecules from the same source, e.g., species, cell from which it is expressed, library, etc., (3) is expressed by a cell from a different species, or (4) does not occur in nature. Thus, a molecule that is chemically synthesized, or expressed in a cellular system different from the system from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also, unless otherwise specified, any antigen binding portion thereof that competes with the intact antibody for specific binding, fusion proteins comprising an antigen binding portion, and any other modified configuration of the immunoglobulin molecule that comprises an antigen recognition site. Antigen binding portions include, for example, Fab, Fab', F(ab')$_2$, Fd, Fv, domain antibodies (dAbs, e.g., shark and camelid antibodies), fragments including complementarity determining regions (CDRs), single chain variable fragment antibodies (scFv), maxibodies, minibodies, intrabodies, diabodies, triabodies, tetrabodies, v-NAR and bis-scFv, and polypeptides that contain at least a portion of an immunoglobulin that is sufficient to confer specific antigen binding to the polypeptide. An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG$_1$, IgG$_2$, IgG$_3$, IgG$_4$, IgA$_1$ and IgA$_2$. The heavy-chain constant regions that correspond to the different classes of immunoglobulins are called alpha, delta, epsilon, gamma, and mu, respectively. The subunit structures and three-dimensional configurations of different classes of immunoglobulins are well known.

A "variable region" of an antibody refers to the variable region of the antibody light chain or the variable region of the antibody heavy chain, either alone or in combination. As known in the art, the variable regions of the heavy and light chains each consist of four framework regions (FRs) connected by three complementarity determining regions (CDRs) also known as hypervariable regions, and contribute to the formation of the antigen binding site of antibodies. If variants of a subject variable region are desired, particularly with substitution in amino acid residues outside of a CDR region (i.e., in the framework region), appropriate amino acid substitution, preferably, conservative amino acid substitution, can be identified by comparing the subject variable region to the variable regions of other antibodies which contain CDR1 and CDR2 sequences in the same canonincal class as the subject variable region (Chothia and Lesk, J Mol Biol 196(4): 901-917, 1987).

In certain embodiments, definitive delineation of a CDR and identification of residues comprising the binding site of an antibody is accomplished by solving the structure of the antibody and/or solving the structure of the antibody-ligand complex. In certain embodiments, that can be accomplished by any of a variety of techniques known to those skilled in the art, such as X-ray crystallography. In certain embodiments, various methods of analysis can be employed to identify or approximate the CDR regions. In certain embodiments, various methods of analysis can be employed to identify or approximate the CDR regions. Examples of such methods include, but are not limited to, the Kabat definition, the Chothia definition, the AbM definition, the contact definition, and the conformational definition.

The Kabat definition is a standard for numbering the residues in an antibody and is typically used to identify CDR regions. See, e.g., Johnson & Wu, 2000, Nucleic Acids Res., 28: 214-8. The Chothia definition is similar to the Kabat definition, but the Chothia definition takes into account positions of certain structural loop regions. See, e.g., Chothia et al., 1986, J. Mol. Biol., 196: 901-17; Chothia et al., 1989, Nature, 342: 877-83. The AbM definition uses an integrated suite of computer programs produced by Oxford Molecular Group that model antibody structure. See, e.g., Martin et al., 1989, Proc Natl Acad Sci (USA), 86:9268-9272; "AbM™, A Computer Program for Modeling Variable Regions of Antibodies," Oxford, UK; Oxford Molecular, Ltd. The AbM definition models the tertiary structure of an antibody from primary sequence using a combination of knowledge databases and ab initio methods, such as those described by Samudrala et al., 1999, "Ab Initio Protein Structure Prediction Using a Combined Hierarchical Approach," in PROTEINS, Structure, Function and Genetics Suppl., 3:194-198. The contact definition is based on an analysis of the available complex crystal structures. See, e.g., MacCallum et al., 1996, J. Mol. Biol., 5:732-45. In another approach, referred to herein as the "conformational definition" of CDRs, the positions of the CDRs may be identified as the residues that make enthalpic contributions to antigen binding. See, e.g., Makabe et al., 2008, Journal of Biological Chemistry, 283:1156-1166. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions.

As known in the art, a "constant region" of an antibody refers to the constant region of the antibody light chain or the constant region of the antibody heavy chain, either alone or in combination.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, 1975, Nature 256:495, or may be made by recombinant DNA methods such as described in U.S. Pat. No. 4,816,567. The monoclonal antibodies may also be isolated from phage libraries generated using the techniques described in McCafferty et al., 1990, Nature 348:552-554, for example. As used herein, "humanized" antibody refers to forms of non-human (e.g. murine) antibodies that are chimeric immunoglobulins, immunoglobulin chains, or fragments thereof (such as Fv, Fab, Fab', F(ab')$_2$ or other antigen-binding subsequences of antibodies) that contain minimal sequence derived from non-human immunoglobulin. Preferably, humanized antibodies are human immunoglobulins (recipient antibody) in which residues from a CDR of the recipient are replaced by residues from a CDR of a non-human species (donor antibody) such as mouse, rat, or rabbit having the desired specificity, affinity, and capacity. The humanized antibody may comprise residues that are found neither in the recipient antibody nor in the imported CDR or framework sequences, but are included to further refine and optimize antibody performance.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen binding residues.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

The term "epitope" refers to that portion of a molecule capable of being recognized by and bound by an antibody at one or more of the antibody's antigen-binding regions. Epitopes often consist of a surface grouping of molecules such as amino acids or sugar side chains and have specific three-dimensional structural characteristics as well as specific charge characteristics. In some embodiments, the epitope can be a protein epitope. Protein epitopes can be linear or conformational. In a linear epitope, all of the points of interaction between the protein and the interacting molecule (such as an antibody) occur linearly along the primary amino acid sequence of the protein. A "nonlinear epitope" or "conformational epitope" comprises noncontiguous polypeptides (or amino acids) within the antigenic protein to which an antibody specific to the epitope binds. The term "antigenic epitope" as used herein, is defined as a portion of an antigen to which an antibody can specifically bind as determined by any method well known in the art, for example, by conventional immunoassays. Once a desired epitope on an antigen is determined, it is possible to generate antibodies to that epitope, e.g., using the techniques described in the present specification. Alternatively, during the discovery process, the generation and characterization of antibodies may elucidate information about desirable epitopes. From this information, it is then possible to competitively screen antibodies for binding to the same epitope. An approach to achieve this is to conduct competition and cross-competition studies to find antibodies that compete or cross-compete with one another for binding to glucagon receptor, e.g., the antibodies compete for binding to the antigen. A "functional epitope" comprises As used herein, the term "glucagon receptor" refers to any form of glucagon receptor and variants thereof that retain at least part of the activity of glucagon receptor. Unless indicated differently, such as by specific reference to human glucagon receptor, glucagon receptor includes all mammalian species of native sequence glucagon receptor, e.g., human, canine, feline, equine, and bovine. One exemplary human glucagon receptor is found as Uniprot Accession Number P47871 (SEQ ID NO: 1).

The term "antagonist antibody" refers to an antibody that binds to a target and prevents or reduces the biological effect of that target. In some embodiments, the term can denote an antibody that prevents the target, e.g., glucagon receptor, to which it is bound from performing a biological function.

As used herein, an "anti-glucagon receptor antagonist antibody" refers to an antibody that is able to inhibit glucagon receptor biological activity and/or downstream events(s) mediated by glucagon receptor. Anti-glucagon receptor antagonist antibodies encompass antibodies that block, antagonize, suppress or reduce (to any degree including significantly) glucagon receptor biological activity, including downstream events mediated by glucagon receptor, such glucagon binding and downstream signaling, adenylate cyclase activation, increased levels of intracellular cAMP, glycogenolysis stimulation, gluconeogenesis activation, glycogenesis inhibition, glycolysis inhibition, and hepatic glucose production. For purposes of the present invention, it will be explicitly understood that the term "anti-glucagon receptor antagonist antibody" (interchangeably termed "antagonist glucagon receptor antibody", "antagonist anti-glucagon receptor antibody" or "glucagon receptor antagonist antibody") encompasses all the previously identified terms, titles, and functional states and characteristics whereby the glucagon receptor itself, a glucagon receptor biological activity (including but not limited to its ability to bind glucagon, increase intracellular cAMP, stimulate glycogenolysis, activate gluconeogenesis, and promote relase of hepatic glucose), or the consequences of the biological activity, are substantially nullified, decreased, or neutralized in any meaningful degree. In some embodiments, an anti-glucagon receptor antagonist antibody binds glucagon receptor and lowers plasma glucose levels. Examples of anti-glucagon receptor antagonist antibodies are provided herein.

The terms "polypeptide", "oligopeptide", "peptide" and "protein" are used interchangeably herein to refer to chains of amino acids of any length. The chain may be linear or branched, it may comprise modified amino acids, and/or may be interrupted by non-amino acids. The terms also encompass an amino acid chain that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that the polypeptides can occur as single chains or associated chains.

As known in the art, "polynucleotide," or "nucleic acid," as used interchangeably herein, refer to chains of nucleotides of any length, and include DNA and RNA. The nucleotides can be deoxyribonucleotides, ribonucleotides, modified nucleotides or bases, and/or their analogs, or any substrate that can be incorporated into a chain by DNA or RNA polymerase. A polynucleotide may comprise modified nucleotides, such as methylated nucleotides and their analogs. If present, modification to the nucleotide structure may be imparted before or after assembly of the chain. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha- or beta-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or aralkyl. Not all linkages in a polynucleotide need be identical. The preceding description applies to all polynucleotides referred to herein, including RNA and DNA.

As used herein, an antibody "interacts with" glucagon receptor when the equilibrium dissociation constant is equal to or less than 20 nM, preferably less than about 6 nM, more preferably less than about 1 nM, most preferably less than about 0.2 nM, as measured by the methods disclosed herein in Example 1.

An antibody that "preferentially binds" or "specifically binds" (used interchangeably herein) to an epitope is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a glucagon receptor epitope is an antibody that binds this epitope with greater affinity, avidity, more readily, and/or with greater duration than it binds to other glucagon receptor epitopes or non-glucagon receptor epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

As used herein, "substantially pure" refers to material which is at least 50% pure (i.e., free from contaminants), more preferably, at least 90% pure, more preferably, at least 95% pure, yet more preferably, at least 98% pure, and most preferably, at least 99% pure.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As known in the art, the term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. Kabat et al., Sequences of Proteins of Immunological Interest, 5th Ed. Public Health Service, National Institutes of Health, Bethesda, Md., 1991. The Fc region of an immunoglobulin generally comprises two constant domains, CH2 and CH3. As is known in the art, an Fc region can be present in dimer or monomeric form.

As used in the art, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, 1991, Ann. Rev. Immunol., 9:457-92; Capel et al., 1994, Immunomethods, 4:25-34; and de Haas et al., 1995, J. Lab. Clin. Med., 126:330-41. "FcR" also includes the neonatal receptor, FcRn, which is responsible for the transfer of maternal IgGs to the fetus (Guyer et al., 1976, J. Immunol., 117:587; and Kim et al., 1994, J. Immunol., 24:249).

The term "compete", as used herein with regard to an antibody, means that a first antibody, or an antigen-binding portion thereof, binds to an epitope in a manner sufficiently similar to the binding of a second antibody, or an antigen-binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

A "functional Fc region" possesses at least one effector function of a native sequence Fc region. Exemplary "effector functions" include C1q binding; complement dependent cytotoxicity; Fc receptor binding; antibody-dependent cell-mediated cytotoxicity; phagocytosis; down-regulation of cell surface receptors (e.g. B cell receptor), etc. Such effector functions generally require the Fc region to be combined with a binding domain (e.g. an antibody variable domain) and can be assessed using various assays known in the art for evaluating such antibody effector functions.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification, yet retains at least one effector function of the native sequence Fc region. Preferably, the variant Fc region has at least one amino acid substitution compared to a native sequence Fc region or to the Fc region of a parent polypeptide, e.g. from about one to about ten amino acid substitutions, and preferably, from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably, at least about 90% sequence identity therewith, more preferably, at least about 95%, at least about 96%, at least about 97%, at least about 98%, at least about 99% sequence identity therewith.

As used herein, "treatment" is an approach for obtaining beneficial or desired clinical results. For purposes of this invention, beneficial or desired clinical results include, but are not limited to, one or more of the following: lowered blood glucose level, improved glucose clearance (improved glucose tolerance), and reduced incidence or amelioration of aberrant plasma glucose levels resulting from T1D, T2D, hyperglycemia, impaired fasting glucose, impaired glucose tolerance, dyslipidemia, obesity, nephropathy, retinopathy, cataracts, stroke, atherosclerosis, impaired wound healing, diabetic ketoacidosis, hyperglycemic hyperosmolar syndrome, perioperative hyperglycemia, hyperglycemia in the intensive care unit patient, insulin resistance syndrome, and metabolic syndrome.

"Ameliorating" means a lessening or improvement of one or more symptoms as compared to not administering an anti-glucagon receptor antagonist antibody. "Ameliorating" also includes shortening or reduction in duration of a symptom.

As used herein, an "effective dosage" or "effective amount" of drug, compound, or pharmaceutical composition is an amount sufficient to effect any one or more beneficial or desired results. In more specific aspects, an effective amount prevents, alleviates or ameliorates symptoms of disease, and/or prolongs the survival of the subject being treated. For prophylactic use, beneficial or desired results include eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include clinical results such as reducing one or more symptoms of T1D, T2D, hyperglycemia, hyperinsulinemia, impaired fasting glucose, impaired glucose tolerance, dyslipidemia, or metabolic syndrome, decreasing the dose of other medications required to treat the disease, enhancing the effect of another medication, and/or delaying the progression of the disease of patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

An "individual" or a "subject" is a mammal, more preferably, a human. Mammals also include, but are not limited to, farm animals (e.g., cows, pigs, horses, chickens, etc.), sport animals, pets, primates, horses, dogs, cats, mice and rats.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline (PBS) or normal (0.9%) saline. Compositions comprising such carriers are formulated by well known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000).

The term "$k_{on}$", as used herein, refers to the rate constant for association of an antibody to an antigen. Specifically, the rate constants ($k_{on}$ and $k_{off}$) and equilibrium dissociation constants are measured using full-length antibodies and/or Fab antibody fragments (i.e. univalent) and glucagon receptor.

The term "$k_{off}$", as used herein, refers to the rate constant for dissociation of an antibody from the antibody/antigen complex.

The term "$K_D$", as used herein, refers to the equilibrium dissociation constant of an antibody-antigen interaction.

Reference to "about" a value or parameter herein includes (and describes) embodiments that are directed to that value or parameter per se. For example, description referring to "about X" includes description of "X." Numeric ranges are inclusive of the numbers defining the range.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

Unless otherwise defined, all technical and scientific terms used herein have the same meaning as commonly understood by one of ordinary skill in the art to which this invention belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular. Any example(s) following the term "e.g." or "for example" is not meant to be exhaustive or limiting.

Exemplary methods and materials are described herein, although methods and materials similar or equivalent to those described herein can also be used in the practice or testing of the present invention. The materials, methods, and examples are illustrative only and not intended to be limiting.

Methods for Preventing or Treating Conditions Mediated by Glucagon Receptor

Provided herein is a method of lowering blood glucose in an individual in need thereof, the method comprising administering a therapeutically effective amount of an anti-glucagon receptor antagonist antibody to the individual.

Also provided is a method of improving glucose tolerance in an individual in need thereof, the method comprising administering a therapeutically effective amount of an anti-glucagon receptor antagonist antibody to the individual.

Also provided is a method for treating or preventing a condition mediated by glucagon receptor in an individual, the method comprising administering to an individual in need thereof an effective amount of an anti-glucagon receptor antagonist antibody. In some embodiments, the condition is T1D. In other embodiments, the condition is T2D. In other embodiments, the condition is hyperglycemia. In other embodiments, the condition is hyperinsulinemia. In other embodiments, the condition is impaired fasting glucose. In other embodiments, the condition is impaired glucose tolerance. In other embodiments, the condition is dyslipidemia. In other embodiments, the condition is metabolic syndrome.

In some embodiments, therapeutic administration of the anti-glucagon receptor antagonist antibody advantageously results in lower serum glucose. Preferably, serum glucose is at least about 10% or 15% lower than before administration. More preferably, serum glucose is at least about 20% lower than before administration of the antibody. Yet more preferably, serum glucose is at least 30% lower than before administration of the antibody. Advantageously, serum glucose is at least 40% lower than before administration of the antibody. More advantageously, serum glucose is at least 50% lower than before administration of the antibody. Very preferably, serum glucose is at least 60% lower than before administration of the antibody. Most preferably, serum glucose is at least 70% lower than before administration of the antibody.

An individual suffering from or at risk for T2D can be treated with an anti-glucagon receptor antagonist antibody. An individual suitable for anti-glucagon receptor antagonist antibody therapy is selected using clinical criteria and prognostic indicators of T2D that are well known in the art. Assessment of T2D severity may be performed based on tests known in the art, including, for example, fasting plasma glucose test, casual plasma glucose test, oral glucose tolerance test, two-hour postprandial test, random blood sugar, glycated hemoglobin (A1C) test, urine test, dilated eye exam, and foot exam. In some embodiments, ameliorating, controlling, reducing incidence of, or delaying the development or progression of T2D and/or symptoms of T2D is measured by fasting plasma glucose test.

In some embodiments, therapeutic administration of the anti-glucagon receptor antagonist antibody advantageously results in reduced incidence and/or amelioration of one or more symptoms of T2D including, for example, hyperglycemia, increased thirst, increased hunger, dry mouth, frequent urination, unexplained weight loss, fatigue, blurred vision, headaches, loss of consciousness, retinopathy, kidney damage, poor blood circulation, nerve damage, increased infections, ulcers, nausea, vomiting, and diarrhea.

An individual suffering from or at risk for T1D can be treated with an anti-glucagon receptor antagonist antibody. An individual suitable for anti-glucagon receptor antagonist antibody therapy is selected using clinical criteria and prognostic indicators of T1D that are well known in the art. Assessment of T1D severity may be performed based on tests known in the art, including, for example, A1C test, fasting plasma glucose test, oral glucose tolerance test, random plasma glucose test, fructosamine test, testing for ketones, and urine test. In some embodiments, ameliorating, controlling, reducing incidence of, or delaying the development or progression of T1D and/or symptoms of T1D is measured by fasting plasma glucose test.

In some embodiments, therapeutic administration of the anti-glucagon receptor antagonist antibody advantageously results in reduced incidence and/or amelioration of one or more symptoms of T1D including, for example, hyperglycemia, increased thirst, increased hunger, dry mouth, frequent urination, unexplained weight loss, fatigue, blurred vision, headaches, loss of consciousness, retinopathy, kidney damage, poor blood circulation, nerve damage, increased infections, ulcers, nausea, vomiting, diarrhea, tingling, numbness, pain in the hands or feet, dry skin, itchy skin, and slow to heal sores.

With respect to all methods described herein, reference to anti-glucagon receptor antagonist antibodies also includes compositions comprising one or more additional agents. These compositions may further comprise suitable excipients, such as pharmaceutically acceptable excipients including buffers, which are well known in the art. The present invention can be used alone or in combination with other methods of treatment.

The anti-glucagon receptor antagonist antibody can be administered to an individual via any suitable route. It should be apparent to a person skilled in the art that the examples described herein are not intended to be limiting but to be illustrative of the techniques available. Accordingly, in some embodiments, the anti-glucagon receptor antagonist antibody is administered to an individual in accord with known methods, such as intravenous administration, e.g., as a bolus or by continuous infusion over a period of time, by intramuscular, intraperitoneal, intracerebrospinal, transdermal, subcutaneous, intra-articular, sublingually, intrasynovial, via insufflation, intrathecal, oral, inhalation or topical routes. Administration can be systemic, e.g., intravenous administration, or localized. Commercially available nebulizers for liquid formulations, including jet nebulizers and ultrasonic nebulizers are useful for administration. Liquid formulations can be directly nebulized and lyophilized powder can be nebulized after reconstitution. Alternatively, anti-glucagon receptor antagonist antibody can be aerosolized using a fluorocarbon formulation and a metered dose inhaler, or inhaled as a lyophilized and milled powder.

In some embodiments, an anti-glucagon receptor antagonist antibody is administered via site-specific or targeted local delivery techniques. Examples of site-specific or targeted local delivery techniques include various implantable depot sources of the anti-glucagon receptor antagonist antibody or local delivery catheters, such as infusion catheters, indwelling catheters, or needle catheters, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Various formulations of an anti-glucagon receptor antagonist antibody may be used for administration. In some embodiments, the anti-glucagon receptor antagonist antibody may be administered neat. In some embodiments, anti-glucagon receptor antagonist antibody and a pharmaceutically acceptable excipient may be in various formulations. Pharmaceutically acceptable excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in Remington, The Science and Practice of Pharmacy 20th Ed. Mack Publishing, 2000.

In some embodiments, these agents are formulated for administration by injection (e.g., intraperitoneally, intravenously, subcutaneously, intramuscularly, etc.). Accordingly, these agents can be combined with pharmaceutically acceptable vehicles such as saline, Ringer's solution, dextrose solution, and the like. The particular dosage regimen, i.e., dose, timing and repetition, will depend on the particular individual and that individual's medical history.

An anti-glucagon receptor antagonist antibody can be administered using any suitable method, including by injection (e.g., intraperitoneally, intravenously, subcutaneously, intramuscularly, etc.). Anti-glucagon receptor antibodies can also be administered topically or via inhalation, as described herein. Generally, for administration of anti-glucagon receptor antibodies, an initial candidate dosage can be about 2 mg/kg. For the purpose of the present invention, a typical daily dosage might range from about any of 3 µg/kg to 30 µg/kg to 300 µg/kg to 3 mg/kg, to 30 mg/kg, to 100 mg/kg or more, depending on the factors mentioned above. For example, dosage of about 1 mg/kg, about 2.5 mg/kg, about 5 mg/kg, about 10 mg/kg, and about 25 mg/kg may be used. For repeated administrations over several days or longer, depending on the condition, the treatment is sustained until a desired suppression of symptoms occurs or until sufficient therapeutic levels are achieved, for example, to reduce symptoms associated with glucagon-related disorders. The progress of this therapy is easily monitored by conventional techniques and assays. The dosing regimen (including the anti-glucagon receptor antagonist antibody used) can vary over time.

For the purpose of the present invention, the appropriate dosage of an anti-glucagon receptor antagonist antibody will depend on the anti-glucagon receptor antagonist antibody (or compositions thereof) employed, the type and severity of symptoms to be treated, whether the agent is administered for preventive or therapeutic purposes, previous therapy, the patient's clinical history and response to the agent, the patient's blood glucose levels, the patient's synthesis and clearance rate for glucose, the patient's clearance rate for the administered agent, and the discretion of the attending physician. Typically the clinician will administer an anti-glucagon receptor antagonist antibody until a dosage is reached that achieves the desired result. Dose and/or frequency can vary over course of treatment. Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of symptoms. Alternatively, sustained continuous release formulations of anti-glucagon receptor antagonist antibodies may be appropriate. Various formulations and devices for achieving sustained release are known in the art.

In one embodiment, dosages for an antagonist antibody may be determined empirically in individuals who have been given one or more administration(s) of an antagonist antibody. Individuals are given incremental dosages of an anti-glucagon receptor antagonist antibody. To assess efficacy, an indicator of the disease can be followed.

Administration of an anti-glucagon receptor antagonist antibody in accordance with the method in the present invention can be continuous or intermittent, depending, for example, upon the recipient's physiological condition, whether the purpose of the administration is therapeutic or prophylactic, and other factors known to skilled practitioners. The administration of an anti-glucagon receptor antagonist antibody may be essentially continuous over a preselected period of time or may be in a series of spaced doses.

In some embodiments, more than one anti-glucagon receptor antagonist antibody may be present. At least one, at least two, at least three, at least four, at least five different, or more antagonist antibodies can be present. Generally, those anti-glucagon receptor antagonist antibodies may have complementary activities that do not adversely affect each other. An anti-glucagon receptor antagonist antibody can also be used in conjunction with other antibodies and/or other therapies. An anti-glucagon receptor antagonist antibody can also be used in conjunction with other agents that serve to enhance and/or complement the effectiveness of the agents.

In some embodiments, the anti-glucagon receptor antagonist antibody may be administered in combination with the administration of one or more additional therapeutic agents. These include, but are not limited to, the administration of mTOR inhibitors, meglitinides (e.g., repaglinide, nateglinide, etc.), sulfonylureas (e.g., glipizide, glimepiride, glyburide, etc.), dipeptidyl peptidase-4 (DPP-4) inhibitors (e.g., saxagliptin, sitagliptin, linagliptin, etc.), biguanides (e.g., metformin, etc.), thiazolidinediones (e.g., rosiglitazone, pioglitazone, etc.), alpha-glucosidase inhibitors (e.g., acarbose, voglibose, miglitol, etc.), amylin mimetics (e.g., symlin), and incretic mimetics (e.g., EXENATIDE®, liraglutide, etc.). Additional treatments include injectable treatments such as SYMLIN® (pramlintide).

In some embodiments, an anti-glucagon receptor antagonist antibody is used in conjunction with one or more mTOR inhibitors such as, for example without limitation, rapamycin, sirolimus, temsirolimus, everolimus, ridaforolimus, and/or an ATP-competitive mTOR kinase inhibitor (TKI). In some embodiments, the TKI is Torin1, Torin 2, PP242, PP30, KU0063794, WAY-600, WYE-687, WYE-354, OSI-027, AZD-8055, KU-BMCL-200908069-1, Wyeth-BMCL-200908069-2, XL-388, INK-128, and/or AZD-2014. In some embodiments, an anti-glucagon receptor antagonist antibody is used in conjunction with metformin, thiazolidinedione, sulfonylurea, and/or disaccharide inhibitor. Alternatively, the therapy may precede or follow the other agent treatment by intervals ranging from minutes to weeks. In embodiments where the other agents and/or a proteins or polynucleotides are administered separately, one would generally ensure that a significant period of time did not expire between each delivery, such that the agent and the composition of the present invention would still be able to exert an advantageously combined effect on the subject. In such instances, it is contemplated that one may administer both modalities within about 12-24 h of each other and, more preferably, within about 6-12 h of each other. In some situations, it may be desirable to extend the time period for administration significantly, however, where several days (2, 3, 4, 5, 6 or 7) to several weeks (1, 2, 3, 4, 5, 6, 7 or 8) lapse between the respective administrations.

In some embodiments, an anti-glucagon receptor antagonist antibody composition comprises a second agent selected from the group consisting of non-sulfonylurea secretagogues, insulin, insulin analogs, exendin-4 polypeptides, beta 3 adrenoceptor agonists, PPAR agonists, dipeptidyl peptidase IV inhibitors, statins and statin-containing combinations, inhibitors of cholesterol uptake and/or bile acid re-absorption, LDL-cholesterol antagonists, cholesteryl ester transfer protein antagonists, endothelin receptor antagonists, growth hormone antagonists, insulin sensitizers, amylin mimetics or agonists, cannabinoid receptor antagonists, glucagon-like peptide-1 agonists, melanocortins, and melanin-concentrating hormone receptor agonists.

Therapeutic formulations of the anti-glucagon receptor antagonist antibody used in accordance with the present invention are prepared for storage by mixing an antibody having the desired degree of purity with optional pharmaceutically acceptable carriers, excipients or stabilizers (Remington, The Science and Practice of Pharmacy 20th Ed. Mack Publishing, 2000), in the form of lyophilized formulations or aqueous solutions. Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Liposomes containing the anti-glucagon receptor antagonist antibody are prepared by methods known in the art, such as described in Epstein, et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The active ingredients may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington, The Science and Practice of Pharmacy 20th Ed. Mack Publishing (2000).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The formulations to be used for in vivo administration must be sterile. This is readily accomplished by, for example, filtration through sterile filtration membranes. Therapeutic anti-glucagon receptor antagonist antibody compositions are generally placed into a container having a sterile access port, for example, an intravenous solution bag or vial having a stopper pierceable by a hypodermic injection needle.

The compositions according to the present invention may be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from about 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 µm, particularly 0.1 and 0.5 µm, and have a pH in the range of 5.5 to 8.0.

The emulsion compositions can be those prepared by mixing an anti-glucagon receptor antagonist antibody with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Anti-Glucagon Receptor Antagonist Antibodies

The methods of the invention use an anti-glucagon receptor antagonist antibody that blocks, suppresses or reduces (including significantly reduces) glucagon receptor biological activity, including downstream events mediated by glucagon receptor. An anti-glucagon receptor antagonist antibody should exhibit any one or more of the following characteristics: (a) bind to glucagon receptor and block downstream signaling events; (b) block glucagon binding to glucagon receptor; (c) block adenylate cyclase activation; (d) block increase in intracellular cAMP; (e) block glycogenolysis; (f) block gluconeogenesis; and (g) block hepatic glucose production.

For purposes of this invention, the antibody preferably reacts with glucagon receptor in a manner that inhibits glucagon receptor signaling function. In some embodiments, the anti-glucagon receptor antagonist antibody specifically recognizes primate glucagon receptor.

The antibodies useful in the present invention can encompass monoclonal antibodies, polyclonal antibodies, antibody fragments (e.g., Fab, Fab', F(ab')$_2$, Fv, Fc, etc.), chimeric antibodies, bispecific antibodies, heteroconjugate antibodies, single chain (ScFv), mutants thereof, fusion proteins comprising an antibody portion (e.g., a domain antibody), humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or any other origin (including chimeric or humanized antibodies). In some embodiments, the anti-glucagon receptor antagonist antibody is a monoclonal antibody. In some embodiments, the antibody is a human or humanized antibody.

The anti-glucagon receptor antagonist antibodies may be made by any method known in the art. General techniques for production of human and mouse antibodies are known in the art and/or are described herein.

Anti-glucagon receptor antagonist antibodies can be identified or characterized using methods known in the art, whereby reduction, amelioration, or neutralization of glucagon receptor biological activity is detected and/or measured. In some embodiments, an anti-glucagon receptor antagonist antibody is identified by incubating a candidate agent with glucagon receptor and monitoring binding and/or attendant reduction or neutralization of a biological activity of glucagon receptor. The binding assay may be performed with, e.g., purified glucagon receptor polypeptide(s), or with cells naturally expressing (e.g., various strains), or transfected to express, glucagon receptor polypeptide(s). In one embodiment, the binding assay is a competitive binding assay, where the ability of a candidate antibody to compete with a known anti-glucagon receptor antagonist antibody for glucagon receptor binding is evaluated. The assay may be performed in various formats, including the ELISA format. In some embodiments, an anti-glucagon receptor antagonist antibody is identified by incubating a candidate antibody with glucagon receptor and monitoring binding.

Following initial identification, the activity of a candidate anti-glucagon receptor antagonist antibody can be further confirmed and refined by bioassays, known to test the targeted biological activities. In some embodiments, an in vitro cell or cytotoxicity assay is used to further characterize a candidate anti-glucagon receptor antagonist antibody. For example, a candidate antibody is incubated with CHO cells expressing glucagon receptor, and glucagon is added, and intracellular cAMP levels are monitored. Alternatively, bioassays can be used to screen candidates directly.

The anti-glucagon receptor antagonist antibodies of the invention exhibit one or more of the following characteristics: (a) bind to glucagon receptor and block downstream signaling events; (b) block glucagon binding to glucagon receptor; (c) block adenylate cyclase activation; (d) block increase in intracellular cAMP; (e) block glycogenolysis; (f) block gluconeogenesis; and (g) block hepatic glucose production. Preferably, anti-glucagon receptor antibodies have two or more of these features. More preferably, the antibodies have three or more of the features. More preferably, the antibodies have four or more of the features. More preferably, the antibodies have five or more of the features. More preferably, the antibodies have six or more of the features. Most preferably, the antibodies have all seven characteristics.

Anti-glucagon receptor antagonist antibodies may be characterized using methods well known in the art. For example, one method is to identify the epitope to which it binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an anti-glucagon receptor antagonist antibody binds. Epitope mapping is commercially available from various sources, for example, Pepscan Systems (Edelhertweg 15, 8219 PH Lelystad, The Netherlands). The epitope can be a linear epitope, i.e., contained in a single stretch of amino acids, or a conformational epitope formed by a three-dimensional interaction of amino acids that may not necessarily be contained in a single stretch. Peptides of varying lengths (e.g., at least 4-6 amino acids long) can be isolated or synthesized (e.g., recombinantly) and used for binding assays with an anti-glucagon receptor antagonist antibody. In another example, the epitope to which the anti-glucagon receptor antagonist antibody binds can be determined in a systematic screening by using overlapping peptides derived from the glucagon receptor sequence and determining binding by the anti-glucagon receptor antagonist antibody. According to the gene fragment expression assays, the open reading frame encoding glucagon receptor is fragmented either randomly or by specific genetic constructions and the reactivity of the expressed fragments of glucagon receptor with the antibody to be tested is determined. The gene fragments may, for example, be produced by PCR and then transcribed and translated into protein in vitro, in the presence of radioactive amino acids. The binding of the antibody to the radioactively labeled glucagon receptor fragments is then determined by immunoprecipitation and gel electrophoresis. Certain epitopes can also be identified by using large libraries of random peptide sequences displayed on the surface of phage particles (phage libraries) or yeast (yeast display). Alternatively, a defined library of overlapping peptide fragments can be tested for binding to the test antibody in simple binding assays. In an additional example, mutagenesis of an antigen, domain swapping experiments and alanine scanning mutagenesis can be performed to identify residues required, sufficient, and/or necessary for epitope binding. For example, alanine scanning mutagenesis experiments can be performed using a mutant glucagon receptor in which various residues of the glucagon receptor polypeptide have been replaced with alanine. By assessing binding of the antibody to the mutant glucagon receptor, the importance of the particular glucagon receptor residues to antibody binding can be assessed.

Yet another method which can be used to characterize an anti-glucagon receptor antagonist antibody is to use competition assays with other antibodies known to bind to the same antigen, i.e., various fragments of glucagon receptor, to determine if the anti-glucagon receptor antagonist antibody binds to the same epitope as other antibodies. Competition assays are well known to those of skill in the art.

The binding affinity ($K_D$) of an anti-glucagon receptor antagonist antibody to glucagon receptor can be about 0.001 to about 200 nM. In some embodiments, the binding affinity is any of about 200 nM, about 100 nM, about 50 nM, about 10 nM, about 1 nM, about 500 pM, about 100 pM, about 60 pM, about 50 pM, about 20 pM, about 15 pM, about 10 pM, about 5 pM, about 2 pM, or about 1 pM. In some embodiments, the binding affinity is less than any of about 250 nM, about 200 nM, about 100 nM, about 50 nM, about 10 nM, about 1 nM, about 500 pM, about 100 pM, about 50 pM, about 20 pM, about 10 pM, about 5 pM, or about 2 pM.

Accordingly, the invention provides any of the following, or compositions (including pharmaceutical compositions) comprising an antibody having a partial light chain sequence and a partial heavy chain sequence as found in Tables 1A or 1B, or variants thereof. In Tables 1A and 1B, the underlined sequences are CDR sequences according to Kabat, and the sequences in bold are CDR sequences according to Chothia.

TABLE 1A

Variable Regions Sequences of Anti-glucagon receptor antagonist Antibodies

| mAb | Light Chain | Heavy Chain | |
|---|---|---|---|
| mAb1 | DIVMTQSQKFMSASVGDRVSIT C<u>KASQNVRTAVV</u>WFQQKPGQ | QIQLVQSGPELKKPGETVKISCKA SGYTFTD<u>F</u>SIHWVKQAPGKGLKW | $K_D$ = 64 nM |

TABLE 1A-continued

Variable Regions Sequences of Anti-glucagon receptor antagonist Antibodies

| mAb | Light Chain | Heavy Chain | |
|---|---|---|---|
| | SPNTLIYLASNRHSEVPDRFTG SGSGTDFTLTISNVQSEDLADY FCLQHWTYPFTFASGTKLEIK (SEQ ID NO: 2) | MGWINTETDESTYADDFKGRFAF SLETSASTAYLQINNLKNEDTATYF CVKSRGWTYGPPDYWGQGTTLT VSS (SEQ ID NO: 3) | |
| mAb2 | DIQMTQSPSSLSASVGDRVTIT CRASQNIRTAVVWYQQKPGK APKLLIYLATNRHSGVPSRFSG SGSGTDFTFTISSLQPEDIATYY CLQHWTYPFSFGGGTKLEIK (SEQ ID NO: 4) | QVQLVQSGAEVKKPGASVKVSCK ASGYTFTDFSVHWVRQAPGQGLE WMGWINTETDETSYADDFKGRVT MTRDTSTSTVYMELSSLRSEDTAV YYCVKSRGWSYGPPDYWGQGTT VTVSS (SEQ ID NO: 5) | T½ = 5.75 min |
| mAb3 | DIQMTQSPASLAASVGETVTIT CRASENIYYSLAWYQQKQGKS PQLLIYNANSLEDGVPSRFSGS GSGTQYSMKINSIQPEDTATYF CKQAYDVPFTFGSGTKLVIK (SEQ ID NO: 6) | EVQLQQSGPELIKPGASVKMSCKA SGYTFTSCLIHWVKLKPGQGLEWI GYINPYNDGTKYNEKFKGRATLTS DKSSSTAYMELSSLTSEDSAVYYC ARMDYGNLWYFDVWGAGTTVTV SS (SEQ ID NO: 7) | |
| mAb4 | EIVLTQSPATLSLSPGERATLS CRASENIYYSLAWYQQKPGQA PRLLIYNANSLEDGIPARFSGS GSGTDFTLTISSLEPEDFAVYY CKQAYDVPFTFGGGTKVEIK (SEQ ID NO: 8) | QVQLVQSGAEVKKPGASVKVSCK ASGYTFTSSLIHWVRQAPGQGLE WMGYINPYNDGTKYNEKFKGRVT MTRDTSTSTVYMELSSLRSEDTAV YYCARMDYGNLWYFDVWGQGTL VTVSS (SEQ ID NO: 9) | K_D = 10.2 nM |
| mAb5 | DIQMTQSPSSLSASVGDRVTIT CQASQNIRTAVVWYQQKPGK APKLLIYLASNRHSGVPSRFSG SGSGTDFTFTISSLQPEDIATYY CLQHWTYPFTFGGGTKVEIK (SEQ ID NO: 10) | QVQLVQSGAEVKKPGASVKVSCK ASGYTFTDFSVHWVRQAPGQGLE WMGWINTETDETSYADDFKGRVT MTRDTSTSTVYMELSSLRSEDTAV YYCVKSRYWSYGPPDYWGQGTT VTVSS (SEQ ID NO: 11) | K_D = 224 pM |
| mAb6 | QIVLSQSPAILSASPGEKVTMT CRANSTLNYMHWYQQKPGSS PKPWIFGTSILASGVPLRFSGS GSGTSYSLTISRVETEDAATYY CQQWSSNPWTFGGGTKLEIK (SEQ ID NO: 42) | DVQFQESGPGLVKPSQSLSLTCTV TDYSFTSDYAWNWFRQFPGNKLE WMGYINYSGSTNYNPSLKSRISIT RDTSKNQFFLQLNSVTTEDTATYY CASTVVEGYYFDYWGQGTTLVS S (SEQ ID NO: 43) | |

TABLE 1B

Variable Regions Sequences of mAb5 Variants

| mAb | Light Chain | Heavy Chain | |
|---|---|---|---|
| H2-A8 | DIQMTQSPSSLSASVGDRVTIT CRASQNIRTAVVWYQQKPGK APKLLIYLATNRHSGVPSRFSG SGSGTDFTFTISSLQPEDIATYY CLQHWTYPFSFGGGTKLEIK (SEQ ID NO: 4) | QVQLVQSGAEVKKPGASVKVSCKA SGYTFTDFSVHWVRQAPGQGLEW MGWINTEFDFTSYADDFKGRVTMT RDTSTSTVYMELSSLRSEDTAVYY CVKSRGWSYGPPDYWGQGTTVTV SS (SEQ ID NO: 57) | T½ = 20.78 min. at 25° C. |
| H2-A11 | DIQMTQSPSSLSASVGDRVTIT CRASQNIRTAVVWYQQKPGK APKLLIYLATNRHSGVPSRFSG SGSGTDFTFTISSLQPEDIATYY CLQHWTYPFSFGGGTKLEIK (SEQ ID NO: 4) | QVQLVQSGAEVKKPGASVKVSCKA SGYTFTDFSVHWVRQAPGQGLEW MGWINTEYDFTSYADDFKGRVTMT RDTSTSTVYMELSSLRSEDTAVYY CVKSRGWSYGPPDYWGQGTTVTV SS (SEQ ID NO: 58) | T½ = 26.26 min. at 25° C. |
| H2-C8 | DIQMTQSPSSLSASVGDRVTIT CRASQNIRTAVVWYQQKPGK APKLLIYLATNRHSGVPSRFSG SGSGTDFTFTISSLQPEDIATYY CLQHWTYPFSFGGGTKLEIK (SEQ ID NO: 4) | QVQLVQSGAEVKKPGASVKVSCKA SGYTFTDFSVHWVRQAPGQGLEW MGWINTETRGTSYADDFKGRVTMT RDTSTSTVYMELSSLRSEDTAVYY CVKSRGWSYGPPDYWGQGTTVTV SS (SEQ ID NO: 59) | T½ = 20.63 min. at 25° C. |
| H2-E7 | DIQMTQSPSSLSASVGDRVTIT CRASQNIRTAVVWYQQKPGK APKLLIYLATNRHSGVPSRFSG SGSGTDFTFTISSLQPEDIATYY CLQHWTYPFSFGGGTKLEIK (SEQ ID NO: 4) | QVQLVQSGAEVKKPGASVKVSCKA SGYTFTDFSVHWVRQAPGQGLEW MGWYNLETDETSYADDFKGRVTM TRDTSTSTVYMELSSLRSEDTAVYY CVKSRGWSYGPPDYWGQGTTVTV SS (SEQ ID NO: 60) | T½ = 13.66 min. at 25° C. |

TABLE 1B -continued

Variable Regions Sequences of mAb5 Variants

| mAb | Light Chain | Heavy Chain | |
|---|---|---|---|
| H2-F10 | DIQMTQSPSSLSASVGDRVTITCRASQNIRTAVVWYQQKPGKAPKLLIYLATNRHSGVPSRFSGSGSGTDFTFTISSLQPEDIATYYCLQHWTYPFSFGGGTKLEIK(SEQ ID NO: 4) | QVQLVQSGAEVKKPGASVKVSCKASGYTFTDFSVHWVRQAPGQGLEWMGWINLEFDETSYADDFKGRVTMTRDTSTSTVYMELSSLRSEDTAVYYCVKSRGWSYGPPDYWGQGTTVTVSS (SEQ ID NO: 61) | $T^{1}/_{2}$ = 21.59 min. at 25° C. |
| H2-F11 | DIQMTQSPSSLSASVGDRVTITCRASQNIRTAVVWYQQKPGKAPKLLIYLATNRHSGVPSRFSGSGSGTDFTFTISSLQPEDIATYYCLQHWTYPFSFGGGTKLEIK(SEQ ID NO: 4) | QVQLVQSGAEVKKPGASVKVSCKASGYTFTDFSVHWVRQAPGQGLEWMGWINTEFDYTSYADDFKGRVTMTRDTSTSTVYMELSSLRSEDTAVYYCVKSRGWSYGPPDYWGQGTTVTVSS (SEQ ID NO: 62) | $T^{1}/_{2}$ = 17.75 min. at 25° C. |
| H3-C5 | DIQMTQSPSSLSASVGDRVTITCRASQNIRTAVVWYQQKPGKAPKLLIYLATNRHSGVPSRFSGSGSGTDFTFTISSLQPEDIATYYCLQHWTYPFSFGGGTKLEIK(SEQ ID NO: 4) | QVQLVQSGAEVKKPGASVKVSCKASGYTFTDFSVHWVRQAPGQGLEWMGWINTETDETSYADDFKGRVTMTRDTSTSTVYMELSSLRSEDTAVYYCVESLYWSYGPPDYWGQGTTVTVSS (SEQ ID NO: 63) | $T^{1}/_{2}$ = 5.34 min. at 25° C. |
| H3-C10 | DIQMTQSPSSLSASVGDRVTITCRASQNIRTAVVWYQQKPGKAPKLLIYLATNRHSGVPSRFSGSGSGTDFTFTISSLQPEDIATYYCLQHWTYPFSFGGGTKLEIK(SEQ ID NO: 4) | QVQLVQSGAEVKKPGASVKVSCKASGYTFTDFSVHWVRQAPGQGLEWMGWINTETDETSYADDFKGRVTMTRDTSTSTVYMELSSLRSEDTAVYYCVKSLYWSYGPPDYWGQGTTVTVSS (SEQ ID NO: 64) | $T^{1}/_{2}$ = 3.68 min. at 25° C. |
| H3-F5 | DIQMTQSPSSLSASVGDRVTITCRASQNIRTAVVWYQQKPGKAPKLLIYLATNRHSGVPSRFSGSGSGTDFTFTISSLQPEDIATYYCLQHWTYPFSFGGGTKLEIK(SEQ ID NO: 4) | QVQLVQSGAEVKKPGASVKVSCKASGYTFTDFSVHWVRQAPGQGLEWMGWINTETDETSYADDFKGRVTMTRDTSTSTVYMELSSLRSEDTAVYYCVKSLFWSYGPPDYWGQGTTVTVSS (SEQ ID NO: 65) | $T^{1}/_{2}$ = 2.4 min. at 25° C. |
| H3-H9 | DIQMTQSPSSLSASVGDRVTITCRASQNIRTAVVWYQQKPGKAPKLLIYLATNRHSGVPSRFSGSGSGTDFTFTISSLQPEDIATYYCLQHWTYPFSFGGGTKLEIK(SEQ ID NO: 4) | QVQLVQSGAEVKKPGASVKVSCKASGYTFTDFSVHWVRQAPGQGLEWMGWINTETDETSYADDFKGRVTMTRDTSTSTVYMELSSLRSEDTAVYYCVKSRWWSYGPPDYWGQGTTVTVSS (SEQ ID NO: 66) | $T^{1}/_{2}$ = 2.26 min. at 25° C. |
| H2-A11-H3-1 | DIQMTQSPSSLSASVGDRVTITCRASQNIRTAVVWYQQKPGKAPKLLIYLATNRHSGVPSRFSGSGSGTDFTFTISSLQPEDIATYYCLQHWTYPFSFGGGTKLEIK(SEQ ID NO: 4) | QVQLVQSGAEVKKPGASVKVSCKASGYTFTDFSVHWVRQAPGQGLEWMGWINTEYDFTSYADDFKGRVTMTRDTSTSTVYMELSSLRSEDTAVYYCVESLYWSYGPPDYWGQGTTVTVSS (SEQ ID NO: 67) | $T^{1}/_{2}$ = 4.19 h at 37° C. |
| H2-A11-H3-2 | DIQMTQSPSSLSASVGDRVTITCRASQNIRTAVVWYQQKPGKAPKLLIYLATNRHSGVPSRFSGSGSGTDFTFTISSLQPEDIATYYCLQHWTYPFSFGGGTKLEIK(SEQ ID NO: 4) | QVQLVQSGAEVKKPGASVKVSCKASGYTFTDFSVHWVRQAPGQGLEWMGWINTEYDFTSYADDFKGRVTMTRDTSTSTVYMELSSLRSEDTAVYYCVKSLFWSYGPPDYWGQGTTVTVSS (SEQ ID NO: 68) | $T^{1}/_{2}$ = 8.53 h at 37° C. |
| H2-A11-H3-3 | DIQMTQSPSSLSASVGDRVTITCRASQNIRTAVVWYQQKPGKAPKLLIYLATNRHSGVPSRFSGSGSGTDFTFTISSLQPEDIATYYCLQHWTYPFSFGGGTKLEIK(SEQ ID NO: 4) | QVQLVQSGAEVKKPGASVKVSCKASGYTFTDFSVHWVRQAPGQGLEWMGWINTEYDFTSYADDFKGRVTMTRDTSTSTVYMELSSLRSEDTAVYYCVKSLYWSYGPPDYWGQGTTVTVSS (SEQ ID NO: 69) | $T^{1}/_{2}$ = 17.21 h at 37° C. |
| H2-A11-H3-4 | DIQMTQSPSSLSASVGDRVTITCRASQNIRTAVVWYQQKPGKAPKLLIYLATNRHSGVPSRFSGSGSGTDFTFTISSLQPEDIATYYCLQHWTYPFSFGGGTKLEIK(SEQ ID NO: 4) | QVQLVQSGAEVKKPGASVKVSCKASGYTFTDFSVHWVRQAPGQGLEWMGWINTEYDFTSYADDFKGRVTMTRDTSTSTVYMELSSLRSEDTAVYYCVKSRWWSYGPPDYWGQGTTVTVSS (SEQ ID NO: 70) | $T^{1}/_{2}$ = 6.36 h at 37° C. |

TABLE 1B -continued

Variable Regions Sequences of mAb5 Variants

| mAb | Light Chain | Heavy Chain | |
|---|---|---|---|
| H2-C8-H3-1 | DIQMTQSPSSLSASVGDRVTITC<u>RASQNIRTAVV</u>WYQQKPGK APKLLIY<u>LATNRHS</u>GVPSRFSG SGSGTDFTFTISSLQPEDIATYY C<u>LQHWTYPFS</u>FGGGTKLEIK (SEQ ID NO: 4) | QVQLVQSGAEVKKPGASVKVSCKA S<u>GYTFTDF</u>SVHWVRQAPGQGLEW MGW<u>INTETRG</u>TSYADDFKGRVTMT RDTSTSTVYMELSSLRSEDTAVYY CVE<u>SLYWSYGPPDY</u>WGQGTTVTV SS (SEQ ID NO: 71) | |
| H2-C8-H3-2 | DIQMTQSPSSLSASVGDRVTITC<u>RASQNIRTAVV</u>WYQQKPGK APKLLIY<u>LATNRHS</u>GVPSRFSG SGSGTDFTFTISSLQPEDIATYY C<u>LQHWTYPFS</u>FGGGTKLEIK (SEQ ID NO: 4) | QVQLVQSGAEVKKPGASVKVSCKA S<u>GYTFTDF</u>SVHWVRQAPGQGLEW MGW<u>INTETRG</u>TSYADDFKGRVTMT RDTSTSTVYMELSSLRSEDTAVYY CVK<u>SLFWSYGPPDY</u>WGQGTTVTV SS (SEQ ID NO: 72) | T½ = 6.89 h at 37° C. |
| H2-C8-H3-3 | DIQMTQSPSSLSASVGDRVTITC<u>RASQNIRTAVV</u>WYQQKPGK APKLLIY<u>LATNRHS</u>GVPSRFSG SGSGTDFTFTISSLQPEDIATYY C<u>LQHWTYPFS</u>FGGGTKLEIK (SEQ ID NO: 4) | QVQLVQSGAEVKKPGASVKVSCKA S<u>GYTFTDF</u>SVHWVRQAPGQGLEW MGW<u>INTETRG</u>TSYADDFKGRVTMT RDTSTSTVYMELSSLRSEDTAVYY CVK<u>SLYWSYGPPDY</u>WGQGTTVTV SS (SEQ ID NO: 73) | T½ = 12.38 h at 37° C. |
| H2-C8-H3-4 | DIQMTQSPSSLSASVGDRVTITC<u>RASQNIRTAVV</u>WYQQKPGK APKLLIY<u>LATNRHS</u>GVPSRFSG SGSGTDFTFTISSLQPEDIATYY C<u>LQHWTYPFS</u>FGGGTKLEIK (SEQ ID NO: 4) | QVQLVQSGAEVKKPGASVKVSCKA S<u>GYTFTDF</u>SVHWVRQAPGQGLEW MGW<u>INTETRG</u>TSYADDFKGRVTMT RDTSTSTVYMELSSLRSEDTAVYY CVK<u>SRWWSYGPPDY</u>WGQGTTVT VSS (SEQ ID NO: 74) | T½ = 5.30 h at 37° C. |
| H2-E7-H3-1 | DIQMTQSPSSLSASVGDRVTITC<u>RASQNIRTAVV</u>WYQQKPGK APKLLIY<u>LATNRHS</u>GVPSRFSG SGSGTDFTFTISSLQPEDIATYY C<u>LQHWTYPFS</u>FGGGTKLEIK (SEQ ID NO: 4) | QVQLVQSGAEVKKPGASVKVSCKA S<u>GYTFTDF</u>SVHWVRQAPGQGLEW MGW<u>YNLETDE</u>TSYADDFKGRVTM TRDTSTSTVYMELSSLRSEDTAVYY CVE<u>SLYWSYGPPDY</u>WGQGTTVTV SS (SEQ ID NO: 75) | |
| H2-E7-H3-2 | DIQMTQSPSSLSASVGDRVTITC<u>RASQNIRTAVV</u>WYQQKPGK APKLLIY<u>LATNRHS</u>GVPSRFSG SGSGTDFTFTISSLQPEDIATYY C<u>LQHWTYPFS</u>FGGGTKLEIK (SEQ ID NO: 4) | QVQLVQSGAEVKKPGASVKVSCKA S<u>GYTFTDF</u>SVHWVRQAPGQGLEW MGW<u>YNLETDE</u>TSYADDFKGRVTM TRDTSTSTVYMELSSLRSEDTAVYY CVK<u>SLFWSYGPPDY</u>WGQGTTVTV SS (SEQ ID NO: 76) | T½ = 7.94 h at 37° C. |
| H2-E7-H3-3 | DIQMTQSPSSLSASVGDRVTITC<u>RASQNIRTAVV</u>WYQQKPGK APKLLIY<u>LATNRHS</u>GVPSRFSG SGSGTDFTFTISSLQPEDIATYY C<u>LQHWTYPFS</u>FGGGTKLEIK (SEQ ID NO: 4) | QVQLVQSGAEVKKPGASVKVSCKA S<u>GYTFTDF</u>SVHWVRQAPGQGLEW MGW<u>YNLETDE</u>TSYADDFKGRVTM TRDTSTSTVYMELSSLRSEDTAVYY CVK<u>SLYWSYGPPDY</u>WGQGTTVTV SS (SEQ ID NO: 77) | T½ = 14.86 h at 37° C. |
| H2-E7-H3-4 | DIQMTQSPSSLSASVGDRVTITC<u>RASQNIRTAVV</u>WYQQKPGK APKLLIY<u>LATNRHS</u>GVPSRFSG SGSGTDFTFTISSLQPEDIATYY C<u>LQHWTYPFS</u>FGGGTKLEIK (SEQ ID NO: 4) | QVQLVQSGAEVKKPGASVKVSCKA S<u>GYTFTDF</u>SVHWVRQAPGQGLEW MGW<u>YNLETDE</u>TSYADDFKGRVTM TRDTSTSTVYMELSSLRSEDTAVYY CVK<u>SRWWSYGPPDY</u>WGQGTTVT VSS (SEQ ID NO: 78) | T½ = 7.37 h at 37° C. |
| FF1 | DIQMTQSPSSLSASVGDRVTITC<u>RASQNIRTAVV</u>WYQQKPGK APKLLIY<u>LATNRHS</u>GVPSRFSG SGSGTDFTFTISSLQPEDIATYY C<u>LQHWTYPFS</u>FGGGTKLEIK (SEQ ID NO: 4) | QVQLVQSGAEVKKPGASVKVSCKA S<u>GYTFTDF</u>SVHWVRQAPGQGLEW MGW<u>INTEYDF</u>TSYADDFKGRVTMT RDTSTSTVYMELSSLRSEDTAVYY CVK<u>SLYWSYGPPDY</u>WGQGTTVTV SS (SEQ ID NO: 78) | |
| FF2 | DIQMTQSPSSLSASVGDRVTITC<u>QASQNIRTAVV</u>WYQQKPGK APKLLIY<u>LASNRHS</u>GVPSRFSG SGSGTDFTFTISSLQPEDIATYY C<u>LQHWTYPFT</u>FGGGTKVEIK (SEQ ID NO: 79) | QVQLVQSGAEVKKPGASVKVSCKA S<u>GYTFTDF</u>SVHWVRQAPGQGLEW MGW<u>INTEYDF</u>TSYADDFKGRVTMT RDTSTSTVYMELSSLRSEDTAVYY CVK<u>SLYWSYGPPDY</u>WGQGTTVTV SS (SEQ ID NO: 80) | kD = 171 pM |

TABLE 1B -continued

Variable Regions Sequences of mAb5 Variants

| mAb | Light Chain | Heavy Chain | |
|---|---|---|---|
| FF3 | DIQMTQSPSSLSASVGDRVTIT<br>CRASQNIRTAVVWYQQKPGK<br>APKLLIYLATNRHSGVPSRFSG<br>SGSGTDFTFTISSLQPEDIATYY<br>CLQHWTYPFSFGGGTKLEIK<br>(SEQ ID NO: 4) | QVQLVQSGAEVKKPGASVKVSCKA<br>SGYTFTDFSVHWVRQAPGQGLEW<br>MGWINTEYDFTSYAQKFQGRVTMT<br>RDTSTSTVYMELSSLRSEDTAVYY<br>CVKSLYWSYGPPDYWGQGTLVTV<br>SS (SEQ ID NO: 81) | |
| FF4 | DIQMTQSPSSLSASVGDRVTIT<br>CQASQNIRTAVVWYQQKPGK<br>APKLLIYLASNRHSGVPSRFSG<br>SGSGTDFTFTISSLQPEDIATYY<br>CLQHWTYPFTFGGGTKVEIK<br>(SEQ ID NO: 79) | QVQLVQSGAEVKKPGASVKVSCKA<br>SGYTFTDFSVHWVRQAPGQGLEW<br>MGWINTEYDFTSYAQKFQGRVTMT<br>RDTSTSTVYMELSSLRSEDTAVYY<br>CVKSLYWSYGPPDYWGQGTLVTV<br>SS (SEQ ID NO: 82) | |
| FF2-<br>H2WT | DIQMTQSPSSLSASVGDRVTIT<br>CQASQNIRTAVVWYQQKPGK<br>APKLLIYLASNRHSGVPSRFSG<br>SGSGTDFTFTISSLQPEDIATYY<br>CLQHWTYPFTFGGGTKVEIK<br>(SEQ ID NO: 79) | QVQLVQSGAEVKKPGASVKVSCKA<br>SGYTFTDFSVHWVRQAPGQGLEW<br>MGWINTETDETSYADDFKGRVTMT<br>RDTSTSTVYMELSSLRSEDTAVYY<br>CVKSLYWSYGPPDYWGQGTTVTV<br>SS (SEQ ID NO: 83) | kD =<br><200 pM |
| FF2-<br>H2RG | DIQMTQSPSSLSASVGDRVTIT<br>CQASQNIRTAVVWYQQKPGK<br>APKLLIYLASNRHSGVPSRFSG<br>SGSGTDFTFTISSLQPEDIATYY<br>CLQHWTYPFTFGGGTKVEIK<br>(SEQ ID NO: 79) | QVQLVQSGAEVKKPGASVKVSCKA<br>SGYTFTDFSVHWVRQAPGQGLEW<br>MGWINTETRGTSYADDFKGRVTMT<br>RDTSTSTVYMELSSLRSEDTAVYY<br>CVKSLYWSYGPPDYWGQGTTVTV<br>SS (SEQ ID NO: 84) | kD =<br>187 pM |
| FF2-<br>H3RY | DIQMTQSPSSLSASVGDRVTIT<br>CQASQNIRTAVVWYQQKPGK<br>APKLLIYLASNRHSGVPSRFSG<br>SGSGTDFTFTISSLQPEDIATYY<br>CLQHWTYPFTFGGGTKVEIK<br>(SEQ ID NO: 79) | QVQLVQSGAEVKKPGASVKVSCKA<br>SGYTFTDFSVHWVRQAPGQGLEW<br>MGWINTEYDFTSYADDFKGRVTMT<br>RDTSTSTVYMELSSLRSEDTAVYY<br>CVKSRYWSYGPPDYWGQGTTVTV<br>SS (SEQ ID NO: 85) | kD =<br><125 pM |
| FF2-<br>H2WT<br>H3RY | DIQMTQSPSSLSASVGDRVTIT<br>CQASQNIRTAVVWYQQKPGK<br>APKLLIYLASNRHSGVPSRFSG<br>SGSGTDFTFTISSLQPEDIATYY<br>CLQHWTYPFTFGGGTKVEIK<br>(SEQ ID NO: 79) | QVQLVQSGAEVKKPGASVKVSCKA<br>SGYTFTDFSVHWVRQAPGQGLEW<br>MGWINTETDETSYADDFKGRVTMT<br>RDTSTSTVYMELSSLRSEDTAVYY<br>CVKSRYWSYGPPDYWGQGTTVTV<br>SS (SEQ ID NO: 86) | kD =<br>224 pM |

The invention also provides CDR portions of antibodies to glucagon receptor. Determination of CDR regions is well within the skill of the art. It is understood that in some embodiments, CDRs can be a combination of the Kabat and Chothia CDR (also termed "combined CDRs" or "extended CDRs"). In another approach, referred to herein as the "conformational definition" of CDRs, the positions of the CDRs may be identified as the residues that make enthalpic contributions to antigen binding. See, e.g., Makabe et al., 2008, Journal of Biological Chemistry, 283:1156-1166. In general, "conformational CDRs" include the residue positions in the Kabat CDRs and Vernier zones which are constrained in order to maintain proper loop structure for the antibody to bind a specific antigen. Determination of conformational CDRs is well within the skill of the art. In some embodiments, the CDRs are the Kabat CDRs. In other embodiments, the CDRs are the Chothia CDRs. In other embodiments, the CDRs are the extended, AbM, conformational, or contact CDRs. In other words, in embodiments with more than one CDR, the CDRs may be any of Kabat, Chothia, extended, AbM, conformational, contact CDRs or combinations thereof.

In some embodiments, the antibody comprises three CDRs of any one of the heavy chain variable regions shown in Table 1A or 1B. In some embodiments, the antibody comprises three CDRs of any one of the light chain variable regions shown in Table 1A or 1B. In some embodiments, the antibody comprises three CDRs of any one of the heavy chain variable regions shown in Table 1A or 1B, and three CDRs of any one of the light chain variable regions shown in Table 1A or 1B.

Tables 2A and 2B provide examples of CDR sequences of anti-glucagon receptor antagonist antibodies provided herein.

TABLE 2A

Anti-glucagon receptor antagonist antibodies and antigen-binding
CDR sequences according to Kabat (underlined) and Chothia (bold)

| mAb | | CDR1 | CDR2 | CDR3 |
|---|---|---|---|---|
| mAb1 | LC | KAS<u>QNVRTAVV</u> (SEQ ID NO: 12) | <u>LASNRHS</u> (SEQ ID NO: 13) | <u>LQHWTYPFT</u> (SEQ ID NO: 14) |

TABLE 2A -continued

Anti-glucagon receptor antagonist antibodies and antigen-binding
CDR sequences according to Kabat (underlined) and Chothia (bold)

| mAb | | CDR1 | CDR2 | CDR3 |
|---|---|---|---|---|
| | HC | GYTFTDFSIH (SEQ ID NOs: 15 (whole), 16 and 17) | WINTETDESTYADDFKG (SEQ ID NOs: 18 and 19) | SRGWTYGPPDY (SEQ ID NO: 20) |
| mAb2 | LC | RASQNIRTAVV (SEQ ID NO: 21) | LATNRHS (SEQ ID NO: 22) | LQHWTYPFS (SEQ ID NO: 23) |
| | HC | GYTFTDFSVH (SEQ ID NOs: 24 (whole), 16 and 25) | WINTETDETSYADDFKG (SEQ ID NOs: 18 and 26) | SRGWSYGPPDY (SEQ ID NO: 27) |
| mAb3 | LC | RASENIYYSLA (SEQ ID NO: 28) | NANSLED (SEQ ID NO: 29) | KQAYDVPFT (SEQ ID NO: 30) |
| | HC | GYTFTSCLIH (SEQ ID NOs: 31 (whole), 32 and 33) | YINPYNDGTKYNEKFKG (SEQ ID NOs: 34 and 35) | MDYGNLWYFDV (SEQ ID NO: 36) |
| mAb4 | LC | RASENIYYSLA (SEQ ID NO: 28) | NANSLED (SEQ ID NO: 28) | KQAYDVPFT (SEQ ID NO: 28) |
| | HC | GYTFTSSLIH (SEQ ID NOs: 37 (whole), 38 and 39) | YINPYNDGTKYNEKFKG (SEQ ID NOs: 34 and 35) | MDYGNLWYFDV (SEQ ID NO: 36) |
| mAb5 | LC | QASQNIRTAVV (SEQ ID NO: 40) | LASNRHS (SEQ ID NO: 13) | LQHWTYPFT (SEQ ID NO: 14) |
| | HC | GYTFTDFSVH (SEQ ID NOs: 24 (whole), 16 and 25) | WINTETDETSYADDFKG (SEQ ID NOs: 18 and 26) | SRYWSYGPPDY (SEQ ID NO: 41) |

TABLE 2B mAb5 Variants

| | Light Chain | | | Heavy Chain | | | $T^{1/2}$ |
|---|---|---|---|---|---|---|---|
| mAb | CDR1 | CDR2 | CDR3 | CDR1 | CDR2 | CDR3 | [s] |
| LM1 | RASQNVRTAVV (SEQ ID NO: 44) | LASNRHS (SEQ ID NO: 13) | LQHWTYPFT (SEQ ID NO: 14) | DFSIH (SEQ ID NO: 17) | WINTETDESTY ADDFKG (SEQ ID NO: 19) | SRGWTYG PPDY (SEQ ID NO: 20) | 1527 |
| LM2 | RASQNIRTAVV (SEQ ID NO: 21) | LASNRHS (SEQ ID NO: 13) | LQHWTYPFT (SEQ ID NO: 14) | DFSIH (SEQ ID NO: 17) | WINTETDESTY ADDFKG (SEQ ID NO: 19) | SRGWTYG PPDY (SEQ ID NO: 20) | 1501 |
| LM3 | KASQNVRSAVV (SEQ ID NO: 45) | LASNRHS (SEQ ID NO: 13) | LQHWTYPFT (SEQ ID NO: 14) | DFSIH (SEQ ID NO: 17) | WINTETDESTY ADDFKG (SEQ ID NO: 19) | SRGWTYG PPDY (SEQ ID NO: 20) | 781 |
| LM4 | KASQNVRTALN (SEQ ID NO: 46) | LASNRHS (SEQ ID NO: 13) | LQHWTYPFT (SEQ ID NO: 14) | DFSIH (SEQ ID NO: 17) | WINTETDESTY ADDFKG (SEQ ID NO: 19) | SRGWTYG PPDY (SEQ ID NO: 20) | 754 |
| LM6 | KASQNVRTAVV (SEQ ID NO: 12) | LATNRHS (SEQ ID NO: 47) | LQHWTYPFT (SEQ ID NO: 14) | DFSIH (SEQ ID NO: 17) | WINTETDESTY ADDFKG (SEQ ID NO: 19) | SRGWTYG PPDY (SEQ ID NO: 20) | 1685 |
| LM7 | KASQNVRTAVV (SEQ ID NO: 12) | LASNRHG (SEQ ID NO: 48) | LQHWTYPFT (SEQ ID NO: 14) | DFSIH (SEQ ID NO: 17) | WINTETDESTY ADDFKG (SEQ ID NO: 19) | SRGWTYG PPDY (SEQ ID NO: 20) | 1397 |
| LM8 | KASQNVRTAVV (SEQ ID NO: 12) | LASNRHS (SEQ ID NO: 13) | QQHWTYPFT (SEQ ID NO: 49) | DFSIH (SEQ ID NO: 17) | WINTETDESTY ADDFKG (SEQ ID NO: 19) | SRGWTYG PPDY (SEQ ID NO: 20) | 473 |
| LM9 | KASQNVRTAVV (SEQ ID NO: 12) | LASNRHS (SEQ ID NO: 13) | LQHWSYPFT (SEQ ID NO: 49) | DFSIH (SEQ ID NO: 17) | WINTETDESTY ADDFKG (SEQ ID NO: 19) | SRGWTYG PPDY (SEQ ID NO: 20) | 688 |
| LM11 | KASQNVRTAVV (SEQ ID NO: 12) | LASNRHS (SEQ ID NO: 13) | LQHWTYPFS (SEQ ID NO: 50) | DFSIH (SEQ ID NO: 17) | WINTETDESTY ADDFKG (SEQ ID NO: 19) | SRGWTYG PPDY (SEQ ID NO: 20) | 1683 |

TABLE 2B -continued mAb5 Variants

| mAb | Light Chain | | | Heavy Chain | | | T½ [s] |
|---|---|---|---|---|---|---|---|
| | CDR1 | CDR2 | CDR3 | CDR1 | CDR2 | CDR3 | |
| HM5 | KASQNVRTAVV (SEQ ID NO: 12) | LASNRHS (SEQ ID NO: 13) | LQHWTYPFT (SEQ ID NO: 14) | DFSIH (SEQ ID NO: 17) | WINTESDESTYADDFKG (SEQ ID NO: 51) | SRGWTYGPPDY (SEQ ID NO: 20) | 1428 |
| HM6 | KASQNVRTAVV (SEQ ID NO: 12) | LASNRHS (SEQ ID NO: 13) | LQHWTYPFT (SEQ ID NO: 14) | DFSIH (SEQ ID NO: 17) | WINTETDETSYADDFKG (SEQ ID NO: 52) | SRGWTYGPPDY (SEQ ID NO: 20) | 2068 |
| HM7 | KASQNVRTAVV (SEQ ID NO: 12) | LASNRHS (SEQ ID NO: 13) | LQHWTYPFT (SEQ ID NO: 14) | DFSIH (SEQ ID NO: 17) | WINSETDESTYADDFKG (SEQ ID NO: 53) | SRGWTYGPPDY (SEQ ID NO: 20) | 921 |
| HM8 | KASQNVRTAVV (SEQ ID NO: 12) | LASNRHS (SEQ ID NO: 13) | LQHWTYPFT (SEQ ID NO: 14) | DFSIH (SEQ ID NO: 17) | WINTETDESTYAQNFQG (SEQ ID NO: 54) | SRGWTYGPPDY (SEQ ID NO: 20) | 1559 |
| HM11 | KASQNVRTAVV (SEQ ID NO: 12) | LASNRHS (SEQ ID NO: 13) | LQHWTYPFT (SEQ ID NO: 14) | DFSIH (SEQ ID NO: 17) | WINTETDESTYADDFKG (SEQ ID NO: 19) | VKSRGWSYGPPDY (SEQ ID NO: 55) | 2028 |
| HM12 | KASQNVRTAVV (SEQ ID NO: 12) | LASNRHS (SEQ ID NO: 13) | LQHWTYPFT (SEQ ID NO: 14) | DFSIH (SEQ ID NO: 17) | WINTETDESTYADDFKG (SEQ ID NO: 19) | VKSRGWTYGPPDV (SEQ ID NO: 56) | 1191 |

In some embodiments, the antibody comprises three light chain CDRs and three heavy chain CDRs from Table 2B. Consensus sequences from variants shown in Table 2B are as follows: light chain variable region CDR1: $X_1ASQNX_2RX_3AX_4X_5$, wherein $X_1$ is K or R, $X_2$ is V or I, $X_3$ is T or S, $X_4$ is V or L, and $X_5$ is V or N (SEQ ID NO: 90). Light chain variable region CDR2: $LAX_1NRH X_2$, wherein $X_1$ is S or T, and $X_2$ is S or G (SEQ ID NO: 91). Light chain variable region CDR3: $X_1QHWX_2YPFX_3$, wherein $X_1$ is L or Q, $X_2$ is T or S, and $X_3$ is T or S (SEQ ID NO: 92). Heavy chain variable region CDR2: $WINX_1 EX_2DEX_3X_4YAX_5X_6FX_7G$ wherein $X_1$ is T or S, $X_2$ is T or S, $X_3$ is T or S, $X_4$ is S or T, $X_5$ is D or Q, $X_6$ is D or N, and $X_7$ is K or Q (SEQ ID NO: 93). Heavy chain variable region CDR3: $SRGWX_1YGPPDX_2$, wherein $X_1$ is T or S, and $X_2$ is Y or V (SEQ ID NO: 94).

In some embodiments, the antibody comprises the full-length heavy chain, with or without the C-terminal lysine, and/or the full-length light chain of anti-glucagon receptor antagonist antibody mAb5. The amino acid sequence of mAb5 full-length heavy chain (SEQ ID NO: 87) is shown below:

```
                                          (SEQ ID NO: 87)
QVQLVQSGAEVKKPGASVKVSCKASGYTFTDFSVHWVRQAPGQGLEWMG

WINTETDETSYADDFKGRVTMTRDTSTSTVYMELSSLRSEDTAVYYCVK

SRYWSYGPPDYWGQGTTVTVSSASTKGPSVFPLAPCSRSTSESTAALGC

LVKDYFPEPVTVSWNSGALTSGVHTFPAVLQSSGLYSLSSVVTVPSSNF

GTQTYTCNVDHKPSNTKVDKTVERKCCVECPPCPAPPVAGPSVFLFPPK

KPKDTLMISRTPEVTCVVVDVSHEDPEVQFNWYVDGVEVHNAKTPREEQ

FNSTFRVVSVLTVVHQDWLNGKEYKCKVSNKGLPSSIEKTISKTKGQPR

EPQVYTLPPSREEMTKNQVSLTCLVKGFYPSDIAVEWESNGQPENNYKT

TPPMLDSDGSFFLYSKLTVDKSRWQQGNVFSCSVMHEALHNHYTQKSLS

LSPGK
```

The amino acid sequence of mAb5 full-length heavy chain without the C-terminal lysine (SEQ ID NO: 88) is shown below:

```
                                          (SEQ ID NO: 88)
QVQLVQSGAEVKKPGASVKVSCKASGYTFTDFSVHWVRQAPGQGLEWMG

WINTETDETSYADDFKGRVTMTRDTSTSTVYMELSSLRSEDTAVYYCVK

SRYWSYGPPDYWGQGTTVTVSSASTKGPSVFPLAPCSRSTSESTAALGC

LVKDYFPEPVTVSWNSGALTSGVHTFPAVLQSSGLYSLSSVVTVPSSNF

GTQTYTCNVDHKPSNTKVDKTVERKCCVECPPCPAPPVAGPSVFLFPPK

PKDTLMISRTPEVTCVVVDVSHEDPEVQFNWYVDGVEVHNAKTPREEQ

FNSTFRVVSVLTVVHQDWLNGKEYKCKVSNKGLPSSIEKTISKTKGQPR

EPQVYTLPPSREEMTKNQVSLTCLVKGFYPSDIAVEWESNGQPENNYKT

TPPMLDSDGSFFLYSKLTVDKSRWQQGNVFSCSVMHEALHNHYTQKSLS

LSPG
```

The amino acid sequence of mAb5 full-length light chain (SEQ ID NO: 89) is shown below:

```
                                          (SEQ ID NO: 89)
DIQMTQSPSSLSASVGDRVTITCQASQNIRTAVVWYQQKPGKAPKLLIY

LASNRHSGVPSRFSGSGSGTDFTFTISSLQPEDIATYYCLQHWTYPFTF

GGGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC
```

The invention also provides methods of generating, selecting, and making anti-glucagon receptor antagonist antibodies. The antibodies of this invention can be made by procedures known in the art. In some embodiments, antibodies may be made recombinantly and expressed using any method known in the art.

In some embodiments, antibodies may be prepared and selected by phage display technology. See, for example, U.S. Pat. Nos. 5,565,332; 5,580,717; 5,733,743; and 6,265,150; and Winter et al., Annu. Rev. Immunol. 12:433-455, 1994. Alternatively, the phage display technology (McCafferty et al., Nature 348:552-553, 1990) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for review see, e.g., Johnson, Kevin S, and Chiswell, David J., Current Opinion in Structural Biology 3:564-571, 1993. Several sources of V-gene segments can be used for phage display. Clackson et al., Nature 352:624-628, 1991, isolated a diverse array of anti-oxazolone antibodies from a small random combinatorial library of V genes derived from the spleens of immunized mice. A repertoire of V genes from human donors can be constructed and antibodies to a diverse array of antigens (including self-antigens) can be isolated essentially following the techniques described by Mark et al., J. Mol. Biol. 222: 581-597, 1991, or Griffith et al., EMBO J. 12:725-734, 1993. In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling." (Marks et al., Bio/Technol. 10:779-783, 1992). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the pM-nM range. A strategy for making very large phage antibody repertoires (also known as "the mother-of-all libraries") has been described by Waterhouse et al., Nucl. Acids Res. 21:2265-2266, 1993. Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable regions capable of restoring a functional antigen-binding site, i.e., the epitope governs (imprints) the choice of partner. When the process is repeated in order to replace the remaining rodent V domain, a human antibody is obtained (see PCT Publication No. WO 93/06213). Unlike traditional humanization of rodent antibodies by CDR grafting, this technique provides completely human antibodies, which have no framework or CDR residues of rodent origin.

In some embodiments, antibodies may be made using hybridoma technology. It is contemplated that any mammalian subject including humans or antibody producing cells therefrom can be manipulated to serve as the basis for production of mammalian, including human, hybridoma cell lines. The route and schedule of immunization of the host animal are generally in keeping with established and conventional techniques for antibody stimulation and production, as further described herein. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C., 1975, Nature 256:495-497 or as modified by Buck, D. W., et al., In Vitro, 18:377-381, 1982. Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the glucagon receptor monoclonal antibodies of the subject invention. The hybridomas or other immortalized B-cells are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies specific for glucagon receptor, or a portion thereof.

Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity, if present, can be removed, for example, by running the preparation over adsorbents made of the immunogen attached to a solid phase and eluting or releasing the desired antibodies off the immunogen. Immunization of a host animal with a glucagon receptor polypeptide, or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups, can yield a population of antibodies (e.g., monoclonal antibodies).

If desired, the anti-glucagon receptor antagonist antibody (monoclonal or polyclonal) of interest may be sequenced and the polynucleotide sequence may then be cloned into a vector for expression or propagation. The sequence encoding the antibody of interest may be maintained in vector in a host cell and the host cell can then be expanded and frozen for future use. Production of recombinant monoclonal antibodies in cell culture can be carried out through cloning of antibody genes from B cells by means known in the art. See, e.g. Tiller et al., 2008, J. Immunol. Methods 329, 112; U.S. Pat. No. 7,314, 622.

In some embodiments, the polynucleotide sequence may be used for genetic manipulation to "humanize" the antibody or to improve the affinity, or other characteristics of the antibody. Antibodies may also be customized for use, for example, in dogs, cats, primate, equines and bovines.

In some embodiments, fully human antibodies may be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse™ from Abgenix, Inc. (Fremont, Calif.) and HuMAb-Mouse® and TC Mouse™ from Medarex, Inc. (Princeton, N.J.).

Antibodies may be made recombinantly by first isolating the antibodies and antibody producing cells from host animals, obtaining the gene sequence, and using the gene sequence to express the antibody recombinantly in host cells (e.g., CHO cells). Another method which may be employed is to express the antibody sequence in plants (e.g., tobacco) or transgenic milk. Methods for expressing antibodies recombinantly in plants or milk have been disclosed. See, for example, Peeters, et al. Vaccine 19:2756, 2001; Lonberg, N. and D. Huszar Int. Rev. Immunol 13:65, 1995; and Pollock, et al., J Immunol Methods 231:147, 1999. Methods for making derivatives of antibodies, e.g., domain, single chain, etc. are known in the art.

Immunoassays and flow cytometry sorting techniques such as fluorescence activated cell sorting (FACS) can also be employed to isolate antibodies that are specific for glucagon receptor.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors (such as expression vectors disclosed in PCT Publication No. WO 87/04462), which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA also may be modified, for example, by substituting the coding sequence for human heavy and light chain constant domains in place of the homologous murine sequences, Morrison et al., Proc. Nat. Acad. Sci. 81:6851, 1984, or by covalently joining to the immunoglobulin coding sequence all or part of the coding sequence for a non-immunoglobulin polypeptide. In that manner, "chimeric" or "hybrid" antibodies are prepared that have the binding specificity of a glucagon receptor monoclonal antibody herein.

Antibody fragments can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, an antibody could be produced by an automated polypeptide synthesizer employing the solid phase method. See also, U.S. Pat. Nos. 5,807,715; 4,816,567; and 6,331,415.

In some embodiments, a polynucleotide comprises a sequence encoding the heavy chain and/or the light chain variable regions of antibody mAb1, mAb2, mAb3, mAb4, mAb5, mAb6, LM1, LM2, LM3, LM4, LM6, LM7, LMB, LM9, LM11, HM4, HM6, HM7, HM8, HM11, or HM12. The sequence encoding the antibody of interest may be maintained in a vector in a host cell and the host cell can then be expanded and frozen for future use. Vectors (including expression vectors) and host cells are further described herein.

The invention includes affinity matured embodiments. For example, affinity matured antibodies can be produced by procedures known in the art (Marks et al., 1992, Bio/Technology, 10:779-783; Barbas et al., 1994, Proc Nat. Acad. Sci, USA 91:3809-3813; Schier et al., 1995, Gene, 169:147-155; Yelton et al., 1995, J. Immunol., 155:1994-2004; Jackson et al., 1995, J. Immunol., 154(7):3310-9; Hawkins et al., 1992, J. Mol. Biol., 226:889-896; and PCT Publication No. WO2004/058184).

The following methods may be used for adjusting the affinity of an antibody and for characterizing a CDR. One way of characterizing a CDR of an antibody and/or altering (such as improving) the binding affinity of a polypeptide, such as an antibody, termed "library scanning mutagenesis". Generally, library scanning mutagenesis works as follows. One or more amino acid positions in the CDR are replaced with two or more (such as 3, 4, 5, 6, 7, 8, 9, 10, 11, 12, 13, 14, 15, 16, 17, 18, 19, or 20) amino acids using art recognized methods. This generates small libraries of clones (in some embodiments, one for every amino acid position that is analyzed), each with a complexity of two or more members (if two or more amino acids are substituted at every position). Generally, the library also includes a clone comprising the native (unsubstituted) amino acid. A small number of clones, e.g., about 20-80 clones (depending on the complexity of the library), from each library are screened for binding affinity to the target polypeptide (or other binding target), and candidates with increased, the same, decreased, or no binding are identified. Methods for determining binding affinity are well-known in the art. Binding affinity may be determined using, for example, Biacore™ surface plasmon resonance analysis, which detects differences in binding affinity of about 2-fold or greater, Kinexa® Biosensor, scintillation proximity assays, ELISA, ORIGEN® immunoassay, fluorescence quenching, fluorescence transfer, and/or yeast display. Binding affinity may also be screened using a suitable bioassay. Biacore™ is particularly useful when the starting antibody already binds with a relatively high affinity, for example a $K_D$ of about 10 nM or lower.

In some embodiments, every amino acid position in a CDR is replaced (in some embodiments, one at a time) with all 20 natural amino acids using art recognized mutagenesis methods (some of which are described herein). This generates small libraries of clones (in some embodiments, one for every amino acid position that is analyzed), each with a complexity of 20 members (if all 20 amino acids are substituted at every position).

In some embodiments, the library to be screened comprises substitutions in two or more positions, which may be in the same CDR or in two or more CDRs. Thus, the library may comprise substitutions in two or more positions in one CDR. The library may comprise substitution in two or more positions in two or more CDRs. The library may comprise substitution in 3, 4, 5, or more positions, said positions found in two, three, four, five or six CDRs. The substitution may be prepared using low redundancy codons. See, e.g., Table 2 of Balint et al., 1993, Gene 137(1):109-18.

The CDR may be heavy chain variable region (VH) CDR3 and/or light chain variable region (VL) CDR3. The CDR may be one or more of VH CDR1, VH CDR2, VH CDR3, VL CDR1, VL CDR2, and/or VL CDR3. The CDR may be a Kabat CDR, a Chothia CDR, an extended CDR, an AbM CDR, a contact CDR, or a conformational CDR.

Candidates with improved binding may be sequenced, thereby identifying a CDR substitution mutant which results in improved affinity (also termed an "improved" substitution). Candidates that bind may also be sequenced, thereby identifying a CDR substitution which retains binding.

Multiple rounds of screening may be conducted. For example, candidates (each comprising an amino acid substitution at one or more position of one or more CDR) with improved binding are also useful for the design of a second library containing at least the original and substituted amino acid at each improved CDR position (i.e., amino acid position in the CDR at which a substitution mutant showed improved binding). Preparation, and screening or selection of this library is discussed further below.

Library scanning mutagenesis also provides a means for characterizing a CDR, in so far as the frequency of clones with improved binding, the same binding, decreased binding or no binding also provide information relating to the importance of each amino acid position for the stability of the antibody-antigen complex. For example, if a position of the CDR retains binding when changed to all 20 amino acids, that position is identified as a position that is unlikely to be required for antigen binding. Conversely, if a position of CDR retains binding in only a small percentage of substitutions, that position is identified as a position that is important to CDR function. Thus, the library scanning mutagenesis methods generate information regarding positions in the CDRs that can be changed to many different amino acids (including all 20 amino acids), and positions in the CDRs which cannot be changed or which can only be changed to a few amino acids.

Candidates with improved affinity may be combined in a second library, which includes the improved amino acid, the original amino acid at that position, and may further include additional substitutions at that position, depending on the complexity of the library that is desired, or permitted using the desired screening or selection method. In addition, if desired, adjacent amino acid position can be randomized to at least two or more amino acids. Randomization of adjacent amino acids may permit additional conformational flexibility in the mutant CDR, which may in turn, permit or facilitate the introduction of a larger number of improving mutations. The library may also comprise substitution at positions that did not show improved affinity in the first round of screening.

The second library is screened or selected for library members with improved and/or altered binding affinity using any method known in the art, including screening using Kinexa™ biosensor analysis, and selection using any method known in the art for selection, including phage display, yeast display, and ribosome display.

To express the anti-glucagon receptor antibodies of the present invention, DNA fragments encoding VH and VL regions can first be obtained using any of the methods described above. Various modifications, e.g. mutations, deletions, and/or additions can also be introduced into the DNA sequences using standard methods known to those of skill in the art. For example, mutagenesis can be carried out using standard methods, such as PCR-mediated mutagenesis, in which the mutated nucleotides are incorporated into the PCR primers such that the PCR product contains the desired mutations or site-directed mutagenesis.

The invention encompasses modifications to the variable regions shown in Table 1 and the CDRs shown in Tables 2A or 2B. For example, the invention includes antibodies comprising functionally equivalent variable regions and CDRs which do not significantly affect their properties as well as variants which have enhanced or decreased activity and/or affinity. For example, the amino acid sequence may be mutated to obtain an antibody with the desired binding affinity to glucagon receptor. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or which mature (enhance) the affinity of the polypeptide for its ligand, or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the half-life of the antibody in the blood circulation.

Substitution variants have at least one amino acid residue in the antibody molecule removed and a different residue inserted in its place. The sites of greatest interest for substitutional mutagenesis include the hypervariable regions, but framework alterations are also contemplated. Conservative substitutions are shown in Table 3 under the heading of "conservative substitutions." If such substitutions result in a change in biological activity, then more substantial changes, denominated "exemplary substitutions" in Table 3, or as further described below in reference to amino acid classes, may be introduced and the products screened.

TABLE 3

Amino Acid Substitutions

| Original Residue | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |

TABLE 3-continued

Amino Acid Substitutions

| Original Residue | Conservative Substitutions | Exemplary Substitutions |
|---|---|---|
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a β-sheet or helical conformation, (b) the charge or hydrophobicity of the molecule at the target site, or (c) the bulk of the side chain. Naturally occurring residues are divided into groups based on common side-chain properties:
 (1) Non-polar: Norleucine, Met, Ala, Val, Leu, Ile;
 (2) Polar without charge: Cys, Ser, Thr, Asn, Gln;
 (3) Acidic (negatively charged): Asp, Glu;
 (4) Basic (positively charged): Lys, Arg;
 (5) Residues that influence chain orientation: Gly, Pro; and
 (6) Aromatic: Trp, Tyr, Phe, His.

Non-conservative substitutions are made by exchanging a member of one of these classes for another class.

One type of substitution, for example, that may be made is to change one or more cysteines in the antibody, which may be chemically reactive, to another residue, such as, without limitation, alanine or serine. For example, there can be a substitution of a non-canonical cysteine. The substitution can be made in a CDR or framework region of a variable domain or in the constant region of an antibody. In some embodiments, the cysteine is canonical. Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

The antibodies may also be modified, e.g. in the variable domains of the heavy and/or light chains, e.g., to alter a binding property of the antibody. Changes in the variable region can alter binding affinity and/or specificity. In some embodiments, no more than one to five conservative amino acid substitutions are made within a CDR domain. In other embodiments, no more than one to three conservative amino acid substitutions are made within a CDR domain. For example, a mutation may be made in one or more of the CDR regions to increase or decrease the $K_D$ of the antibody for glucagon receptor, to increase or decrease $k_{off}$, or to alter the binding specificity of the antibody. Techniques in site-directed mutagenesis are well-known in the art. See, e.g., Sambrook et al. and Ausubel et al., supra.

A modification or mutation may also be made in a framework region or constant region to increase the half-life of an anti-glucagon receptor antibody. See, e.g., PCT Publication No. WO 00/09560. A mutation in a framework region or constant region can also be made to alter the immunogenicity of the antibody, to provide a site for covalent or non-covalent binding to another molecule, or to alter such properties as complement fixation, FcR binding and antibody-dependent cell-mediated cytotoxicity. In some embodiments, no more than one to five conservative amino acid substitutions are made within the framework region or constant region. In other embodiments, no more than one to three conservative amino acid substitutions are made within the framework region or constant region. According to the invention, a single antibody may have mutations in any one or more of the CDRs or framework regions of the variable domain or in the constant region.

Modifications also include glycosylated and nonglycosylated polypeptides, as well as polypeptides with other post-translational modifications, such as, for example, glycosylation with different sugars, acetylation, and phosphorylation. Antibodies are glycosylated at conserved positions in their constant regions (Jefferis and Lund, 1997, Chem. Immunol. 65:111-128; Wright and Morrison, 1997, TibTECH 15:26-32). The oligosaccharide side chains of the immunoglobulins affect the protein's function (Boyd et al., 1996, Mol. Immunol. 32:1311-1318; Wittwe and Howard, 1990, Biochem. 29:4175-4180) and the intramolecular interaction between portions of the glycoprotein, which can affect the conformation and presented three-dimensional surface of the glycoprotein (Jefferis and Lund, supra; Wyss and Wagner, 1996, Current Opin. Biotech. 7:409-416). Oligosaccharides may also serve to target a given glycoprotein to certain molecules based upon specific recognition structures. Glycosylation of antibodies has also been reported to affect antibody-dependent cellular cytotoxicity (ADCC). In particular, antibodies produced by CHO cells with tetracycline-regulated expression of β(1,4)-N-acetylglucosaminyltransferase III (GnTIII), a glycosyltransferase catalyzing formation of bisecting GlcNAc, was reported to have improved ADCC activity (Umana et al., 1999, Nature Biotech. 17:176-180).

Glycosylation of antibodies is typically either N-linked or O-linked. N-linked refers to the attachment of the carbohydrate moiety to the side chain of an asparagine residue. The tripeptide sequences asparagine-X-serine, asparagine-X-threonine, and asparagine-X-cysteine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The glycosylation pattern of antibodies may also be altered without altering the underlying nucleotide sequence. Glycosylation largely depends on the host cell used to express the antibody. Since the cell type used for expression of recombinant glycoproteins, e.g. antibodies, as potential therapeutics is rarely the native cell, variations in the glycosylation pattern of the antibodies can be expected (see, e.g. Hse et al., 1997, J. Biol. Chem. 272:9062-9070).

In addition to the choice of host cells, factors that affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261 and 5,278,299). Glycosylation, or certain types of glycosylation, can be enzymatically removed from the glycoprotein, for example, using endoglycosidase H (Endo H), N-glycosidase F, endoglycosidase F1, endoglycosidase F2, endoglycosidase F3. In addition, the recombinant host cell can be genetically engineered to be defective in processing certain types of polysaccharides. These and similar techniques are well known in the art.

Other methods of modification include using coupling techniques known in the art, including, but not limited to, enzymatic means, oxidative substitution and chelation. Modifications can be used, for example, for attachment of labels for immunoassay. Modified polypeptides are made using established procedures in the art and can be screened using standard assays known in the art, some of which are described below and in the Examples.

In some embodiments, the antibody comprises a modified constant region that has increased or decreased binding affinity to a human Fc gamma receptor, is immunologically inert or partially inert, e.g., does not trigger complement mediated lysis, does not stimulate antibody-dependent cell mediated cytotoxicity (ADCC), or does not activate microglia; or has reduced activities (compared to the unmodified antibody) in any one or more of the following: triggering complement mediated lysis, stimulating ADCC, or activating microglia. Different modifications of the constant region may be used to achieve optimal level and/or combination of effector functions. See, for example, Morgan et al., Immunology 86:319-324, 1995; Lund et al., J. Immunology 157:4963-9 157:4963-4969, 1996; Idusogie et al., J. Immunology 164:4178-4184, 2000; Tao et al., J. Immunology 143: 2595-2601, 1989; and Jefferis et al., Immunological Reviews 163:59-76, 1998. In some embodiments, the constant region is modified as described in Eur. J. Immunol., 1999, 29:2613-2624; PCT Application No. PCT/GB99/01441; and/or UK Patent Application No. 9809951.8.

In some embodiments, an antibody constant region can be modified to avoid interaction with Fc gamma receptor and the complement and immune systems. The techniques for preparation of such antibodies are described in WO 99/58572. For example, the constant region may be engineered to more resemble human constant regions to avoid immune response if the antibody is used in clinical trials and treatments in humans. See, e.g., U.S. Pat. Nos. 5,997,867 and 5,866,692.

In some embodiments, the Fc can be human $IgG_2$ or human $IgG_4$. The Fc can be human $IgG_2$ containing the mutation A330P331 to S330S331 ($IgG_{2\Delta a}$), in which the amino acid residues are numbered with reference to the wild type $IgG_2$ sequence. Eur. J. Immunol., 1999, 29:2613-2624. In some embodiments, the antibody comprises a constant region of $IgG_4$ comprising the following mutations (Armour et al., 2003, Molecular Immunology 40 585-593): E233F234L235 to P233V234A235 ($IgG_{4\Delta c}$), in which the numbering is with reference to wild type IgG4. In yet another embodiment, the Fc is human $IgG_4$ E233F234L235 to P233V234A235 with deletion G236 ($IgG_{4\Delta b}$). In another embodiment the Fc is any human $IgG_4$ Fc ($IgG_4$, $IgG_{4\Delta b}$ or $IgG_{4\Delta c}$) containing hinge stabilizing mutation S228 to P228 (Aalberse et al., 2002, Immunology 105, 9-19).

In still other embodiments, the constant region is aglycosylated for N-linked glycosylation. In some embodiments, the constant region is aglycosylated for N-linked glycosylation by mutating the oligosaccharide attachment residue and/or flanking residues that are part of the N-glycosylation recognition sequence in the constant region. For example, N-glycosylation site N297 may be mutated to, e.g., A, Q, K, or H. See, Tao et al., J. Immunology 143: 2595-2601, 1989; and Jefferis et al., Immunological Reviews 163:59-76, 1998. In some embodiments, the constant region is aglycosylated for N-linked glycosylation. The constant region may be aglycosylated for N-linked glycosylation enzymatically (such as removing carbohydrate by enzyme PNGase), or by expression in a glycosylation deficient host cell.

Other antibody modifications include antibodies that have been modified as described in PCT Publication No. WO 99/58572. These antibodies comprise, in addition to a binding domain directed at the target molecule, an effector domain having an amino acid sequence substantially homologous to all or part of a constant region of a human immunoglobulin heavy chain. These antibodies are capable of binding the target molecule without triggering significant complement dependent lysis, or cell-mediated destruction of the target. In some embodiments, the effector domain is capable of specifically binding FcRn and/or FcγRIIb. These are typically based on chimeric domains derived from two or more human immunoglobulin heavy chain CH2 domains. Antibodies modified in this manner are particularly suitable for use in chronic antibody therapy, to avoid inflammatory and other adverse reactions to conventional antibody therapy.

In some embodiments, the antibody comprises a modified constant region that has increased binding affinity for FcRn and/or an increased serum half-life as compared with the unmodified antibody.

In a process known as "germlining", certain amino acids in the VH and VL sequences can be mutated to match those found naturally in germline VH and VL sequences. In particular, the amino acid sequences of the framework regions in the VH and VL sequences can be mutated to match the germline sequences to reduce the risk of immunogenicity when the antibody is administered. Germline DNA sequences for human VH and VL genes are known in the art (see e.g., the "Vbase" human germline sequence database; see also Kabat, E. A., et al., 1991, Sequences of Proteins of Immunological Interest, Fifth Edition, U.S. Department of Health and Human Services, NIH Publication No. 91-3242; Tomlinson et al., 1992, J. Mol. Biol. 227:776-798; and Cox et al., 1994, Eur. J. Immunol. 24:827-836).

Another type of amino acid substitution that may be made is to remove potential proteolytic sites in the antibody. Such sites may occur in a CDR or framework region of a variable domain or in the constant region of an antibody. Substitution of cysteine residues and removal of proteolytic sites may decrease the risk of heterogeneity in the antibody product and thus increase its homogeneity. Another type of amino acid substitution is to eliminate asparagine-glycine pairs, which form potential deamidation sites, by altering one or both of the residues. In another example, the C-terminal lysine of the heavy chain of an anti-glucagon receptor antibody of the invention can be cleaved. In various embodiments of the invention, the heavy and light chains of the anti-glucagon receptor antibodies may optionally include a signal sequence.

Once DNA fragments encoding the VH and VL segments of the present invention are obtained, these DNA fragments can be further manipulated by standard recombinant DNA techniques, for example to convert the variable region genes to full-length antibody chain genes, to Fab fragment genes, or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an $IgG_1$, $IgG_2$, $IgG_3$, $IgG_4$, IgA, IgE, IgM or IgD constant region, but most preferably is an $IgG_1$ or $IgG_2$ constant region. The IgG constant region sequence can be any of the various alleles or allotypes known to occur among different individuals, such as Gm(1), Gm(2), Gm(3), and Gm(17). These allotypes represent naturally occurring amino acid substitution in the IgG1 constant regions. For a Fab fragment heavy chain gene, the VH-encoding DNA can be operatively linked to another DNA molecule encoding only the heavy chain CH1 constant region. The CH1 heavy chain constant region may be derived from any of the heavy chain genes.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region. The kappa constant region may be any of the various alleles known to occur among different individuals, such as Inv(1), Inv(2), and Inv(3). The lambda constant region may be derived from any of the three lambda genes.

To create a scFv gene, the VH- and VL-encoding DNA fragments are operatively linked to another fragment encoding a flexible linker such that the VH and VL sequences can be expressed as a contiguous single-chain protein, with the VL and VH regions joined by the flexible linker (See e.g., Bird et al., 1988, Science 242:423-426; Huston et al., 1988, Proc. Natl. Acad. Sci. USA 85:5879-5883; McCafferty et al., 1990, Nature 348:552-554. An example of a linking peptide is $(GGGGS)_3$ (SEQ ID NO: 18), which bridges approximately 3.5 nm between the carboxy terminus of one variable region and the amino terminus of the other variable region. Linkers of other sequences have been designed and used (Bird et al., 1988, supra). Linkers can in turn be modified for additional functions, such as attachment of drugs or attachment to solid supports. The single chain antibody may be monovalent, if only a single VH and VL are used, bivalent, if two VH and VL are used, or polyvalent, if more than two VH and VL are used. Bispecific or polyvalent antibodies may be generated that bind specifically to glucagon receptor and to another molecule. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as E. coli. Polynucleotides encoding the scFv of interest can be made by routine manipulations such as ligation of polynucleotides. The resultant scFv can be isolated using standard protein purification techniques known in the art.

Other forms of single chain antibodies, such as diabodies, are also encompassed. Diabodies are bivalent, bispecific antibodies in which VH and VL are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al., 1993, Proc. Natl. Acad. Sci. USA 90:6444-6448; Poljak, R. J., et al., 1994, Structure 2:1121-1123).

Heteroconjugate antibodies, comprising two covalently joined antibodies, are also within the scope of the invention. Such antibodies have been used to target immune system cells to unwanted cells (U.S. Pat. No. 4,676,980), and for treatment of HIV infection (PCT Publication Nos. WO 91/00360 and WO 92/200373; EP 03089). Heteroconjugate antibodies may be made using any convenient cross-linking methods. Suitable cross-linking agents and techniques are well known in the art, and are described in U.S. Pat. No. 4,676,980.

Chimeric or hybrid antibodies also may be prepared in vitro using known methods of synthetic protein chemistry, including those involving cross-linking agents. For example, immunotoxins may be constructed using a disulfide exchange reaction or by forming a thioether bond. Examples of suitable reagents for this purpose include iminothiolate and methyl-4-mercaptobutyrimidate.

The invention also encompasses fusion proteins comprising one or more fragments or regions from the antibodies disclosed herein. In some embodiments, a fusion antibody may be made that comprises all or a portion of an anti-glucagon receptor antibody of the invention linked to another polypeptide. In another embodiment, only the variable domains of the anti-glucagon receptor antibody are linked to the polypeptide. In another embodiment, the VH domain of an anti-glucagon receptor antibody is linked to a first polypeptide, while the VL domain of an anti-glucagon receptor antibody is linked to a second polypeptide that associates with the first polypeptide in a manner such that the VH and VL domains can interact with one another to form an antigen binding site. In another preferred embodiment, the VH domain is separated from the VL domain by a linker such that the VH and VL domains can interact with one another. The VH-linker-VL antibody is then linked to the polypeptide of interest. In addition, fusion antibodies can be created in which two (or more) single-chain antibodies are linked to one another. This is useful if one wants to create a divalent or polyvalent antibody on a single polypeptide chain, or if one wants to create a bispecific antibody.

In some embodiments, a fusion polypeptide is provided that comprises at least 10 contiguous amino acids of the variable light chain region shown in SEQ ID NO: 2, 4, 6, 8, 10 or 42 and/or at least 10 amino acids of the variable heavy chain region shown in SEQ ID NO: 3, 5, 7, 9, 11 or 43. In other embodiments, a fusion polypeptide is provided that comprises at least about 10, at least about 15, at least about 20, at least about 25, or at least about 30 contiguous amino acids of the variable light chain region and/or at least about 10, at least about 15, at least about 20, at least about 25, or at least about 30 contiguous amino acids of the variable heavy chain region. In another embodiment, the fusion polypeptide comprises a light chain variable region and/or a heavy chain variable region, as shown in any of the sequence pairs selected from among SEQ ID NOs: 2 and 3, 4 and 5, 6 and 7, 8 and 9, 10 and 11, and 42 and 43. In another embodiment, the fusion polypeptide comprises one or more CDR(s). In still other embodiments, the fusion polypeptide comprises VH CDR3 and/or VL CDR3. For purposes of this invention, a fusion protein contains one or more antibodies and another amino acid sequence to which it is not attached in the native molecule, for example, a heterologous sequence or a homologous sequence from another region. Exemplary heterologous sequences include, but are not limited to a "tag" such as a FLAG tag or a 6H is tag. Tags are well known in the art.

A fusion polypeptide can be created by methods known in the art, for example, synthetically or recombinantly. Typically, the fusion proteins of this invention are made by preparing and expressing a polynucleotide encoding them using recombinant methods described herein, although they may also be prepared by other means known in the art, including, for example, chemical synthesis.

In other embodiments, other modified antibodies may be prepared using anti-glucagon receptor antibody encoding nucleic acid molecules. For instance, "Kappa bodies" (Ill et al., 1997, Protein Eng. 10:949-57), "Minibodies" (Martin et al., 1994, EMBO J. 13:5303-9), "Diabodies" (Holliger et al., supra), or "Janusins" (Traunecker et al., 1991, EMBO J. 10:3655-3659 and Traunecker et al., 1992, Int. J. Cancer (Suppl.) 7:51-52) may be prepared using standard molecular biological techniques following the teachings of the specification.

For example, bispecific antibodies, monoclonal antibodies that have binding specificities for at least two different antigens, can be prepared using the antibodies disclosed herein. Methods for making bispecific antibodies are known in the art (see, e.g., Suresh et al., 1986, Methods in Enzymology 121: 210). For example, bispecific antibodies or antigen-binding fragments can be produced by fusion of hybridomas or linking of Fab' fragments. See, e.g., Songsivilai & Lachmann, 1990, Clin. Exp. Immunol. 79:315-321, Kostelny et al., 1992, J. Immunol. 148:1547-1553. Traditionally, the recombinant production of bispecific antibodies was based on the coexpression of two immunoglobulin heavy chain-light chain pairs, with the two heavy chains having different specificities (Millstein and Cuello, 1983, Nature 305, 537-539). In addition, bispecific antibodies may be formed as "diabodies" or "Janusins." In some embodiments, the bispecific antibody binds to two different epitopes of glucagon receptor. In some embodiments, the modified antibodies described above are prepared using one or more of the variable domains or CDR regions from an anti-glucagon receptor antibody provided herein.

According to one approach to making bispecific antibodies, antibody variable domains with the desired binding specificities (antibody-antigen combining sites) are fused to immunoglobulin constant region sequences. The fusion preferably is with an immunoglobulin heavy chain constant region, comprising at least part of the hinge, CH2 and CH3 regions. It is preferred to have the first heavy chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure, with an immunoglobulin light chain in only one half of the bispecific molecule, facilitates the separation of the desired bispecific compound from unwanted immunoglobulin chain combinations. This approach is described in PCT Publication No. WO 94/04690.

This invention also provides compositions comprising antibodies conjugated (for example, linked) to an agent that facilitate coupling to a solid support (such as biotin or avidin). For simplicity, reference will be made generally to antibodies with the understanding that these methods apply to any of the glucagon receptor binding and/or antagonist embodiments described herein. Conjugation generally refers to linking these components as described herein. The linking (which is generally fixing these components in proximate association at least for administration) can be achieved in any number of ways. For example, a direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

The antibodies can be bound to many different carriers. Carriers can be active and/or inert. Examples of well-known carriers include polypropylene, polystyrene, polyethylene, dextran, nylon, amylases, glass, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation. In some embodiments, the carrier comprises a moiety that targets the lung, heart, or heart valve.

An antibody or polypeptide of this invention may be linked to a labeling agent such as a fluorescent molecule, a radioactive molecule or any others labels known in the art. Labels are known in the art which generally provide (either directly or indirectly) a signal.

Polynucleotides, Vectors, and Host Cells

The invention also provides polynucleotides encoding any of the antibodies, including antibody fragments and modified antibodies described herein, such as, e.g., antibodies having impaired effector function. In another aspect, the invention provides a method of making any of the polynucleotides described herein. Polynucleotides can be made and expressed by procedures known in the art. Accordingly, the invention provides polynucleotides or compositions, including pharmaceutical compositions, comprising polynucleotides, encoding any of the following: the antibodies mAb1, mAb2, mAb3, mAb4, mAb5, mAb6, LM1, LM2, LM3, LM4, LM6, LM7, LM8, LM9, LM11, HM4, HM6, HM7, HM8, HM11, and HM12, or any fragment or part thereof having the ability to antagonize glucagon receptor.

Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an antibody or a fragment thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. Variants preferably exhibit at least about 70% identity, more preferably, at least about 80% identity, yet more preferably, at least about 90% identity, and most preferably, at least about 95% identity to a polynucleotide sequence that encodes a native antibody or a fragment thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned.

Optimal alignment of sequences for comparison may be conducted using the MegAlign® program in the Lasergene® suite of bioinformatics software (DNASTAR®, Inc., Madison, Wis.), using default parameters. This program embodies several alignment schemes described in the following references: Dayhoff, M. O., 1978, A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J., 1990, Unified Approach to Alignment and Phylogenes pp. 626-645 Methods in Enzymology vol. 183, Academic Press, Inc., San Diego, Calif.; Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy, Freeman Press, San Francisco, Calif.; Wilbur, W. J. and Lipman, D. J., 1983, Proc. Natl. Acad. Sci. USA 80:726-730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

Suitable "moderately stringent conditions" include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this invention can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, supra, for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp 18, mp 19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors are further provided. Expression vectors generally are replicable polynucleotide constructs that contain a polynucleotide according to the invention. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

The invention also provides host cells comprising any of the polynucleotides described herein. Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. See also PCT Publication No. WO 87/04462. Suitable non-mammalian host cells include prokaryotes (such as E. coli or B. subtillis) and yeast (such as S. cerevisae, S. pombe; or K. lactis). Preferably, the host cells express the cDNAs at a level of about 5 fold higher, more preferably, 10 fold higher, even more preferably, 20 fold higher than that of the corresponding endogenous antibody or protein of interest, if present, in the host cells. Screening the host cells for a specific binding to glucagon receptor or a glucagon receptor domain is effected by an immunoassay or FACS. A cell overexpressing the antibody or protein of interest can be identified.

An expression vector can be used to direct expression of an anti-glucagon receptor antagonist antibody. One skilled in the art is familiar with administration of expression vectors to obtain expression of an exogenous protein in vivo. See, e.g., U.S. Pat. Nos. 6,436,908; 6,413,942; and 6,376,471. Administration of expression vectors includes local or systemic administration, including injection, oral administration, particle gun or catheterized administration, and topical administration. In another embodiment, the expression vector is administered directly to the sympathetic trunk or ganglion, or into a coronary artery, atrium, ventrical, or pericardium.

Targeted delivery of therapeutic compositions containing an expression vector, or subgenomic polynucleotides can also be used. Receptor-mediated DNA delivery techniques are described in, for example, Findeis et al., Trends Biotechnol., 1993, 11:202; Chiou et al., Gene Therapeutics: Methods And Applications Of Direct Gene Transfer, J. A. Wolff, ed., 1994; Wu et al., J. Biol. Chem., 1988, 263:621; Wu et al., J. Biol. Chem., 1994, 269:542; Zenke et al., Proc. Natl. Acad. Sci. USA, 1990, 87:3655; Wu et al., J. Biol. Chem., 1991, 266: 338. Therapeutic compositions containing a polynucleotide are administered in a range of about 100 ng to about 200 mg of DNA for local administration in a gene therapy protocol. Concentration ranges of about 500 ng to about 50 mg, about 1 µg to about 2 mg, about 5 µg to about 500 µg, and about 20 µg to about 100 µg of DNA can also be used during a gene therapy protocol. The therapeutic polynucleotides and polypeptides can be delivered using gene delivery vehicles. The gene delivery vehicle can be of viral or non-viral origin (see generally, Jolly, Cancer Gene Therapy, 1994, 1:51; Kimura, Human Gene Therapy, 1994, 5:845; Connelly, Human Gene Therapy, 1995, 1:185; and Kaplitt, Nature Genetics, 1994, 6:148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther., 1992, 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther., 1992, 3:147); ligand-linked DNA (see, e.g., Wu, J. Biol. Chem., 1989, 264:16985); eukaryotic cell delivery vehicles cells (see, e.g., U.S. Pat. No.

5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP 0524968. Additional approaches are described in Philip, Mol. Cell. Biol., 1994, 14:2411, and in Woffendin, Proc. Natl. Acad. Sci., 1994, 91:1581.

Compositions

The invention also provides pharmaceutical compositions comprising an effective amount of an anti-glucagon receptor antibody described herein. Examples of such compositions, as well as how to formulate, are also described herein. In some embodiments, the composition comprises one or more glucagon receptor antibodies. In other embodiments, the anti-glucagon receptor antibody recognizes glucagon receptor. In other embodiments, the anti-glucagon receptor antibody is a human antibody. In other embodiments, the anti-glucagon receptor antibody is a humanized antibody. In some embodiments, the anti-glucagon receptor antibody comprises a constant region that is capable of triggering a desired immune response, such as antibody-mediated lysis or ADCC. In other embodiments, the anti-glucagon receptor antibody comprises a constant region that does not trigger an unwanted or undesirable immune response, such as antibody-mediated lysis or ADCC. In other embodiments, the anti-glucagon receptor antibody comprises one or more CDR(s) of the antibody (such as one, two, three, four, five, or, in some embodiments, all six CDRs).

It is understood that the compositions can comprise more than one anti-glucagon receptor antibody (e.g., a mixture of glucagon receptor antibodies that recognize different epitopes of glucagon receptor). Other exemplary compositions comprise more than one anti-glucagon receptor antibody that recognize the same epitope(s), or different species of anti-glucagon receptor antibodies that bind to different epitopes of glucagon receptor. In some embodiments, the compositions comprise a mixture of anti-glucagon receptor antibodies that recognize different variants of glucagon receptor.

The composition used in the present invention can further comprise pharmaceutically acceptable carriers, excipients, or stabilizers (Remington: The Science and practice of Pharmacy 20th Ed., 2000, Lippincott Williams and Wilkins, Ed. K. E. Hoover), in the form of lyophilized formulations or aqueous solutions. Acceptable carriers, excipients, or stabilizers are nontoxic to recipients at the dosages and concentrations, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEENT™, PLURONICS™ or polyethylene glycol (PEG). Pharmaceutically acceptable excipients are further described herein.

The anti-glucagon receptor antibody and compositions thereof can also be used in conjunction with other agents that serve to enhance and/or complement the effectiveness of the agents.

The invention also provides compositions, including pharmaceutical compositions, comprising any of the polynucleotides of the invention. In some embodiments, the composition comprises an expression vector comprising a polynucleotide encoding the antibody as described herein. In other embodiment, the composition comprises an expression vector comprising a polynucleotide encoding any of the antibodies described herein.

Kits

The invention also provides kits comprising any or all of the antibodies described herein. Kits of the invention include one or more containers comprising an anti-glucagon receptor antagonist antibody described herein and instructions for use in accordance with any of the methods of the invention described herein. Generally, these instructions comprise a description of administration of the anti-glucagon receptor antagonist antibody for the above described therapeutic treatments. In some embodiments, kits are provided for producing a single-dose administration unit. In certain embodiments, the kit can contain both a first container having a dried protein and a second container having an aqueous formulation. In certain embodiments, kits containing single and multi-chambered pre-filled syringes (e.g., liquid syringes and lyosyringes) are included.

In some embodiments, the antibody is a human antibody. In some embodiments, the antibody is a humanized antibody. In some embodiments, the antibody is a monoclonal antibody. The instructions relating to the use of an anti-glucagon receptor antibody generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an anti-glucagon receptor antibody. The container may further comprise a second pharmaceutically active agent.

Kits may optionally provide additional components such as buffers and interpretive information. Normally, the kit comprises a container and a label or package insert(s) on or associated with the container.

Biological Deposit

Representative materials of the present invention were deposited in the American Type Culture Collection, 10801

University Boulevard, Manassas, Va. 20110-2209, USA, on Jan. 29, 2013. Vector mAb5-LC having ATCC Accession No. PTA-120164 is a polynucleotide encoding the mAb5 light chain variable region, and vector mAb5-HC having ATCC Accession No. PTA-120165 is a polynucleotide encoding the mAb5 heavy chain variable region. The deposits were made under the provisions of the Budapest Treaty on the International Recognition of the Deposit of Microorganisms for the Purpose of Patent Procedure and Regulations thereunder (Budapest Treaty). This assures maintenance of a viable culture of the deposit for 30 years from the date of deposit. The deposit will be made available by ATCC under the terms of the Budapest Treaty, and subject to an agreement between Pfizer, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. Section 122 and the Commissioner's rules pursuant thereto (including 37 C.F.R. Section 1.14 with particular reference to 8860G 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The following examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

EXAMPLES

Example 1

Determining Antibody Kinetics and Binding Affinity

This Example illustrates the determination of antibody kinetics and binding affinities of anti-glucagon receptor antibodies to human and cynomolgus monkey (cyno) glucagon receptor.

An anti-human Fc sensor chip was prepared by activating all flow cells of a Biacore CM4 sensor chip with a 1:1 (v/v) mixture of 400 mM EDC and 100 mM NHS for 7 minutes, at a flow rate of 10 μL/min. Goat anti-human Fc antibody (Southern Biotech) was diluted to 50 μg/mL in 10 mM sodium acetate pH 5.0 and injected on all flow cells for 7 minutes at 20 μL/min. All flow cells were blocked with 100 mM ethylenediamine in 150 mM borate buffer pH 8.5 for 7 minutes at 10 μL/min. The running buffer for this immobilization procedure was 10 mM HEPES, 150 mM NaCl, 0.05% (v/v) TWEEN® 20, pH 7.4.

The following kinetics experiments were performed at 25° C. and 37° C. using a running buffer of 10 mM HEPES, 150 mM NaCl, 0.05% (v/v) TWEEN® 20, pH 7.4, 1 mg/mL BSA.

All experiments were performed on a Biacore™ T200 surface Plasmon resonance biosensor (GE Lifesciences, Piscataway N.J.). Human and cynomolgus monkey (cyno) glucagon receptor extracellular domain human Fc fusion proteins were captured onto downstream flow cells (flow cells 2, 3, respectively) at 2 μg/mL at a flow rate of 10 μL/min for 3 minutes. Flow cell 1 was used as a blank reference surface. Following capture of glucagon receptor Fc fusion proteins, analyte (buffer, or mAb5 Fab) was injected at 30 μL/min on all flow cells for two minutes. Multiple mAb5 Fab analyte concentrations were tested. The mAb5 Fab analyte concentrations were 0.16, 0.8, 4, 20 and 100 nM. After the analyte injection, dissociation was monitored for 10 minutes (for the 20 nM and 100 nM mAb5 Fab analyte samples) or 30 seconds (for the 0.16, 0.8, and 4 nM mAb5 Fab analyte samples). Dissociation was monitored for 30 seconds and 10 minutes for buffer analyte cycles. Following analyte binding and dissociation all flow cells were regenerated with four 1-minute injections of 75 mM phosphoric acid. The sensorgram data were double referenced prior to curve fitting (double referencing as described in Myszka, D. G., 1999, *J. Mol. Recognit.*, 12:279-284. The double referenced sensorgrams were fit globally to a simple 1:1 Langmuir with mass transport binding model using the Biacore™ T200 evaluation software. The binding affinity data for anti-glucagon receptor antagonist antibody mAb5 binding to human and cyno glucagon receptor are shown below in Table 4.

TABLE 4

| Receptor | 25° C. | | | | 37° C. | | | |
| --- | --- | --- | --- | --- | --- | --- | --- | --- |
| | $k_a$ (1/Ms) | $k_d$ (1/s) | $t_{1/2}$ (min) | $K_D$ (nM) | $k_a$ (1/Ms) | $k_d$ (1/s) | $t_{1/2}$ (min) | $K_D$ (nM) |
| Human glucagon receptor | $4.6 \times 10^5$ | $1.0 \times 10^{-4}$ | 116 | 0.22 | $6.5 \times 10^5$ | $4.9 \times 10^{-4}$ | 24 | 0.75 |
| Cyno glucagon receptor | $5.0 \times 10^5$ | $<8.5 \times 10^{-5}$* | >136 * | <0.17 * | $7.5 \times 10^5$ | $5.4 \times 10^{-4}$ | 21 | 0.72 |

* Dissociation rate was too low to determine a precise $k_d$ value under the given experimental conditions; therefore limits are reported for $k_d$, $t_{1/2}$ and $K_D$.

Example 2

Cell Based Functional Assay

This Example illustrates the effect of anti-glucagon receptor antagonist antibody mAb5 on glucagon signaling in cells expressing human glucagon receptor.

For this study, cAMP signaling was measured in a CHO cell line stably transfected with human glucagon receptor, using a LANCE® cAMP kit (cat# AD0262E, PerkinElmer Inc.). Cells were added to a 96-well plate and incubated with serially diluted mAb5. Cells were then stimulated with 200 pM glucagon (cat#22456, AnaSpec, Inc.) for 30 minutes at room temperature (RT). Detection antibody was then added and incubated for 10 minutes at RT. Cells were then lysed with supplied detection buffer and incubated in the dark for 3 hours at RT. The plate was then read on a VICTOR3™ plate reader (PerkinElmer, Inc). The results are shown in FIG. 1. As the readout of this assay is based on competition between a labeled, exogenous cAMP (measured at 665 nm) and unlabeled, endogenously generated cAMP, higher signals indicate less cAMP generated by the cells. mAb5 inhibits cAMP generation in a dose-dependent fashion (FIG. 1).

These results demonstrate that anti-glucagon receptor antagonist antibody mAb5 inhibits the glucagon receptor-mediated cAMP increase after glucagon stimulation.

Example 3

In Vivo Efficacy in Cynomolgus Monkey

This Example illustrates the effect of anti-glucagon receptor antagonist antibody on plasma glucose levels after glucagon challenge in cynomolgus monkeys.

Administration of an intravenous bolus of glucagon to animals leads to an elevation in plasma glucose as a result of glucagon signaling at the liver. To determine whether anti-glucagon receptor antagonist antibody inhibits this rise in plasma glucose, a glucagon challenge was performed in naïve, female, cynomolgus monkeys given either anti-glucagon receptor antagonist antibody or PBS. The glucagon challenge was performed in the monkeys on two separate occasions: one glucagon challenge was performed five days before the monkeys received either a single intravenous dose of mAb5 at 3 mg/kg or equivalent volume of PBS (baseline), and a second glucagon challenge was performed one hour after the monkeys received the mAb5 dose or PBS.

For each glucagon challenge, an intravenous bolus of 20 µg/kg glucagon (GlucaGen® Hypokits®) was administered at time 0. Blood samples were taken from all animals at the following timepoints: pre-challenge, and at 5, 15, 30, 45, 60 and 120 minutes post-challenge. Plasma samples were analyzed for plasma glucose concentrations using a clinical chemistry analyzer. Mean absolute glucose values (mg/dL)+/−SEM and AUC (area under the curve reflecting excursion in plasma glucose over time) are shown in Table 5.

(Table 5). In contrast, animals administered PBS one hour prior to glucagon challenge had a mean plasma glucose concentration of 84.5+/−4.36 pre-challenge, 109.0+/−6.98 mg/dL five minutes after challenge, 118.5+/−9.79 mg/dL fifteen minutes after challenge, 107.17+/−12.30 mg/dL thirty minutes after challenge, 98.33+/−12.08 mg/dL forty-five minutes after challenge, and 92.67+/−12.64 mg/dL sixty minutes after challenge (Table 5). Thus, after glucagon challenge, plasma glucose levels are substantially lower in animals treated with anti-glucagon receptor antagonist antibody Mab 5 compared to PBS control.

These results demonstrate that anti-glucagon receptor antagonist antibody effectively blocks glucose excursion after glucagon challenge.

Example 4

Liver Function Analysis after Treatment

This example illustrates the effect of chronic treatment with mAb5 glucagon receptor blocking mAb, at a high dose.

Previous clinical data in humans has demonstrated that 4-week treatment with a glucagon receptor small molecule antagonist can lead to elevations in certain liver functions tests (LFT's), specifically alanine aminotransferase (ALT) and aspartate aminotransferase (AST) (LY and MK). See, e.g., Engel, S., et al., 2011, "Efficacy and tolerability of MK0893, a glucagon receptor antagonist, in patients with type 2 diabetes," ADA Symposium. To address whether such changes would be evident following long term treatment where the glucagon receptor was blocked with a monoclonal antibody rather than a small molecule, a study was conducted to evaluate the effects on these LFT parameters of weekly, intravenous bolus doses of mAb5 in cynomolgus monkeys, over 4 weeks.

As shown above in Example 3, a single dose of 3 mg/kg mAb5 effectively inhibits glucose excursion after glucagon challenge in cynomolgus monkeys. For the liver function study, a dose of 100 mg/kg was chosen to ensure full blocking at all times. Three lean, naïve, female monkeys received 100 mg/kg mAb5 on days 1, 8, 15 and 22. As a control, three lean, naïve, female monkeys received an IV bolus of PBS control

TABLE 5

Mean plasma glucose concentration (mg/dL)

| Treatment Group | | Pre- | 5 | 15 | 30 | 45 | 60 | 120 | AUC |
|---|---|---|---|---|---|---|---|---|---|
| mAb5 3 mg/kg (n = 6) | Glucagon challenge (GC) at baseline | 83.67 +/− 3.13 | 106.50 +/− 3.91 | 115.67 +/− 5.04 | 102.17 +/− 3.97 | 91.0 +/− 4.29 | 89.17 +/− 4.01 | 85.67 +/− 6.08 | 11265 +/− 373.5 |
| | GC 1 hr post-mAb5 | 78.83 +/− 5.44 | 92.00 +/− 4.88 | 81.33 +/− 5.54 | 69.00 +/− 4.66 | 63.83 +/− 2.36 | 63.17 +/− 3.15 | 61.67 +/− 3.55 | 8115 +/− 316.8 |
| PBS control (n = 6) | GC at baseline | 89.17 +/− 8.24 | 135.33 +/− 11.31 | 140.0 +/− 10.45 | 100.67 +/− 11.46 | 83.67 +/− 5.875 | 81.00 +/− 4.90 | 65.33 +/− 3.40 | 11033 +/− 1042 |
| | GC 1 hr post-PBS | 84.5 +/− 4.36 | 109.0 +/− 6.98 | 118.5 +/− 9.79 | 107.17 +/− 12.30 | 98.33 +/− 12.08 | 92.67 +/− 12.64 | 65.50 +/− 5.03 | 10751 +/− 607.2 |

Figure 2:
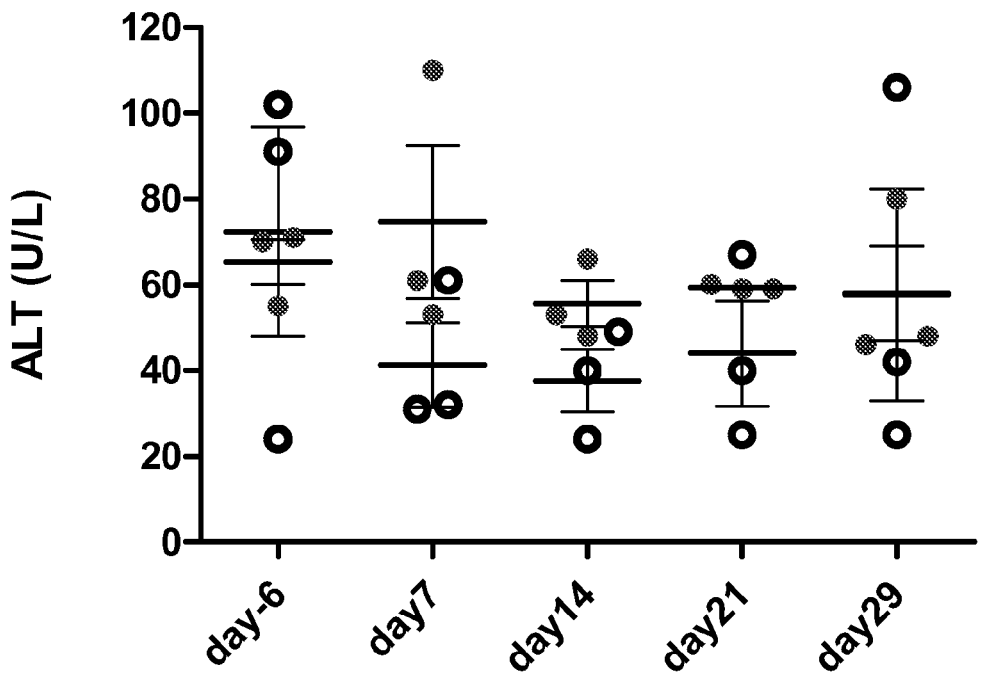
Figure 2:
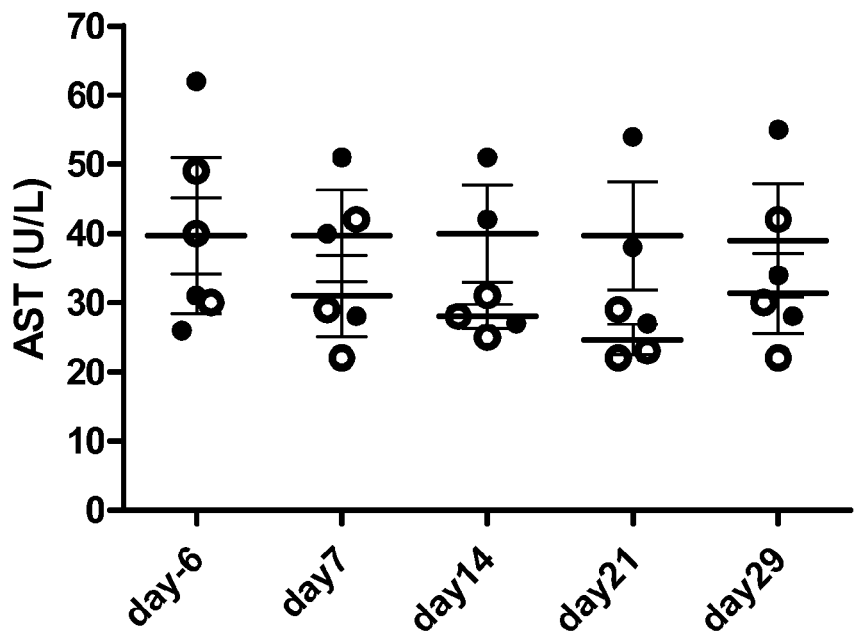
Figure 3:
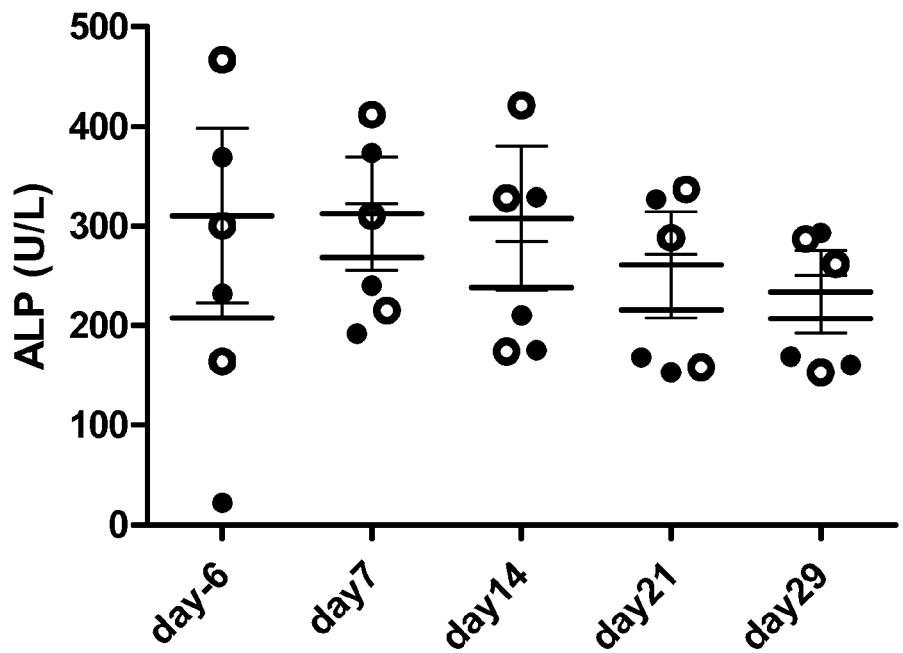
Figure 3:
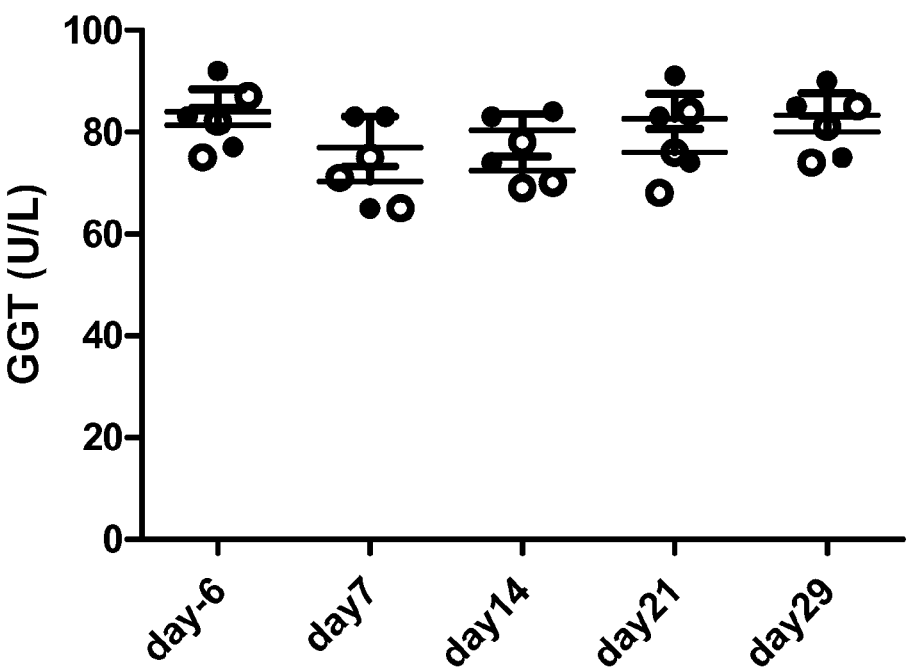

Animals treated with 3 mg/kg mAb5 one hour prior to glucagon challenge had a mean plasma glucose concentration of 78.83+/−5.44 pre-challenge, 92.00+/−4.88 mg/dL five minutes after challenge, 81.33+/−5.54 mg/dL fifteen minutes after challenge, 69.00+/−4.66 mg/dL thirty minutes after challenge, 63.83+/−2.36 mg/dL forty-five minutes after challenge, and 63.17+/−3.15 mg/dL sixty minutes after challenge on days 1, 8, 15 and 22. Fasting serum samples were collected from all animals, from both groups, on days 7, 14, 21 and 29 and compared against baseline, pre-treatment samples taken from the same animals before study-start (day −6). In addition to ALT and AST, alkaline phosphatase (ALP) and gamma-glutamyltransferase (GGT) were also measured, using a clinical chemistry analyzer. The ALT, AST ALP and GGT test results are shown in FIGS. 2 and 3, and summarized below in Table 6.

TABLE 6

|  | PBS control | | mAb5 100 mg/kg | |
| --- | --- | --- | --- | --- |
|  | Baseline | Day 29 | Baseline | Day 29 |
| ALT (U/L) | 65.3 +/− 5.17 | 58.0 +/− 11.02 | 72.3 +/− 24.38 | 57.7 +/− 24.66 |
| AST (U/L) | 39.7 +/− 11.26 | 39.0 +/− 8.19 | 39.7 +/− 5.48 | 31.3 +/− 5.93 |
| ALP (U/L) | 274.3 +/− 47.42 | 207.3 +/− 42.91 | 310.3 +/− 87.62 | 234.0 +/− 41.14 |
| GGT (U/L) | 84.0 +/− 4.36 | 83.3 +/− 4.41 | 81.3 +/− 3.48 | 80.0 +/− 3.22 |

Table 6 shows the mean (+/−SEM) values for these parameters at baseline (day −6) and at the end of study (day 29). As seen in Table 6, there were no significant changes in any of the LFT parameters measured in animals treated with mAb5 (last column) compared to the PBS control animals and baseline group animals.

These results demonstrate that chronic treatment with high dose mAb5 glucagon receptor blocking antibody is not deleterious to liver function.

Example 5

Circulating Lipid Level Analysis after Treatment

This example illustrates that chronic treatment with mAb5 glucagon receptor blocking mAb, at a high dose, does not elicit changes in plasma lipids in cynomolgus monkeys.

Previous clinical data in humans has demonstrated that 4-week treatment with a glucagon receptor small molecule antagonist was associated with dose-dependent, 10-17% elevations in LDL-cholesterol levels (MK). See, e.g., Ruddy, M. et al., 2011, "Inhibition of glucagon-induced hyperglycemia predicts glucose-lowering efficacy of the glucagon receptor antagonist, MK0893, in patients with type 2 diabetes mellitus (T2DM)," ADA Symposium. To address whether such changes would be evident following long term treatment where the glucagon receptor was blocked with a monoclonal antibody rather than a small molecule, a study was conducted to evaluate the effects on LDL-C and other circulating lipids (total cholesterol, HDL-C and triglycerides) after weekly, intravenous bolus doses of mAb5 in cynomolgus monkeys, over 4 weeks.

Three, lean, naïve, female monkeys received 100 mg/kg mAb5 on days 1, 8, 15 and 22. For a control, three, lean, naïve, female monkeys received an IV bolus of PBS control at the same time-points. Fasting serum samples were collected from all animals, from both groups, on days 7, 14, 21 and 29 and compared against baseline, pre-treatment samples (day −6) taken from the same animals before study-start, and lipids were measured using a clinical chemistry analyzer. The data from this study are summarized in Table 7 and shown in FIGS. 4 and 5.

Figure 4:
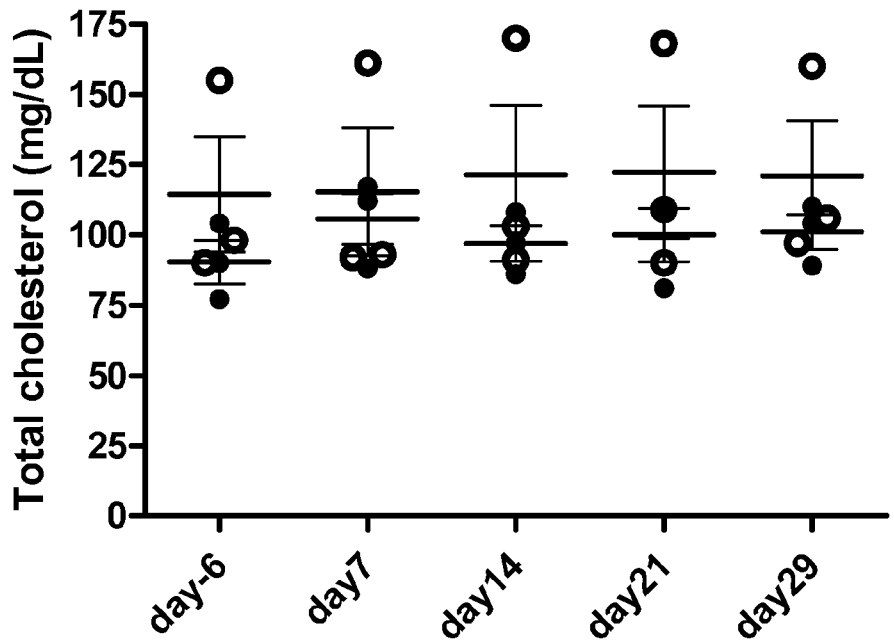
Figure 4:
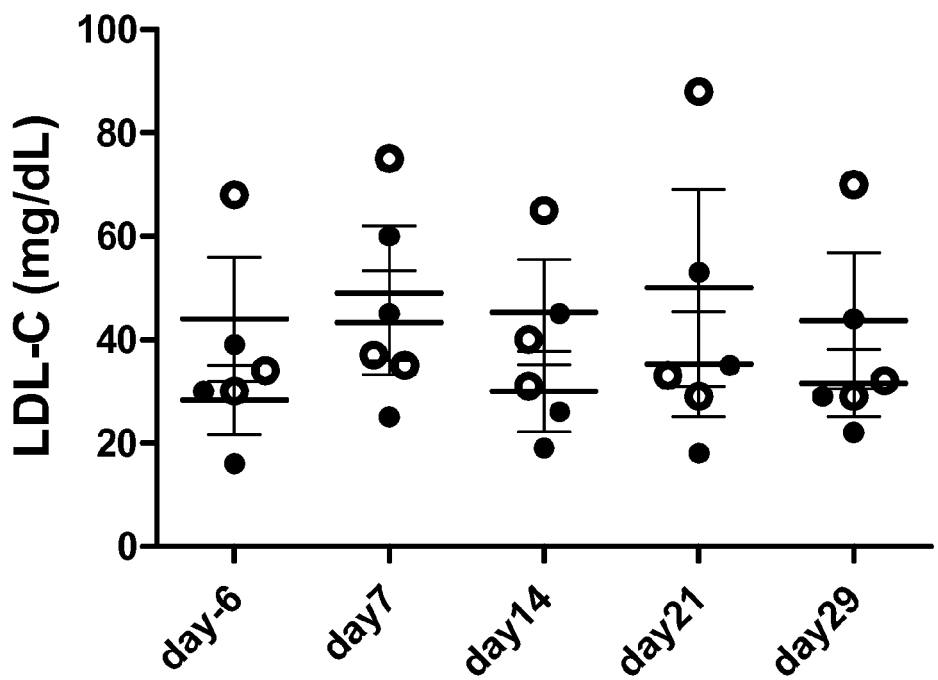
Figure 5:
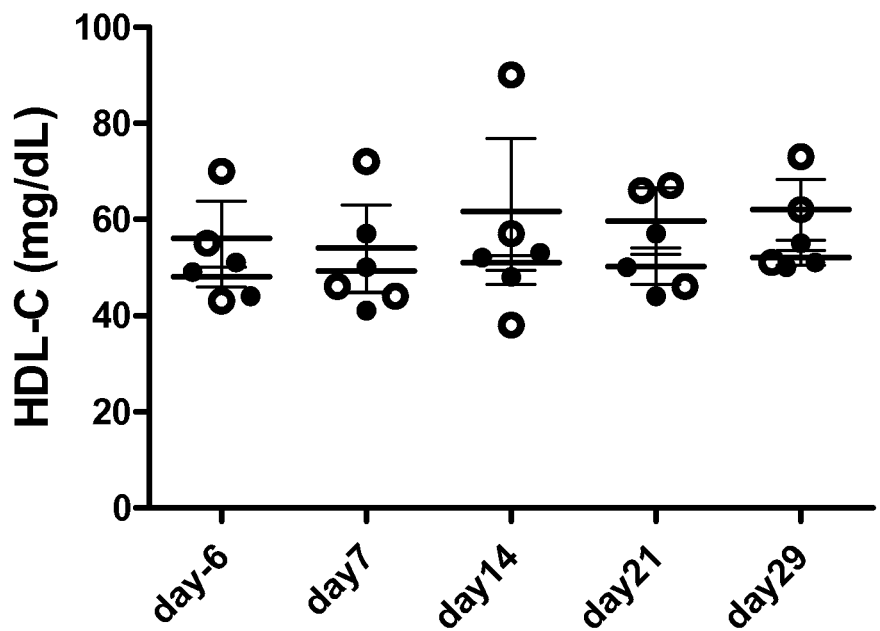
Figure 5:
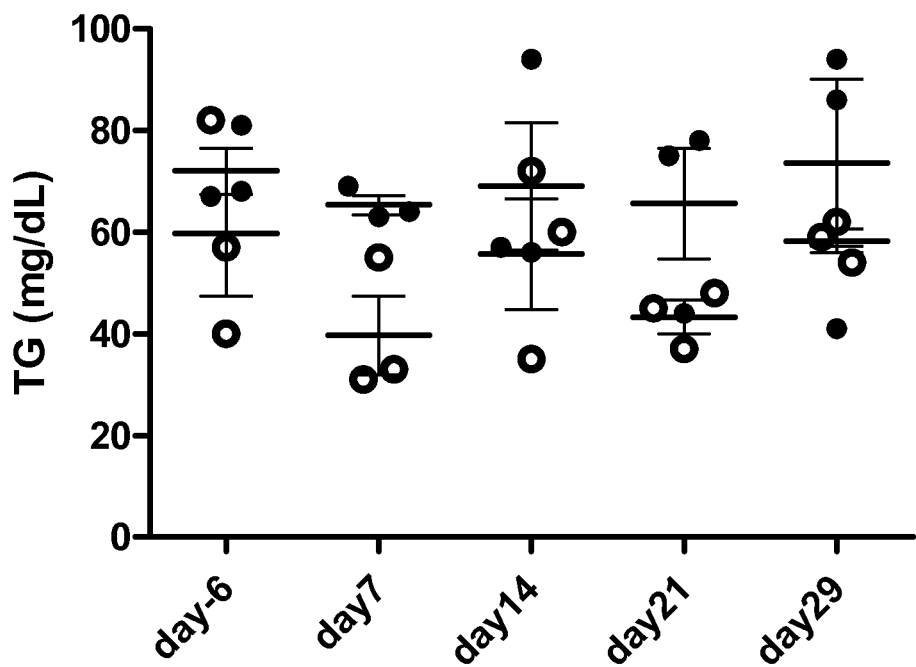

Table 7 shows the mean (+/−SEM) values for these parameters at baseline (day −6) and at the end of study (day 29). FIGS. 4 and 5 show the plasma lipid levels in the control and mAb5-treated animals at days −6, 7, 14, 21 and 29. No changes were observed in any of the circulating lipid parameters measured in the mAb5 treated animals, when compared to the PBS control animals and baseline group animals.

These results demonstrate that chronic treatment with high dose of mAb5 anti-glucagon receptor antagonist antibody is not associated with elevated LDL-cholesterol.

Example 6

In Vivo Efficacy in a Mouse Model of Type 2 Diabetes

This example illustrates treatment with an anti-glucagon receptor antagonist antibody in a mouse model of type 2 diabetes.

Administration of an intra-peritoneal bolus of glucose (glucose challenge) in fasted mice leads to a marked elevation, followed by a clearance period, in plasma glucose. Both the fasting plasma glucose levels, i.e., immediately prior to challenge, and the ability to handle the administered glucose load are impaired in high fat diet-fed, DIO (diet-induced obese) mice. Pre-treatment of these animals with an anti-glucagon receptor antagonist antibody, mAb3, was carried out as follows: starting from 6 weeks of age, C57Bl/6J mice (n=5 per group) were fed a high fat diet ("HFD", 40 kcal % fat). From 12 weeks of age, the mice continued on HFD and one group received a once weekly, intra-peritoneal injection of 3 mg/kg mAb3, while the second group received a similar volume of PBS vehicle. After 3 weeks of treatment, and following an 18 hour, overnight fast, an intra-peritoneal bolus of glucose (2 g/kg) was administered to all animals (time=0). Blood samples were taken from all animals at the following timepoints: pre-challenge, and at 15, 30, 45, 60, 90 and 120 minutes post-challenge. Whole blood samples were analyzed for plasma glucose concentrations using a hand-held One Touch® glucometer. Mean absolute glucose values (mg/dL)+/−SEM and AUC (area under the curve reflecting excursion in plasma glucose over time) are shown in Table 8.

TABLE 7

|  | PBS Control | | mAb5 100 mg/kg | |
| --- | --- | --- | --- | --- |
|  | Day −6 | Day 29 | Day −6 | Day 29 |
| Total cholesterol (mg/dL) | 90.3 +/− 7.79 | 101.0 +/− 6.25 | 114.3 +/− 20.46 | 121.0 +/− 19.67 |
| LDL-C (mg/dL) | 28.3 +/− 6.69 | 31.7 +/− 6.49 | 44.0 +/− 12.06 | 43.7 +/− 13.19 |
| HDL-C (mg/dL) | 48.0 +/− 2.08 | 52.0 +/− 1.53 | 56.0 +/− 7.81 | 62.0 +/− 6.35 |
| Triglycerides (mg/dL) | 72.0 +/− 4.51 | 73.7 +/− 16.49 | 59.7 +/− 12.20 | 58.3 +/− 2.33 |

TABLE 8

Mean Absolute Glucose Values (mg/dL)

| Group | Fasting, pre challenge | Time after glucose challenge (minutes) | | | | | | AUC |
|---|---|---|---|---|---|---|---|---|
| | | 15 | 30 | 45 | 60 | 90 | 120 | |
| mAb3 3 mg/kg | 128.80 +/− 12.92 | 426.00 +/− 33.90 | 327.80 +/− 20.65 | 287.00 +/− 20.82 | 280.20 +/− 18.72 | 255.60 +/− 17.93 | 184.20 +/− 10.94 | 33,313.8 +/− 1,542 |
| PBS | 156.80 +/− 11.41 | 549.60 +/− 15.59 | 594.20 +/− 5.31 | 548.00 +/− 18.17 | 536.00 +/− 21.46 | 411.40 +/− 24.39 | 313.40 +/− 20.88 | 55,656.2 +/− 1790 |

Animals treated with anti-glucagon receptor antagonist antibody mAb3 had a fasting blood glucose level of 128.80+/−12.92 mg/dL, significantly lower than the fasting blood glucose level in control animals given PBS, 156.80+/−11.41 mg/dL (Table 8, column 2). Furthermore, animals treated with mAb3 had lower blood glucose levels post-glucose challenge compared to animals given PBS (Table 8, columns 3-9). These results demonstrate that anti-glucagon receptor antagonist antibody reduces fasting blood glucose and excursion in plasma glucose elicited upon glucose challenge in a mouse model of type 2 diabetes.

Example 7

Combination Treatment

This example illustrates combination treatment with an anti-glucagon receptor antagonist antibody and an mTOR inhibitor in mice.

Blocking glucagon signaling in rodents has been previously demonstrated to cause a resultant increase in the number and/or size of pancreatic alpha (i.e., glucagon-producing) cells. See, e.g., Gelling et al., 2003, *Proc. Natl. Acad. Sci. USA* 100(3):1438-1443 (GCGR null mice); Sloop et al., 2004, *J. Clin. Invest.* 113(11): 1571-1581 (antisense oligonucleotids). Administration of anti-glucagon receptor antagonist antibody mAb3 (once weekly i.p.) in mice has similarly been shown to increase the area of alpha cells per islet, reflecting an increase in alpha cell number as well as an increase in average alpha cell size.

The present study was conducted to evaluate the effects of the mTOR inhibitor rapamycin as a co-treatment with mAb3. In this study, male, 14 week old, C57Bl/6J mice (n=10 per group) received either once weekly, intra-peritoneal injection of 3 mg/kg mAb3, or daily, intra-peritoneal dosing of 10 mg/kg rapamycin (formulated in 5% ethanol, 5.2% Tween-80, 5.2% PEG 400 in water), in combination with a once weekly 3 mg/kg dose of mAb3. A third group received vehicle as a control. After three weeks of treatment, the animals were sacrificed and their pancreata collected, fixed in 10% neutral buffered formalin for 24 hours, and then processed in paraffin wax and embedded following standard procedures. Sections were cut at 4 µm, mounted on plus slides and dried overnight at 37° C. Glucagon (to identify islet alpha cells) and insulin (to identify islet beta cells), were detected in the pancreas by immunohistochemistry using a sequential double labeling protocol on a Leica Bond™ automated immunostainer (Leica Microsystems, IL). Endogenous proteins were blocked with Cyto-Q Background Buster (Innovex Biosciences, CA). Antigen retrieval was performed for anti-glucagon immunohistochemistry using heat induced epitope retrieval (HIER) buffer at pH 6.0 (Leica Microsystems, IL) for 20 min. Anti-insulin (Dako, Calif.) were detected using biotinylated goat anti-guinea pig IgG (Dako, Calif.) with Bond™ Intense R Detection (Leica Microsystems) and anti-glucagon (Abcam, MA) were detected using Bond™ Polymer Refine Red Kit (Leica Microsystems, IL). Tissue was counterstained with hematoxylin (Leica Microsystems, IL), dehydrated and mounted in xylene before microscopic evaluations. Slides containing sections of pancreas IHC stained for anti-glucagon (vector red) and anti-insulin (DAB) were imaged at low (4×) and high power (20×) using a Perkin Elmer Vectra automated imaging system equipped with a multispectral camera. Both low and high power images were analyzed using Perkin Elmer®'s InForm® image analysis software. Detailed analysis of individual islets was carried out using high powered multispectral images. Images of each islet within a pancreas section were acquired in an automated fashion and analyzed with Perkin Elmer®'s InForm® software following spectral unmixing. Algorithms were created to quantify and characterize regions of alpha or beta cells using the anti-glucagon or anti-insulin staining respectively while excluding all irrelevant regions of the tissue. The number of nuclei within each region was also determined using the hematoxylin counter stain and used to calculate the average cell number and average cell size relative to the region (alpha/beta) of each islet.

The study data are summarized in Table 9 below. Provided in the table are: the number of alpha cells (quantified as % alpha cell number/islet+/−SEM), the overall area occupied by alpha cells (quantified as % alpha cell area/islet+/−SEM), and average alpha cell size (measured as pixels).

TABLE 9

| Treatment group | % alpha cell number/islet | % alpha cell area/islet | Average alpha cell size (pixels) |
|---|---|---|---|
| Vehicle | 32.71 +/− 1.91 | 28.255 +/− 1.75 | 522.51 +/− 20.59 |
| mAb3, 3 mg/kg weekly | 47.785 +/− 2.23 | 45.57 +/− 2.43 | 647.34 +/− 15.62 |
| Rapamycin, 10 mg/kg daily + mAb3, 3 mg/kg weekly | 35.37 +/− 2.85 | 31.72 +/− 2.64 | 539.13 +/− 24.34 |

Increased alpha cell number and alpha cell size were observed in the mice treated with mAb3, compared to mice administered vehicle only (Table 9). These measures of increased alpha cell number and size were absent when mAb3 was co-administered with rapamycin treatment (Table 9). These data demonstrate that mTOR signaling may play a role in mediating the alpha cell hyperplasia. These data also demonstrate that co-treatment with an mTOR inhibitor reduces hypertrophy and hyperplasia elicited by blocking glucagon receptor activity.

Example 8

Liver Function Analysis

This example illustrates the effect of four-week treatment with anti-glucagon receptor antagonist antibody on liver function.

It has been previously shown that 4-week treatment with a glucagon receptor small molecule antagonist can lead to elevations in certain liver functions tests (LFT's), specifically alanine aminotransferase (ALT) and aspartate aminotransferase (AST) (LY and MK). See, e.g., Engel, S., et al., 2011, "Efficacy and tolerability of MK0893, a glucagon receptor antagonist, in patients with type 2 diabetes," ADA Symposium. To address whether such changes would be evident following long term treatment where the glucagon receptor was blocked with a monoclonal antibody rather than a small molecule, a study was conducted to evaluate the effects on these LFT parameters of weekly, intraperitoneal doses of anti-glucagon receptor antagonist antibody in wild-type and high fat diet-fed (HFD), DIO (diet-induced obese) mice, over 4 weeks. In the study, wild-type and HFD-DIO mice were administered either anti-glucagon receptor antagonist antibody mAb3 or PBS vehicle (control) at a dose of 10 mg/kg i.p. on a weekly basis. The 10 mg/kg dose used has been shown to exert maximal glucose lowering effect for a duration of at least seven days (i.e., the dosing interval), suggesting that the glucagon receptor is fully blocked in this study. After 4 weeks of mAb3 treatment, fasting serum samples were collected and levels of the following liver enzymes were measured: ALT, AST, and ALP. The results (mean and standard error per group (n=10/group/mouse model)) are summarized below in Table 10.

TABLE 10

| Mouse model | PBS vehicle (control) | | 10 mg/kg mAb3 | |
|---|---|---|---|---|
| | Mean | SEM | Mean | SEM |
| ALT (U/L) | | | | |
| Wild-type | 31.50 | 1.64 | 27.70 | 1.57 |
| HFD-DIO | 223.00 | 67.85 | 191.90 | 24.91 |
| ALP (U/L) | | | | |
| Wild-type | 72.10 | 3.14 | 81.80 | 3.26 |
| HFD-DIO | 61.30 | 3.29 | 56.20 | 2.40 |

TABLE 10-continued

| Mouse model | PBS vehicle (control) | | 10 mg/kg mAb3 | |
|---|---|---|---|---|
| | Mean | SEM | Mean | SEM |
| AST (U/L) | | | | |
| Wild-type | 144.30 | 24.24 | 159.00 | 21.32 |
| HFD-DIO | 226.20 | 51.57 | 128.70 | 9.59 |

There were no significant changes in any of the LFT parameters (i.e., ALT, ALP and AST levels) measured in animals treated with mAb3 in comparison to the LFT parameters measured in the PBS vehicle control animals (Table 10).

These results demonstrate that four-week treatment with anti-glucagon receptor antagonist antibody is not deleterious to liver function.

Example 9

Liver Function Analysis

This example illustrates the effect of 43-week treatment with anti-glucagon receptor antagonist antibody on liver function.

In this study, wild-type C57Bl/6 male mice were exposed to long-term treatment with anti-glucagon receptor antagonist antibody mAb3, starting at 9 weeks of age and continuing for 43 weeks, until 52 weeks of age (n=9). A 3 mg/kg dose of mAb3 was administered i.p. weekly. PBS vehicle was administered to a group of control animals (n=6). At termination of the study, fasting serum samples were collected and levels of the following liver enzymes were measured: ALT, AST, and ALP. Results (mean and standard error per group) are summarized in Table 11.

TABLE 11

| ALT (U/L) | | | | AST (U/L) | | | | ALP (U/L) | | | |
|---|---|---|---|---|---|---|---|---|---|---|---|
| PBS vehicle (control) | | 3 mg/kg mAb3 | | PBS vehicle (control) | | 3 mg/kg mAb3 | | PBS vehicle (control) | | 3 mg/kg mAb3 | |
| Mean | SEM | Mean | SEM | Mean | SEM | Mean | SEM | Mean | SEM | Mean | SEM |
| 43.50 | 9.52 | 49.78 | 6.30 | 61.00 | 10.07 | 54.33 | 5.80 | 63.17 | 3.25 | 63.67 | 2.66 |

There was no significant change in any of the LFT parameters (i.e., ALT, ALP and AST levels) measured in mice treated with mAb3 when compared to LFT parameters measured in control mice dosed with PBS over the same duration (Table 11). Thus, treatment with mAb3 glucagon receptor blocking antibody, for a duration of approximately 11 months, which represents a significant portion of the total lifespan of this animal, was not associated with any deleterious effects on these enzyme markers of liver function.

These results demonstrate that long-term treatment with anti-glucagon receptor antagonist antibody is not deleterious to liver function.

Example 10

Liver Function Analysis

This example illustrates the effect of chronic treatment with anti-glucagon receptor antagonist antibody.

A study was conducted to address the effects of 13 week-long treatment with anti-glucagon receptor antagonist antibody mAb5 on liver function. In the study, male and female cynomolgus monkeys were administered mAb5 either subcutaneously (SC) or intravenously (IV), over 13 weeks.

A single dose of 3 mg/kg mAb5 effectively inhibits glucose excursion after glucagon challenge in cynomolgus monkeys (see, Example 3 above). Doses chosen for this chronic study were 10, 50 and 200 mg/kg, each of which would be expected to produce full blockade of the glucagon signal.

Four cohorts of lean, naïve monkeys (each n=3 of each gender) received 10 mg/kg mAb5 weekly by IV or SC injection for a total of 13 weeks. A further six cohorts of five lean, naïve monkeys of each gender, each received 50 mg/kg mAb5 weekly by IV injection or 200 mg/kg mAb5 weekly by IV or SC injection for a total of 13 weeks. As a control, five lean, naïve, monkeys of each gender received weekly injections of vehicle by either the IV or SC injection routes for 13 weeks.

Fasting serum samples were collected from all animals on days 29, 57 and 93, and compared to two baseline, pre-treatment samples taken from the same animals before study-start (i.e., days −43 and −8). In addition to ALT and AST, alkaline phosphatase (ALP) and gamma-glutamyltransferase (GGT) were also measured, using a clinical chemistry analyzer. The ALT, AST ALP and GGT test results (mean+/−SEM) are summarized below in Table 12.

TABLE 12

| Dose group mAb5 (mg/kg) | Treatment duration (days) | ALT (U/L) | AST (U/L) | ALP (U/L) | GGT (U/L) |
|---|---|---|---|---|---|
| Female vehicle | −43 | 99.6 | 31.6 | 322.4 | 81.8 |
|  |  | 7.0 | 1.7 | 17.4 | 5.0 |
|  | −8 | 53.0 | 28.2 | 296.6 | 79.2 |
|  |  | 3.6 | 2.0 | 23.7 | 2.8 |
|  | 29 | 70.8 | 33.2 | 309.0 | 97.2 |
|  |  | 11.4 | 1.5 | 24.0 | 4.9 |
|  | 57 | 58.4 | 31.2 | 301.8 | 98.0 |
|  |  | 2.7 | 3.0 | 28.7 | 6.4 |
|  | 93 | 60.8 | 39.4 | 309.8 | 94.2 |
|  |  | 4.3 | 1.7 | 26.3 | 6.1 |
| Female 10 mg/kg IV | −43 | 80.0 | 39.3 | 325.0 | 97.7 |
|  |  | 19.2 | 1.9 | 19.7 | 6.2 |
|  | −8 | 37.0 | 39.7 | 283.3 | 95.3 |
|  |  | 3.2 | 7.3 | 44.7 | 13.9 |
|  | 29 | 62.7 | 37.0 | 271.0 | 98.0 |
|  |  | 20.2 | 1.7 | 53.1 | 9.8 |
|  | 57 | 43.3 | 36.3 | 299.3 | 116.7 |
|  |  | 14.2 | 1.2 | 37.9 | 12.6 |
|  | 93 | 53.7 | 46.0 | 285.0 | 102.3 |
|  |  | 24.8 | 2.0 | 45.2 | 10.9 |
| Female 10 mg/kg SC | −43 | 84.7 | 41.0 | 287.0 | 65.3 |
|  |  | 19.4 | 6.5 | 42.2 | 0.7 |
|  | −8 | 74.3 | 38.7 | 259.7 | 68.0 |
|  |  | 12.3 | 2.3 | 35.3 | 4.4 |
|  | 29 | 87.7 | 50.7 | 270.7 | 72.0 |
|  |  | 17.3 | 6.1 | 22.6 | 1.5 |
|  | 57 | 60.3 | 48.3 | 248.0 | 71.7 |
|  |  | 5.7 | 4.6 | 23.8 | 1.5 |
|  | 93 | 62.3 | 53.0 | 236.0 | 68.3 |
|  |  | 12.4 | 8.5 | 24.1 | 1.2 |
| Female 50 mg/kg IV | −43 | 134.2 | 41.6 | 328.2 | 83.0 |
|  |  | 29.2 | 4.0 | 16.7 | 6.5 |
|  | −8 | 78.0 | 39.8 | 265.0 | 78.2 |
|  |  | 26.8 | 5.3 | 8.3 | 4.2 |
|  | 29 | 73.8 | 39.2 | 240.8 | 77.4 |
|  |  | 17.4 | 5.7 | 19.1 | 4.2 |
|  | 57 | 58.6 | 34.8 | 239.2 | 88.2 |
|  |  | 5.9 | 2.1 | 14.1 | 6.4 |
|  | 93 | 73.2 | 50.8 | 260.4 | 82.8 |
|  |  | 8.8 | 10.1 | 33.4 | 7.8 |
| Female 200 mg/kg IV | −43 | 99.4 | 36.8 | 353.2 | 93.0 |
|  |  | 9.4 | 1.9 | 66.1 | 11.5 |
|  | −8 | 77.6 | 31.4 | 328.0 | 86.8 |
|  |  | 23.9 | 2.2 | 68.0 | 13.6 |
|  | 29 | 65.0 | 35.6 | 274.6 | 89.2 |
|  |  | 4.3 | 5.8 | 31.5 | 10.3 |

TABLE 12-continued

| Dose group mAb5 (mg/kg) | Treatment duration (days) | ALT (U/L) | AST (U/L) | ALP (U/L) | GGT (U/L) |
|---|---|---|---|---|---|
|  | 57 | 68.4 | 31.8 | 298.6 | 97.0 |
|  |  | 7.2 | 2.9 | 46.9 | 10.0 |
|  | 93 | 87.8 | 46.6 | 263.2 | 85.0 |
|  |  | 9.8 | 6.2 | 38.1 | 7.4 |
| Female 200 mg/kg SC | −43 | 102.4 | 39.2 | 314.6 | 83.0 |
|  |  | 22.7 | 5.9 | 15.9 | 7.6 |
|  | −8 | 72.4 | 38.2 | 274.4 | 81.8 |
|  |  | 20.3 | 5.4 | 20.7 | 6.4 |
|  | 29 | 65.0 | 39.0 | 271.2 | 79.6 |
|  |  | 18.5 | 4.1 | 40.2 | 8.4 |
|  | 57 | 57.2 | 32.2 | 255.8 | 88.2 |
|  |  | 16.0 | 3.5 | 28.8 | 6.6 |
|  | 93 | 71.6 | 44.8 | 285.6 | 87.2 |
|  |  | 16.8 | 6.4 | 42.1 | 8.6 |
| Male vehicle | −43 | 67.0 | 45.8 | 729.2 | 160.2 |
|  |  | 12.4 | 4.1 | 50.9 | 15.7 |
|  | −8 | 32.2 | 37.6 | 684.4 | 165.6 |
|  |  | 2.8 | 3.3 | 65.4 | 14.8 |
|  | 29 | 44.8 | 42.4 | 743.6 | 212.4 |
|  |  | 4.2 | 3.3 | 47.8 | 31.1 |
|  | 57 | 38.0 | 40.6 | 788.6 | 214.6 |
|  |  | 4.4 | 4.5 | 77.3 | 18.5 |
|  | 93 | 56.8 | 53.2 | 768.6 | 187.6 |
|  |  | 7.3 | 4.0 | 36.0 | 14.6 |
| Male 10 mg/kg IV | −43 | 92.0 | 51.0 | 618.0 | 130.7 |
|  |  | 53.1 | 13.7 | 23.6 | 9.9 |
|  | −8 | 48.0 | 42.7 | 638.0 | 155.0 |
|  |  | 22.0 | 8.8 | 15.3 | 15.4 |
|  | 29 | 74.7 | 45.3 | 638.0 | 149.3 |
|  |  | 43.2 | 13.0 | 31.7 | 5.2 |
|  | 57 | 49.7 | 35.7 | 676.7 | 170.0 |
|  |  | 17.6 | 5.2 | 106.0 | 5.0 |
|  | 93 | 51.3 | 49.0 | 678.7 | 150.0 |
|  |  | 16.4 | 4.6 | 106.1 | 3.0 |
| Male 10 mg/kg SC | −43 | 72.0 | 51.7 | 584.0 | 125.3 |
|  |  | 12.8 | 9.2 | 109.6 | 12.2 |
|  | −8 | 34.7 | 34.0 | 556.7 | 135.0 |
|  |  | 6.7 | 2.6 | 86.5 | 13.7 |
|  | 29 | 51.7 | 41.7 | 595.3 | 130.3 |
|  |  | 3.5 | 3.0 | 118.4 | 12.3 |
|  | 57 | 40.7 | 38.0 | 571.7 | 152.7 |
|  |  | 5.4 | 4.6 | 96.1 | 13.9 |
|  | 93 | 64.3 | 64.7 | 574.3 | 141.0 |
|  |  | 15.9 | 19.2 | 106.8 | 17.5 |
| Male 50 mg/kg SC | −43 | 67.4 | 45.6 | 730.0 | 173.2 |
|  |  | 12.1 | 3.4 | 87.3 | 9.5 |
|  | −8 | 40.6 | 39.4 | 782.4 | 190.8 |
|  |  | 4.5 | 1.7 | 88.0 | 14.3 |
|  | 29 | 46.0 | 39.6 | 696.4 | 178.4 |
|  |  | 9.2 | 1.9 | 94.5 | 18.4 |
|  | 57 | 39.8 | 36.0 | 712.6 | 186.8 |
|  |  | 7.8 | 2.0 | 101.7 | 21.9 |
|  | 93 | 44.8 | 46.8 | 611.4 | 161.3 |
|  |  | 15.2 | 13.7 | 172.5 | 17.1 |
| Male 200 mg/kg IV | −43 | 59.8 | 40.6 | 511.8 | 134.2 |
|  |  | 17.0 | 5.7 | 37.5 | 11.8 |
|  | −8 | 36.2 | 38.2 | 566.4 | 168.8 |
|  |  | 6.5 | 5.5 | 39.8 | 18.3 |
|  | 29 | 51.8 | 36.4 | 504.0 | 147.2 |
|  |  | 17.0 | 3.8 | 30.2 | 16.4 |
|  | 57 | 43.0 | 35.2 | 537.0 | 158.2 |
|  |  | 6.4 | 3.1 | 46.2 | 17.7 |
|  | 93 | 49.4 | 44.8 | 526.2 | 142.4 |
|  |  | 7.4 | 7.2 | 54.2 | 16.8 |
| Male 200 mg/kg SC | −43 | 48.2 | 37.8 | 584.2 | 158.2 |
|  |  | 6.1 | 3.6 | 43.4 | 16.5 |
|  | −8 | 36.8 | 31.0 | 605.2 | 184.2 |
|  |  | 4.7 | 0.8 | 24.7 | 22.1 |
|  | 29 | 44.8 | 33.6 | 521.2 | 155.0 |
|  |  | 5.9 | 3.5 | 40.5 | 17.3 |
|  | 57 | 44.8 | 36.0 | 600.6 | 190.2 |
|  |  | 5.6 | 2.3 | 57.6 | 16.1 |
|  | 93 | 57.6 | 42.6 | 576.4 | 175.0 |
|  |  | 8.0 | 4.5 | 43.1 | 13.8 |

Table 12 shows the mean (+/−SEM) values for ALT, AST ALP and GGT levels at baseline (days −43 and −8) and at monthly intervals throughout the dosing schedule (days 29, 57 and 93). There were no significant changes in any of the LFT parameters measured in animals treated with mAb5 at any dose level/dose route, compared to vehicle-treated control animals and each group's own baseline values (Table 12).

These results demonstrate that chronic treatment with high dose mAb5 glucagon receptor blocking antibody is not deleterious to liver function.

Example 11

Circulating Lipid Level Analysis

This example illustrates the effect of chronic, long term treatment with mAb5 glucagon receptor antagonist antibody.

To evaluate the effects of blocking the glucagon receptor with a monoclonal antibody, male and female cynomolgus monkeys were administered weekly doses of mAb5, for 13 weeks and assessed for effects on circulating lipids (total cholesterol, LDL-C, HDL-C and triglycerides).

Four cohorts of lean, naïve monkeys, each comprising three animals of each gender received 10 mg/kg mAb5 weekly by IV or SC injection for a total of 13 weeks. A further six cohorts of five lean, naïve monkeys of each gender, each received 50 mg/kg mAb5 weekly by IV injection or 200 mg/kg mAb5 weekly by IV or SC injection for a total of 13 weeks. As a control, five lean, naïve, monkeys of each gender received weekly injections of vehicle (by both the IV and SC routes) for 13 weeks.

Fasting serum samples were collected (approximately monthly) from all animals on days 29, 57 and 93, and compared against two baseline, pre-treatment samples taken from the same animals before study-start (days −43 and −8). In addition to ALT and AST, alkaline phosphatase (ALP) and gamma-glutamyltransferase (GGT) were also measured, using a clinical chemistry analyzer. The data from this study (mean+/−SEM) are summarized in Table 13.

TABLE 13

| Dose group mAb5 (mg/kg) | Treatment duration (days) | Total cholesterol (mg/dL) | LDL-C (mg/dL) | HDL-C (mg/dL) | TG (mg/dL) |
|---|---|---|---|---|---|
| Female vehicle | −43 | 100.0 | 56.4 | 54.4 | 46.0 |
| | | 7.2 | 4.2 | 5.4 | 6.2 |
| | −8 | 98.8 | 47.0 | 56.4 | 50.2 |
| | | 8.6 | 4.7 | 4.6 | 9.8 |
| | 29 | 105.8 | 45.6 | 56.0 | 50.6 |
| | | 7.4 | 3.3 | 3.6 | 6.2 |
| | 57 | 114.0 | 46.2 | 63.8 | 46.2 |
| | | 9.6 | 4.9 | 5.1 | 6.8 |
| | 93 | 111.0 | 46.0 | 57.8 | 43.0 |
| | | 7.7 | 3.6 | 4.9 | 6.0 |
| Female 10 mg/kg IV | −43 | 122.3 | 77.7 | 58.3 | 71.0 |
| | | 9.6 | 5.2 | 5.8 | 5.1 |
| | −8 | 122.3 | 64.7 | 64.0 | 73.0 |
| | | 3.9 | 4.1 | 2.9 | 7.0 |
| | 29 | 133.7 | 71.7 | 60.7 | 68.7 |
| | | 11.8 | 3.8 | 5.6 | 10.7 |
| | 57 | 142.7 | 69.7 | 68.0 | 64.0 |
| | | 11.6 | 3.2 | 7.2 | 9.2 |
| | 93 | 153.7 | 79.7 | 55.7 | 77.7 |
| | | 8.5 | 2.9 | 2.2 | 6.8 |
| Female 10 mg/kg SC | −43 | 82.3 | 41.3 | 50.7 | 41.3 |
| | | 4.2 | 1.7 | 3.8 | 1.8 |
| | −8 | 86.3 | 38.7 | 51.7 | 40.0 |
| | | 4.8 | 1.9 | 4.2 | 8.2 |
| | 29 | 106.0 | 46.7 | 56.7 | 54.3 |
| | | 3.2 | 0.9 | 5.8 | 3.0 |
| | 57 | 104.3 | 43.7 | 57.3 | 47.0 |
| | | 4.2 | 2.0 | 3.4 | 3.2 |
| | 93 | 97.0 | 44.7 | 51.0 | 37.7 |
| | | 6.1 | 1.8 | 4.2 | 2.2 |
| Female 50 mg/kg IV | −43 | 108.8 | 64.8 | 56.6 | 51.8 |
| | | 7.7 | 6.7 | 6.8 | 5.3 |
| | −8 | 111.8 | 54.6 | 63.2 | 52.4 |
| | | 5.4 | 6.3 | 4.5 | 3.9 |
| | 29 | 115.0 | 54.4 | 61.8 | 43.8 |
| | | 7.9 | 6.2 | 5.1 | 1.4 |
| | 57 | 127.2 | 61.2 | 62.8 | 46.4 |
| | | 9.5 | 9.1 | 5.2 | 4.4 |
| | 93 | 113.2 | 49.2 | 45.0 | 69.8 |
| | | 7.4 | 6.7 | 10.1 | 26.2 |
| Female 200 mg/kg IV | −43 | 97.2 | 55.8 | 63.4 | 50.0 |
| | | 5.5 | 6.5 | 7.5 | 4.4 |
| | −8 | 99.4 | 54.2 | 55.2 | 48.6 |
| | | 10.7 | 8.0 | 3.1 | 5.9 |
| | 29 | 110.8 | 52.0 | 59.6 | 55.2 |
| | | 4.7 | 2.6 | 4.7 | 9.0 |
| | 57 | 119.8 | 54.4 | 62.0 | 65.8 |
| | | 7.2 | 5.8 | 7.3 | 2.2 |
| | 93 | 111.4 | 50.2 | 51.4 | 51.8 |
| | | 8.3 | 7.3 | 3.2 | 5.2 |
| Female 200 mg/kg SC | −43 | 116.0 | 78.6 | 52.6 | 48.8 |
| | | 6.6 | 7.1 | 3.1 | 10.0 |
| | −8 | 116.0 | 62.0 | 62.0 | 52.0 |
| | | 5.1 | 4.7 | 2.6 | 7.3 |
| | 29 | 121.2 | 65.8 | 52.4 | 45.4 |
| | | 7.4 | 11.4 | 6.5 | 2.0 |
| | 57 | 134.4 | 62.4 | 65.4 | 50.4 |
| | | 9.1 | 6.2 | 6.9 | 10.3 |
| | 93 | 119.6 | 52.2 | 55.6 | 45.8 |
| | | 4.0 | 4.7 | 4.0 | 6.1 |
| Male vehicle | −43 | 112.6 | 55.0 | 70.4 | 38.0 |
| | | 4.9 | 4.0 | 2.2 | 4.8 |
| | −8 | 105.4 | 45.0 | 70.0 | 45.0 |
| | | 3.7 | 1.0 | 3.8 | 7.8 |
| | 29 | 122.2 | 47.2 | 76.8 | 47.6 |
| | | 6.3 | 3.6 | 5.7 | 2.8 |
| | 57 | 120.6 | 42.2 | 75.8 | 36.6 |
| | | 6.1 | 2.0 | 5.4 | 4.0 |
| | 93 | 126.8 | 41.8 | 69.6 | 39.2 |
| | | 7.3 | 1.2 | 4.0 | 4.5 |
| Male 10 mg/kg IV | −43 | 113.3 | 64.0 | 62.3 | 41.0 |
| | | 6.4 | 4.0 | 4.3 | 3.2 |
| | −8 | 117.0 | 56.7 | 66.3 | 56.7 |
| | | 5.3 | 3.0 | 3.2 | 18.0 |
| | 29 | 129.0 | 60.0 | 62.0 | 54.3 |
| | | 13.9 | 6.8 | 3.2 | 10.9 |
| | 57 | 123.3 | 51.3 | 70.3 | 47.0 |
| | | 10.4 | 3.4 | 7.0 | 8.9 |
| | 93 | 111.0 | 40.0 | 58.7 | 36.0 |
| | | 13.5 | 5.5 | 11.6 | 6.6 |
| Male 10 mg/kg SC | −43 | 107.3 | 54.0 | 67.3 | 42.0 |
| | | 12.8 | 11.1 | 7.9 | 3.0 |
| | −8 | 100.3 | 45.0 | 64.3 | 48.7 |
| | | 14.7 | 10.7 | 8.5 | 9.0 |
| | 29 | 119.3 | 50.3 | 70.7 | 43.3 |
| | | 16.1 | 11.4 | 9.7 | 2.3 |
| | 57 | 110.3 | 37.3 | 71.3 | 55.3 |
| | | 8.4 | 5.4 | 3.4 | 2.6 |
| | 93 | 107.7 | 36.0 | 67.7 | 37.7 |
| | | 7.4 | 6.7 | 4.4 | 5.5 |
| Male 50 mg/kg IV | −43 | 114.8 | 68.2 | 62.2 | 35.0 |
| | | 7.9 | 8.6 | 5.5 | 3.5 |
| | −8 | 111.2 | 56.2 | 66.2 | 38.4 |
| | | 5.5 | 5.8 | 6.4 | 2.5 |
| | 29 | 118.6 | 56.0 | 57.0 | 41.6 |
| | | 11.8 | 9.5 | 7.2 | 2.6 |
| | 57 | 114.2 | 48.2 | 62.0 | 41.0 |
| | | 8.7 | 6.6 | 5.0 | 4.9 |
| | 93 | 80.4 | 35.6 | 38.2 | 28.0 |
| | | 22.7 | 11.1 | 12.6 | 7.1 |
| Male 200 mg/kg IV | −43 | 112.4 | 64.6 | 64.2 | 35.8 |
| | | 9.3 | 6.3 | 6.1 | 3.5 |
| | −8 | 113.6 | 58.8 | 66.2 | 34.4 |
| | | 8.6 | 5.9 | 3.7 | 2.9 |

TABLE 13-continued

| Dose group mAbS (mg/kg) | Treatment duration (days) | Total cholesterol (mg/dL) | LDL-C (mg/dL) | HDL-C (mg/dL) | TG (mg/dL) |
|---|---|---|---|---|---|
| | 29 | 130.8 | 62.0 | 70.8 | 37.2 |
| | | 10.5 | 6.0 | 7.9 | 7.7 |
| | 57 | 121.4 | 52.6 | 66.8 | 56.4 |
| | | 7.1 | 3.2 | 4.0 | 18.2 |
| | 93 | 109.0 | 51.8 | 56.8 | 45.2 |
| | | 9.9 | 5.0 | 4.8 | 12.5 |
| Male 200 mg/kg SC | −43 | 107.2 | 57.0 | 63.8 | 48.2 |
| | | 6.5 | 5.2 | 2.7 | 6.0 |
| | −8 | 107.6 | 47.8 | 68.4 | 51.0 |
| | | 10.4 | 6.5 | 7.1 | 6.3 |
| | 29 | 111.2 | 50.6 | 62.4 | 43.8 |
| | | 10.2 | 7.8 | 5.8 | 5.2 |
| | 57 | 119.4 | 49.0 | 63.8 | 55.8 |
| | | 7.8 | 5.1 | 3.8 | 18.2 |
| | 93 | 110.6 | 44.0 | 59.2 | 38.8 |
| | | 6.0 | 3.5 | 4.6 | 2.2 |

Table 13 shows the mean (+/−SEM) values for these parameters at baseline (days −43 and −8) and at monthly intervals throughout the dosing schedule (days 29, 57 and 93). There were no significant changes in any of the circulating lipid parameters measured in animals treated with mAb5 at any dose level/dose route, compared to the vehicle-treated control animals and each group's own baseline values (Table 13).

These results demonstrate that chronic treatment with high dose mAb5 glucagon receptor blocking antibody does not result in deleterious elevations in LDL-C or triglycerides.

Example 12

Reversal of Alpha Cell Hyperplasia

This example illustrates the reversal of pancreatic alpha cell hyperplasia with or without hypertrophy in subjects treated with high doses of anti-glucagon receptor antagonist antibody.

It has been shown that blockade of glucagon signaling in mice and/or rats leads to a compensatory elevation in circulating glucagon levels (hyperglucagonemia) and an increase in pancreatic alpha cell number and/or cell size (see, e.g., Gelling et al., 2003, *Proc. Natl. Acad. Sci. USA* 100(3):1438-1443 (GCGR null mice); Sloop et al., 2004, *J. Clin. Invest.* 113(11): 1571-1581 (antisense oligonucleotides); Gu et al., 2009, *J. Pharmacol. Exp. Ther.* 331(3): 871-881 (monoclonal antibody)). As shown above in Example 3, a single dose of 3 mg/kg mAb5 effectively inhibits glucose excursion after glucagon challenge in cynomolgus monkeys, hence the doses chosen for this chronic study (10, 50 and 200 mg/kg) would be expected to produce full blockade of the glucagon signal. In this study, four cohorts of lean, naïve monkeys, each comprising three animals of each gender received 10 mg/kg mAb5 weekly by IV or SC injection for a total of 13 weeks. A further six cohorts of five lean, naïve monkeys of each gender, each received 50 mg/kg mAb5 weekly by IV injection or 200 mg/kg mAb5 weekly by IV or SC injection for a total of 13 weeks. As a control, five lean, naïve, monkeys of each gender received weekly injections of vehicle (by both the IV and SC routes) for 13 weeks.

At the end of the dosing period, the pancreata from three animals per cohort were collected, sectioned and stained using standard H&E, and anti-glucagon/anti-insulin IHC techniques. The pancreata were examined and scored for islet alpha cell hyperplasia and hypertrophy. Two animals of each gender from selected cohorts (control; 50 mg/kg IV; 200 mg/kg IV; 200 mg/kg SC) were then followed for a recovery period (i.e., after discontinuation of mAb5 dosing) of 24 weeks, to allow antibody levels to fall below efficacious thresholds ("antibody washout"). At the end of this antibody washout period, the pancreata from these animals were similarly analyzed for hyperplasia and hypertrophy. The data from this study are summarized in Table 14.

TABLE 14

| | | Number of animals scoring positive after 13 wks treatment | | | | | | Number of animals scoring positive after 24 wks recovery | | | |
|---|---|---|---|---|---|---|---|---|---|---|---|
| | | Control | 10 IV | 10 SC | 50 IV | 200 IV | 200 SC | Control | 50 IV | 200 IV | 200 SC |
| Males | Hyperplasia | 0 | 1 | 1 | 2 | 3 | 3 | 0 | 0 | 0 | 0 |
| | Hypertrophy | 0 | 0 | 0 | 0 | 0 | 0 | 0 | 0 | 0 | 0 |
| Females | Hyperplasia | 0 | 1 | 3 | 3 | 3 | 3 | 0 | 0 | 0 | 0 |
| | Hypertrophy | 0 | 1 | 0 | 0 | 3 | 0 | 0 | 0 | 0 | 0 |

There is evidence of alpha cell hyperplasia and/or hypertrophy in some animals at the 13 week time-point (Table 13, first eight columns). However, neither alpha cell hyperplasia nor hypertrophy was evident in any animal, from any dose group, at the end of the 24 week antibody washout period (Table 13, last four columns). Thus, although chronic, long term treatment with mAb5 at high doses may result in pancreatic alpha cell hyperplasia with or without hypertrophy, these features are fully reversible following antibody washout.

These results demonstrate that changes in the alpha cells of the pancreatic islets after mAb5 treatment in cynomolgus monkeys are fully reversible once levels of therapeutic antibody fall below a minimally efficacious threshold and the blockade of glucagon signaling is relieved.

Example 13

Reversal of Hepatocyte Glycogen Deposition

This example illustrates reversal of hepatocyte glycogen deposition in subjects treated with high doses of anti-glucagon receptor antagonist antibody.

A single dose of 3 mg/kg mAb5 effectively inhibits glucose excursion after glucagon challenge in cynomolgus monkeys (see, Example 3, supra). The doses chosen for this chronic study (10, 50 and 200 mg/kg) would be expected to produce full blockade of the glucagon signal. Four cohorts of lean, naïve monkeys, each comprising three animals of each gender received 10 mg/kg mAb5 weekly by IV or SC injection for a total of 13 weeks. A further six cohorts of five lean, naïve monkeys of each gender, each received 50 mg/kg mAb5 weekly by IV injection or 200 mg/kg mAb5 weekly by IV or SC injection for a total of 13 weeks. As a control, five lean, naïve, monkeys of each gender received weekly injections of vehicle (by both the IV and SC routes) for 13 weeks.

At the end of the dosing period, the livers from three animals per cohort were collected, fixed, sectioned and stained using standard H&E and PAS staining techniques. The livers were examined and scored for increased hepatocellular glycogen deposition. Two animals of each gender from selected cohorts (control; 50 mg/kg IV; 200 mg/kg IV; 200 mg/kg SC) were then followed for a 24-week recovery period after discontinuation of mAb5 dosing to allow antibody levels to fall below efficacious thresholds ("antibody washout"). At the end of this period, the livers from these animals were similarly analyzed. The data from this study are summarized in Table 15.

TABLE 15

Increased hepatocellular glycogen

| Cohort | Control | # animals scoring positive after 13 wks mAb5 treatment | | | | | Control | # animals scoring positive after 24 wks recovery | | |
|---|---|---|---|---|---|---|---|---|---|---|
| | | 10 IV | 10 SC | 50 IV | 200 IV | 200 SC | | 50 IV | 200 IV | 200 SC |
| Males | 0 | 0 | 2 | 0 | 3 | 2 | 0 | 0 | 0 | 0 |
| Females | 0 | 0 | 0 | 1 | 2 | 0 | 0 | 0 | 0 | 0 |

Increased hepatocellular glycogen was observed in some animals after 13 weeks mAb5 treatment (Table 15). For example, 2 males dosed with 10 mg/kg SC mAb5, 1 female dosed with 50 mg/kg IV mAb5, 3 males and 2 females dosed with 200 mg/kg IV mAb, and 2 males dosed with 200 mg/kg SC mAb5 scored positive for increased hepatocellular glycogen (Table 15, first seven columns). However, no evidence of increased hepatocellular glycogen was observed in any animal, from any dose group, after the mAb5 washout time (Table 15, last four columns). Thus, although chronic, long term treatment with mAb5 at high doses may result in changes in hepatocellular glycogen deposition, the changes are fully reversible following antibody washout.

These results demonstrate that changes in glycogen accumulation in hepatocytes after anti-glucagon receptor antagonist antibody treatment in cynomolgus monkeys are fully reversible once levels of therapeutic antibody fall below a minimally efficacious threshold and the blockade of glucagon signaling is relieved.

Example 14

In Vivo Efficacy in a Mouse Model of Type 2 Diabetes

This example illustrates treatment with an anti-glucagon receptor antagonist antibody in a mouse model of type 2 diabetes.

Leptin-deficient male ob/ob mice demonstrate marked hyperphagia resulting in hyperglycemia, hyperinsulinemia and obesity. In this study, male ob/ob mice were administered a single dose of mAb3 at the following doses: 10 mg/kg, 3 mg/kg, 1 mg/kg or 0.3 mg/kg (n=5 for each dose group). Control animals were administered PBS instead of mAb3. Blood samples were taken from all animals (in the fed state) at the following time-points: pre-dose, and on days 1, 2, 5, 6, 7, 9, 12, 13, and 20 post-dose. Whole blood samples were analyzed for glucose concentrations using a hand-held One Touch® glucometer. Mean absolute glucose values+/−SEM are shown in Table 16.

TABLE 16

| Day post-dose | Mean fed blood glucose levels (mg/dL) | | | | | | | | | |
|---|---|---|---|---|---|---|---|---|---|---|
| | PBS | | 10 mg/kg mAb3 | | 3 mg/kg mAb3 | | 1 mg/kg mAb3 | | 0.3 mg/kg mAb3 | |
| | Mean | SEM | Mean | SEM | Mean | SEM | Mean | SEM | Mean | SEM |
| 0 (pre-dose) | 283.60 | 13.04 | 291.00 | 18.12 | 289.00 | 21.85 | 292.00 | 34.09 | 316.00 | 29.68 |
| 1 | 259.80 | 32.54 | 111.20 | 13.50 | 101.60 | 6.76 | 128.60 | 8.26 | 254.60 | 26.62 |
| 2 | 261.80 | 28.13 | 81.80 | 3.64 | 79.20 | 3.62 | 124.00 | 8.79 | 243.80 | 51.43 |
| 5 | 236.60 | 15.36 | 80.60 | 7.45 | 95.20 | 6.95 | 252.40 | 41.83 | 240.40 | 18.28 |
| 6 | 241.20 | 43.40 | 75.60 | 7.71 | 136.60 | 15.50 | 295.80 | 47.64 | 207.60 | 21.09 |
| 7 | 186.20 | 19.53 | 86.60 | 6.39 | 197.20 | 15.55 | 226.80 | 30.26 | 235.40 | 19.18 |
| 9 | 220.80 | 22.73 | 97.60 | 8.85 | 306.00 | 48.24 | 195.60 | 13.92 | 229.40 | 15.25 |
| 12 | 187.20 | 18.74 | 151.40 | 16.81 | 314.20 | 45.06 | 275.00 | 26.34 | 220.80 | 23.90 |
| 13 | 237.00 | 41.55 | 164.60 | 24.08 | 254.00 | 31.44 | 212.20 | 34.32 | 214.40 | 23.26 |
| 20 | 191.80 | 32.66 | 210.20 | 21.57 | 201.40 | 11.54 | 231.60 | 32.00 | 245.60 | 22.34 |

As shown in Table 16, administration of a single intraperitoneal injection of anti-glucagon receptor antagonist antibody mAb3 produces a marked and sustained reduction in the fed blood glucose levels of these mice compared to their pre-treatment baselines or to a vehicle-treated group. The duration of effect showed a dose response, with the 10 mg/kg dose having the longest duration of effect, and the 1 mg/kg dose having the shortest duration of effect (Table 16). Animals treated with anti-glucagon receptor antagonist antibody mAb3 at 10, 3, or 1 mg/kg had significantly improved fed glucose levels one and two days post mAb3 dosing (Table 16, rows 2 and 3).

A single dose of 10 or 3 mg/kg mAb3 produced comparable maximal effects in glucose lowering. For example, at 6 days after treatment with 10 mg/kg mAb3, mice had a fed blood glucose level of 75.60±7.71 mg/dL, and at 2 days after treatment with 3 mg/kg mAb3, mice had a fed blood glucose level of 79.20±3.62 mg/dL. In comparison, control animals given PBS instead of mAb3 had much higher fed blood glucose levels: 261.80±28.13 mg/dL at day 2 after dosing, and 241.20±43.40 mg/dL at day 6 after dosing. A dose of 1 mg/kg produced a lesser effect: at 2 days after treatment with 1 mg/kg mAb3, mice had a fed blood glucose level of 124.00±8.79 mg/dL. No measureable effect was observed with the 0.3 mg/kg dose.

By day 5, glucose levels in animals treated with 1 mg/kg mAb3 had returned to pre-dose levels. However, animals treated with either 3 or 10 mg/kg mAb3 retained improved fed glucose levels until days 7 and 12 post-dose, respectively (Table 16, rows 4, 6 and 8).

These results demonstrate that anti-glucagon receptor antagonist antibody mAb3 effectively reduces fed blood glucose levels in a mouse model of type 2 diabetes.

Example 15

In Vivo Efficacy in a Mouse Model of Type 2 Diabetes

This example illustrates treatment with an anti-glucagon receptor antagonist antibody in mouse models of type 2 diabetes.

HFD-DIO and ob/ob mice are accepted models of some, if not all elements of type 2 diabetes. Both these models manifest overt obesity. Three-month old male mice of both model types were administered either anti-glucagon receptor antagonist antibody mAb3 or PBS (n=10/group/mouse model). mAb3 was administered at 10 mg/kg by weekly intraperitoneal injection over 4 weeks; PBS was administered in a similar manner to control animals. The body weight of each mouse was measured at the end of 1, 2 and 3 weeks of treatment. At each time point, each individual mouse's weight was expressed as a percentage of its pre-dose start weight. Average weight±SEM for each group determined. The results are summarized in Table 17.

TABLE 17

| Mouse Model and Treatment | Mean body weight (% compared to baseline) by the end of: | | | | | |
|---|---|---|---|---|---|---|
| | Week 1 | | Week 2 | | Week 3 | |
| | Mean | SEM | Mean | SEM | Mean | SEM |
| HFD-DIO | | | | | | |
| PBS | 106.47 | 0.74 | 110.57 | 0.88 | 119.42 | 1.41 |
| mAb3 | 103.04 | 0.66 | 106.61 | 0.68 | 114.99 | 1.23 |
| ob/ob | | | | | | |
| PBS | 104.30 | 0.32 | 108.23 | 0.46 | 110.67 | 0.47 |
| mAb3 | 102.87 | 0.23 | 105.88 | 0.89 | 108.20 | 1.18 |

Both HFD-DIO and ob/ob mice treated with anti-glucagon receptor antagonist antibody mAb3 at 10 mg/kg had significantly less body weight gain over the four week duration of the study compared to the mice treated with PBS (Table 17). For example, in the HFD-DIO mice, animals treated with mAb3 had a mean body weight of 114.99±1.23% of baseline, compared to animals given PBS, who had a mean body weight of 119.42±1.41% of baseline. In summary, treatment with mAb3 significantly reduced weight gain in both HFD-DIO mice and ob/ob mice compared to PBS-treated mice.

These results demonstrate that anti-glucagon receptor antagonist antibody can reduce weight gain in two different mouse models of type 2 diabetes.

Example 16

Combination Treatment

This example illustrates combination treatment with an anti-glucagon receptor antagonist antibody and an mTOR inhibitor in mice.

Blocking glucagon signaling in rodents has been previously demonstrated to cause a resultant increase in the number and/or size of pancreatic alpha (i.e., glucagon-producing) cells. See, e.g., Gelling et al., 2003, *Proc. Natl. Acad. Sci. USA* 100(3):1438-1443 (GCGR null mice); Sloop et al., 2004, *J. Clin. Invest.* 113(11): 1571-1581 (antisense oligonucleotides); Gu et al., 2009, *J. Pharmacol. Exp. Ther.* 331 (3): 871-881 (monoclonal antibody). Administration of anti-glucagon receptor antagonist antibody mAb3 (once weekly i.p.) in mice has similarly been shown to increase the number and total area of alpha cells per islet, reflecting an increase in alpha cell number as well as an increase in average alpha cell size.

In this study, male, HFD-DIO mice at 12 weeks of age (n=5 per group) received either once weekly, intra-peritoneal injection of 3 mg/kg mAb3, or daily, intra-peritoneal dosing of 10 mg/kg rapamycin (formulated in 5% ethanol, 5.2% Tween-80, 5.2% PEG 400 in water), in combination with a once weekly 3 mg/kg dose of anti-glucagon receptor antagonist antibody mAb3. A third group received PBS as a control.

After three weeks of treatment, the animals were sacrificed and their pancreata collected, fixed, sectioned, and stained for glucagon (to identify islet alpha cells) and insulin (to identify islet beta cells), as previously described. Algorithms were created to quantify and characterize regions of alpha or beta cells using the anti-glucagon or anti-insulin staining respectively while excluding all irrelevant regions of the tissue. The number of nuclei within each region was also determined using the hematoxylin counter stain and used to calculate the average cell number and average cell size relative to the region (alpha/beta) of each islet.

The study data are summarized in Table 18 below. Table 18 provides (a) the number of alpha cells, quantified as % alpha cell number/islet+/−SEM, (b) the overall area occupied by alpha cells, quantified as % alpha cell area/islet+/−SEM, and (c) average alpha cell size, measured as pixels.

TABLE 18

| Treatment group | % alpha cell number/islet | % alpha cell area/islet | Average alpha cell size (pixels) |
|---|---|---|---|
| PBS | 5.84 +/− 0.80 | 4.58 +/− 0.63 | 416.2 +/− 14.03 |
| mAb3, 3 mg/kg weekly | 21.09 +/− 2.08 | 18.04 +/− 1.90 | 521.1 +/− 6.69 |
| Rapamycin, 10 mg/kg daily + mAb3, 3 mg/kg weekly | 7.13 +/− 3.61 | 6.63 +/− 3.26 | 491.0 +/− 71.51 |

Increased alpha cell number (alpha cell hyperplasia) and alpha cell size (alpha cell hypertrophy) were observed in HFD-DIO mice treated with mAb3, compared to mice administered vehicle only (Table 18). However, these measures of increased alpha cell number and size were absent in HFD-DIO mice when mAb3 was co-administered with rapamycin treatment (Table 18, last row).

These data demonstrate that mTOR signaling may play a role in mediating the alpha cell hyperplasia. These data also demonstrate that co-treatment with an mTOR inhibitor reduces hypertrophy and hyperplasia elicited by blocking glucagon receptor activity.

Example 17

In Vivo Efficacy in Cynomolgus Monkey

This Example illustrates the effect of anti-glucagon receptor antagonist antibody on plasma glucose levels after glucagon challenge in cynomolgus monkeys.

Administration of an intravenous bolus of glucagon to animals leads to an elevation in plasma glucose as a result of glucagon signaling at the liver (glucagon challenge). To determine the doses of mAb5 effective in blocking acute glucagon signaling in vivo, the glucagon challenge paradigm was conducted in lean, naïve, female, cynomolgus monkeys given anti-glucagon receptor antagonist antibody mAb5 at 1, 3, or 30 mg/kg an hour prior to the glucagon challenge being performed. For each cohort of animals, the glucagon challenge was performed on two separate occasions: a first challenge five days before the monkeys received mAb5 to establish a pre-dose baseline for each animal to which the post-dose response was compared, and a second challenge one hour after the monkeys received the mAb5 dose.

For each glucagon challenge, an IV bolus of 20 μg/kg glucagon (GlucaGen® Hypokits®) was administered at time 0. Blood samples were taken from all animals at the following time-points: immediately pre-challenge, and at 5, 15, 30, 45, 60 and 120 minutes post-challenge. Plasma samples were analyzed for plasma glucose concentrations using a clinical chemistry analyzer. The results (mean change in glucose levels+/−SEM in mg/dL) are summarized in Table 19. Due to inter-animal variability in their starting blood glucose levels, data are shown as change in absolute glucose value from the pre-challenge value.

TABLE 19

| Treatment Group | | Mean change in absolute glucose value from pre-challenge value (mg/dL) Time (mins) relative to glucagon administration | | | | | |
|---|---|---|---|---|---|---|---|
| | | 5 | 15 | 30 | 45 | 60 | 120 |
| mAb5 30 mg/kg (n = 3) | Glucagon challange (GC) at baseline | 41.33 ± 9.82 | 45.67 ± 6.84 | 26.33 ± 6.69 | 12.67 ± 6.06 | 14.67 ± .31 | −15.00 ± 7.09 |
| | GC 1 hr post-mAb5 | −15.00 ± 16.74 | −16.67 ± 14.17 | −20.67 ± 16.90 | −15.67 ± 7.22 | −26.00 ± 12.90 | −33.67 ± 14.99 |
| mAb5 3 mg/kg (n = 4) | GC at baseline | 37.00 ± 17.23 | 56.75 ± 26.52 | 38.75 ± 34.36 | 21.00 ± 35.53 | 16.25 ± 28.04 | −23.50 ± 4.35 |
| | GC 1 hr post-mAb5 | 13.25 ± 11.43 | 16.25 ± 22.45 | 6.75 ± 25.85 | 8.75 ± 24.34 | 1.50 ± 25.69 | −24.50 ± 6.33 |
| mAb5 1 mg/kg (n = 3) | GC at baseline | 51.67 ± 13.69 | 52.00 ± 14.19 | 25.00 ± 17.35 | 15.33 ± 23.62 | 14.00 ± 19.14 | −6.33 ± 2.19 |
| | GC 1 hr post-mAb5 | 3.00 ± 11.59 | 1.00 ± 14.73 | −14.33 ± 10.99 | −23.00 ± 6.66 | −18.00 ± 7.81 | −32.00 ± 8.08 |

In each group, on Day −5, the glucagon challenge without prior mAb5 treatment resulted in an increase in plasma glucose levels, reflecting the physiological response of the liver increasing glucose production and output as a result of glucagon stimulation (baseline) (Table 19, rows labeled "GC at baseline"). Glucose levels peaked 15 minutes after the glucagon challenge and generally returned to pre-challenge, or even lower levels between 60-120 minutes post challenge Treatment with mAb5 one hour prior to a glucagon challenge resulted in a marked inhibition of the glucose response to glucagon challenge relative to the baseline response (Table 19, rows labeled "GC 1 hr post-mAb5"). Peak glucose excursions in these groups were minimal and in some cases negative, generally observed at earlier time points, and returned more quickly to normal or indeed lower than pre-challenge levels. For example, at 15 minutes post-GC (the time at which glucose levels peaked during the baseline challenge) the blood glucose level of animals treated with 30 mg/kg mAb5 was 16.67±14.17 mg/dL lower than at pre-challenge. However, at 15 minutes post-GC without mAb5 treatment, the blood glucose levels of these same animals was 45.67±6.84 mg/dL higher than at pre-challenge. At 15 minutes post-GC, the blood glucose level of animals treated with 3 mg/kg mAb5 was 16.25±22.45 mg/dL higher than at pre-challenge. In contrast, at 15 minutes post-GC without mAb5 treatment, the blood glucose levels of these same animals was 56.75±26.52 mg/dL higher than at pre-challenge. At 15 minutes post-GC, the blood glucose level of animals treated with 1 mg/kg mAb5 was 1.00±14.73 mg/dL higher than at pre-challenge. In contrast, at 15 minutes post-GC without mAb5 treatment, the blood glucose levels of these same animals was 52.00±14.19 mg/dL higher than at pre-challenge. Doses of 30, 3 or 1 mg/kg mAb5 showed similar efficacy in this paradigm with no dose response.

These results demonstrate that mAb5 is efficacious at blocking glucagon signaling in vivo, and anti-glucagon receptor antagonist antibody effectively blocks glucose excursion after glucagon challenge.

Example 18

In Vivo Efficacy in Cynomolgus Monkey

This Example illustrates the effect of anti-glucagon receptor antagonist antibody on plasma glucose levels after glucagon challenge in cynomolgus monkeys.

Administration of an intravenous bolus of glucagon to animals leads to an elevation in plasma glucose as a result of glucagon signaling at the liver (glucagon challenge). To determine other doses of mAb5 which may be effective in blocking acute glucagon signaling in vivo, the glucagon challenge paradigm was conducted in lean, naïve, female, cynomolgus monkeys given anti-glucagon receptor antagonist antibody mAb5 at 1.78, 0.24 or 0.026 mg/kg an hour prior to the glucagon challenge being performed. An additional cohort of animals received PBS vehicle only (n=4/group). For each cohort of animals, the glucagon challenge was performed on three separate occasions: a first challenge at three days before the monkeys received mAb5 to establish a pre-dose baseline for each animal and ensure all animals are glucagon-responsive; a second challenge one hour after the monkeys received the mAb5 dose; and third challenge one week after the monkeys received the mAb5 dose.

For each glucagon challenge, an IV bolus of 20 μg/kg glucagon (GlucaGen® Hypokits®) was administered at time 0. Blood samples were taken from all animals at the following time-points: pre-challenge, and at 5, 15, 30, 45, 60 and 120 minutes post-challenge. Plasma samples were analyzed for plasma glucose concentrations using a clinical chemistry analyzer. The results (mean change in glucose levels+/−SEM in mg/dL) from the second and third challenges are summarized in Table 20. Due to inter-animal variability in their starting blood glucose levels, data are shown as change in absolute glucose value from the pre-challenge value taken on that day.

Post-glucagon challenge (GC) changes in blood glucose levels in animals treated with mAb5 can be compared to changes in blood glucose levels in animals pre-treated with PBS receiving GC on the same day (Table 20). Peak glucose levels were generally observed at the 5 minute time point. During GC one hour post mAb5 dose at 0.026 and 0.24 mg/kg, only very slight if any reductions in glucose response were seen. For example, in animals challenged 1 hour after treatment with 0.026 and 0.24 mg/kg mAb5, increases in blood glucose levels of 30.25±6.65 mg/dL and 44.25±6.21 mg/dL, respectively, were observed at peak glucose level, compared to an increase of 34.75±5.57 mg/dL in animals given PBS instead of mAb5 (Table 20). By Day 8, the response in the 0.026 and 0.24 mg/kg mAb5 dosing groups was similar to control animals.

However, in the 1.78 mg/kg mAb5 treatment group, moderate inhibition of the glucagon response at one hour post dose was observed. In animals treated with 1.78 mg/kg mAb5, plasma glucose levels were lower than in other groups, peaking at 5 minutes (22.25±1.49 mg/dL), and were recovered to baseline or below by 30-45 minutes post challenge (Table 20). This inhibition of the glucagon response was observed even when a repeat glucagon challenge was conducted seven days post administration of mAb5 (Table 20). A significant treatment effect of 1.78 mg/kg mAb5 was also evident in reducing pre-challenge (i.e. fasting) plasma glucose levels relative (60.0±3.79 mg/dL) to plasma glucose levels in the vehicle treated group (85.50±8.17 mg/d L).

These results demonstrate that anti-glucagon receptor antagonist antibody effectively blocks glucose excursion after glucagon challenge.

Example 19

Epitope Mapping

The crystal structure of anti-glucagon receptor antagonist antibody mAb5 and the crystal structure of the mAb5:gluca-

TABLE 20

| Treatment | | Mean change in absolute glucose value from pre-challenge value (mg/dL) Time (mins) relative to glucagon administration | | | | | |
|---|---|---|---|---|---|---|---|
| | Group | 5 | 15 | 30 | 45 | 60 | 120 |
| Glucagon challenge 1 hour post mAb5 | PBS (control, no mAb) | 28.00 ± 3.00 | 34.75 ± 5.57 | −2.50 ± 7.12 | −10.75 ± 7.63 | −11.25 ± 11.66 | −29.50 ± 7.08 |
| | 1.78 mg/kg mAb5 | 22.25 ± 1.49 | 5.75 ± 5.63 | −14.25 ± 7.91 | −11.75 ± 5.15 | −2.75 ± 3.75 | −7.00 ± 3.24 |
| | 0.24 mg/kg mAb5 | 44.25 ± 6.21 | 27.50 ± 4.63 | 6.00 ± 5.24 | −1.25 ± 7.59 | −5.75 ± 7.59 | −10.25 ± 3.90 |
| | 0.026 mg/kg mAb5 | 30.25 ± 6.65 | 20.75 ± 8.73 | 0.25 ± 1.65 | −9.25 ± 5.28 | −3.25 ± 2.84 | −15.50 ± 2.72 |
| Glucagon challenge 7 days post mAB5 | PBS (control, no mAb) | 22.50 ± 8.03 | 18.50 ± 10.12 | −7.00 ± 7.45 | −11.00 ± 9.17 | −14.25 ± 11.15 | −34.25 ± 5.91 |
| | 1.78 mg/kg mAb5 | 19.00 ± 7.52 | 8.50 ± 7.19 | −9.25 ± 6.29 | −4.00 ± 7.72 | −11.50 ± 3.40 | −24.50 ± 4.94 |
| | 0.24 mg/kg mAb5 | 34.75 ± 14.46 | 30.50 ± 12.26 | 0.25 ± 14.56 | −6.75 ± 11.71 | −5.75 ± 17.38 | −22.00 ± 11.50 |
| | 0.026 mg/kg mAb5 | 28.50 ± 2.53 | 21.25 ± 7.72 | −9.00 ± 3.83 | −13.00 ± 4.80 | −21.00 ± 5.90 | −29.75 ± 7.50 | gon receptor complex were used to characterize the epitope on human glucagon receptor recognized by mAb5. The glucagon receptor residues involved in binding were identified by calculating the difference in accessibility surface area between the mAb5:glucagon receptor crystal structure and the glucagon receptor structure alone. Glucagon receptor residues that show buried surface area upon complex formation with mAb5 antibody were included as part of the epitope. The solvent accessible surface of a protein was defined as the locus of the centre of a probe sphere (representing a solvent molecule of 1.4 A radius) as it rolls over the Van der Waals surface of the protein. The solvent accessible surface area was calculated by generating surface points on an extended sphere around each atom (at a distance from the atom centre equal to the sum of the atom and probe radii), and eliminating those that lie within equivalent spheres associated with neighboring atoms as implemented in the program MODELLER (A. Sali & T. L. Blundell. J. Mol. Biol. 234, 779-815, 1993). Based on the crystal structure analysis, the structural epitope on glucagon receptor recognized by mAb5 involves the amino acid residues at positions 31, 33-38, 40-42, 44-45, 48, 62, and 64 of human glucagon receptor (SEQ ID NO: 1).

The identity of the residues that dominate the binding energy of a large protein-protein interface has been termed the "functional epitope" (Cunningham, B. C. and Wells, J. A., 1993, J. Mol. Biol., 234, 554-563). The affinity of the interaction (and hence biological specificity) is consequently defined by the structural complementarity of the functional epitopes of ligand and receptor. Detailed mutagenesis studies have shown that the most significant residues that make up the functional epitopes of cytokines and receptors are hydrophobic contacts involving either non-polar side chains such as tryptophan, the aliphatic components of non-polar side chains or the polypeptide backbone. The non-polar "core" is surrounded by a halo of polar residues of lesser importance for binding energy. Kinetic studies indicate that the primary role of the functional epitopes is to stabilize protein-protein interaction by decreasing the dissociation rate of the complex. It has been suggested that the initial contact between cytokine and receptor is dominated by random diffusion or "rolling" of protein surfaces producing many unstable contacts. The complex is then stabilized when the functional epitopes of the receptor and ligand engage (see, e.g., Bravo and Heath, 2000, EMBO J. 19:2399-2411).

Yeast display was used to determine the amino acid residues involved in the functional epitope on glucagon receptor recognized by mAb5. A library of single point mutants of the glucagon receptor extracellular domain (GCGR-ECD) was displayed on yeast cells. The GCGR-ECD-expressing yeast cells (the "original library") were then incubated with either fluorescence-labeled mAb5 or a pool of fluorescence-labeled non-mAb5 anti-glucagon receptor antibodies. Wild-type glucagon receptor was used as a positive control. Yeast cells displaying GCGR-ECD mutants with decreased antibody binding relative to wild-type GCGR-ECD were isolated by FACS. This population of cells (the "enriched library") was deep sequenced and the data analyzed to determine enrichment of each mutant. Enrichment is defined as the incidence of a specific mutant in the enriched library (following FACS isolation) in comparison to its incidence in the original library, e.g., an enrichment of 4.0 means that the mutant is present in the enriched library at four times the frequency at which it is found in the original library. Greater enrichment corresponds to GCGR-ECD mutants with lower binding affinity. Three rounds of panning were carried out, with consistency between the three different rounds. Table 21 summarizes the results of the yeast display analysis.

TABLE 21

| GCGR-ECD Mutants | | Enrichment | | | |
|---|---|---|---|---|---|
| Position of point mutation | Wild-type amino acid at mutated position | mAb5 | | | Non-mAb5 |
| | | Panning Round 1 | Panning Round 2 | Panning Round 3 | pooled antibodies |
| 33 | F | 4.8 | 5.3 | 5.3 | 0.3 |
| 36 | W | 5.4 | 6.7 | 8.5 | 6.1 |
| 38 | L | 2.5 | 3.3 | 3.9 | 0.2 |
| 41 | D | 3.4 | 4.0 | 4.2 | 0.4 |
| 44 | H | 3.2 | 3.3 | 3.9 | 0.1 |
| 45 | H | 4.4 | 5.1 | 5.3 | 0.4 |
| 54 | T | 1.0 | 1.0 | 1.1 | 3.4 |
| 60 | R | 3.8 | 5.0 | 5.7 | 31.5 |
| 61 | T | 1.6 | 1.4 | 1.3 | 1.4 |
| 64 | K | 0.2 | 0.1 | 0.2 | 0.1 |
| 74 | N | 2.7 | 2.5 | 2.8 | 5.3 |
| 87 | W | 0.8 | 0.6 | 0.4 | 0.4 |
| 88 | H | 1.3 | 1.2 | 0.9 | 1.6 |
| 90 | K | 0.7 | 0.6 | 0.6 | 0.9 |
| 93 | H | 1.7 | 1.9 | 2.1 | 4.1 |
| 94 | R | 1.8 | 2.0 | 2.4 | 5.1 |
| 97 | F | 1.2 | 1.2 | 1.0 | 1.2 |
| 99 | R | 0.7 | 0.6 | 0.7 | 1.0 |
| 103 | D | 2.3 | 2.2 | 1.9 | 2.4 |
| 108 | R | 1.3 | 1.5 | 1.3 | 2.8 |

Mutated positions with enrichment greater than three in any round are considered to be part of the functional epitope on glucagon receptor recognized by mAb5. Based on the yeast display analysis, the functional epitope on glucagon receptor recognized by mAb5 involves the amino acid residues at positions 33, 36, 38, 41, 44, 45 and 60 of SEQ ID NO: 1 (Table 21, bold positions). Position 60 is the only enriched residue not also found in the structural epitope; it is also enriched in the pool of non-mAb5 antibodies, indicating demonstrating the residue at this position perturbs protein folding.

An analysis was carried out to determine which positions in the mutant library and in the structural epitope are not enriched. Out of the fifteen positions in the structural epitope, eleven positions are also present in the mutant library. Out of these eleven positions, six positions are enriched. The five non-enriched positions in the functional epitope are 31, 34, 42, 48 and 64. All the non-enriched positions are located on the periphery of the structural epitope.

Although the disclosed teachings have been described with reference to various applications, methods, kits, and compositions, it will be appreciated that various changes and modifications can be made without departing from the teachings herein and the claimed invention below. The foregoing examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

The foregoing description and Examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

It is claimed:

1. An isolated antagonist antibody that specifically binds to glucagon receptor and comprises:
    a heavy chain variable region (VH) comprising a VH complementarity determining region one (CDR1), VH CDR2, and VH CDR3 of the VH having the amino acid sequence shown in SEQ ID NO: 11; and
    a light chain variable region (VL) comprising a VL CDR1, VL CDR2, and VL CDR3 of the VL having the amino acid sequence shown in SEQ ID NO: 10.

2. The isolated antagonist antibody of claim 1, wherein the antibody comprises a VH CDR1 comprising the amino acid sequence of SEQ ID NO: 24, 16 or 25, a VH CDR2 comprising the amino acid sequence of SEQ ID NO: 18 or 26, a VH CDR3 comprising the amino acid sequence shown in SEQ ID NO: 41, a VL CDR1 comprising the amino acid sequence shown in SEQ ID NO: 40, a VL CDR2 comprising the amino acid sequence shown in SEQ ID NO: 13, and a VL CDR3 comprising the amino acid sequence shown in SEQ ID NO: 14.

3. The isolated antagonist antibody of claim 1, wherein the antibody comprises a VH comprising the amino acid sequence shown in SEQ ID NO: 11 or a variant thereof with one or several conservative amino acid substitutions in residues that are not within a CDR.

4. The isolated antagonist antibody of claim 3, wherein the antibody comprises a VL comprising the amino acid sequence shown in SEQ ID NO: 10 or a variant thereof with one or several amino acid substitutions in amino acids that are not within a CDR.

5. The isolated antagonist antibody of claim 4, wherein the antibody comprises a VH comprising the amino acid sequence shown in SEQ ID NO: 11 and a VL comprising the amino acid sequence shown in SEQ ID NO: 10.

6. The isolated antagonist antibody of claim 5, wherein the antibody comprises a heavy chain comprising the amino acid sequence shown in SEQ ID NO: 87 or 88 and a light chain comprising the amino acid sequence shown in SEQ ID NO: 89.

7. The isolated antagonist antibody of claim 1, wherein the antibody further comprises an immunologically inert constant region.

8. The isolated antagonist antibody of claim 7, wherein the antibody has an isotype that is selected from the group consisting of $IgG_2$, $IgG_{2\Delta a}$, $IgG_4$, $IgG_{4\Delta b}$, $IgG_{4\Delta c}$, $IgG_4$ S228P, $IgG_{4\Delta b}$ S228P and $IgG_{4\Delta c}$ S228P.

9. The isolated antagonist antibody of claim 7, wherein the constant region is aglycosylated Fc.

10. The isolated antagonist antibody of claim 1, wherein each CDR of the antibody is defined in accordance with the Kabat definition, the Chothia definition, the combination of the Kabat definition and the Chothia definition, the AbM definition, or the contact definition of CDR.

11. The isolated antagonist antibody of claim 1, wherein the antibody comprises a VH CDR1 comprising the amino acid sequence of SEQ ID NO: 17, a VH CDR2 comprising the amino acid sequence of SEQ ID NO: 93, a VH CDR3 comprising the amino acid sequence shown in SEQ ID NO: 94, a VL CDR1 comprising the amino acid sequence shown in SEQ ID NO: 90, a VL CDR2 comprising the amino acid sequence shown in SEQ ID NO: 91, and a VL CDR3 comprising the amino acid sequence shown in SEQ ID NO: 92.

12. A hybridoma capable of producing the antibody of claim 1.

13. A pharmaceutical composition comprising the antibody of claim 1 and a pharmaceutically acceptable carrier.

14. A kit for the treatment of a condition associated with aberrant blood glucose level comprising the pharmaceutical composition of claim 13.

* * * * *

SEQUENCE LISTING

```
<160> NUMBER OF SEQ ID NOS: 94

<210> SEQ ID NO 1
<211> LENGTH: 477
<212> TYPE: PRT
<213> ORGANISM: Homo Sapiens

<400> SEQUENCE: 1

Met Pro Pro Cys Gln Pro Gln Arg Pro Leu Leu Leu Leu Leu Leu Leu
1               5                   10                  15

Leu Ala Cys Gln Pro Gln Val Pro Ser Ala Gln Val Met Asp Phe Leu
                20                  25                  30

Phe Glu Lys Trp Lys Leu Tyr Gly Asp Gln Cys His His Asn Leu Ser
            35                  40                  45

Leu Leu Pro Pro Pro Thr Glu Leu Val Cys Asn Arg Thr Phe Asp Lys
        50                  55                  60

Tyr Ser Cys Trp Pro Asp Thr Pro Ala Asn Thr Thr Ala Asn Ile Ser
65                  70                  75                  80

Cys Pro Trp Tyr Leu Pro Trp His His Lys Val Gln His Arg Phe Val
                85                  90                  95

Phe Lys Arg Cys Gly Pro Asp Gly Gln Trp Val Arg Gly Pro Arg Gly
                100                 105                 110

Gln Pro Trp Arg Asp Ala Ser Gln Cys Gln Met Asp Gly Glu Glu Ile
            115                 120                 125

Glu Val Gln Lys Glu Val Ala Lys Met Tyr Ser Ser Phe Gln Val Met
        130                 135                 140

Tyr Thr Val Gly Tyr Ser Leu Ser Leu Gly Ala Leu Leu Leu Ala Leu
145                 150                 155                 160

Ala Ile Leu Gly Gly Leu Ser Lys Leu His Cys Thr Arg Asn Ala Ile
                165                 170                 175

His Ala Asn Leu Phe Ala Ser Phe Val Leu Lys Ala Ser Ser Val Leu
                180                 185                 190

Val Ile Asp Gly Leu Leu Arg Thr Arg Tyr Ser Gln Lys Ile Gly Asp
            195                 200                 205

Asp Leu Ser Val Ser Thr Trp Leu Ser Asp Gly Ala Val Ala Gly Cys
        210                 215                 220

Arg Val Ala Ala Val Phe Met Gln Tyr Gly Ile Val Ala Asn Tyr Cys
225                 230                 235                 240

Trp Leu Leu Val Glu Gly Leu Tyr Leu His Asn Leu Leu Gly Leu Ala
                245                 250                 255

Thr Leu Pro Glu Arg Ser Phe Phe Ser Leu Tyr Leu Gly Ile Gly Trp
                260                 265                 270

Gly Ala Pro Met Leu Phe Val Val Pro Trp Ala Val Val Lys Cys Leu
            275                 280                 285

Phe Glu Asn Val Gln Cys Trp Thr Ser Asn Asp Asn Met Gly Phe Trp
        290                 295                 300

Trp Ile Leu Arg Phe Pro Val Phe Leu Ala Ile Leu Ile Asn Phe Phe
305                 310                 315                 320

Ile Phe Val Arg Ile Val Gln Leu Leu Val Ala Lys Leu Arg Ala Arg
```

```
                325                 330                 335
Gln Met His His Thr Asp Tyr Lys Phe Arg Leu Ala Lys Ser Thr Leu
            340                 345                 350

Thr Leu Ile Pro Leu Leu Gly Val His Glu Val Val Phe Ala Phe Val
        355                 360                 365

Thr Asp Glu His Ala Gln Gly Thr Leu Arg Ser Ala Lys Leu Phe Phe
    370                 375                 380

Asp Leu Phe Leu Ser Ser Phe Gln Gly Leu Leu Val Ala Val Leu Tyr
385                 390                 395                 400

Cys Phe Leu Asn Lys Glu Val Gln Ser Glu Leu Arg Arg Arg Trp His
                405                 410                 415

Arg Trp Arg Leu Gly Lys Val Leu Trp Glu Arg Asn Thr Ser Asn
            420                 425                 430

His Arg Ala Ser Ser Pro Gly His Gly Pro Ser Lys Glu Leu
        435                 440                 445

Gln Phe Gly Arg Gly Gly Ser Gln Asp Ser Ser Ala Glu Thr Pro
    450                 455                 460

Leu Ala Gly Gly Leu Pro Arg Leu Ala Glu Ser Pro Phe
465                 470                 475

<210> SEQ ID NO 2
<211> LENGTH: 107
<212> TYPE: PRT
<213> ORGANISM: Mus musculus

<400> SEQUENCE: 2

Asp Ile Val Met Thr Gln Ser Gln Lys Phe Met Ser Ala Ser Val Gly
1               5                   10                  15

Asp Arg Val Ser Ile Thr Cys Lys Ala Ser Gln Asn Val Arg Thr Ala
            20                  25                  30

Val Val Trp Phe Gln Gln Lys Pro Gly Gln Ser Pro Asn Thr Leu Ile
        35                  40                  45

Tyr Leu Ala Ser Asn Arg His Ser Glu Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Leu Gln His Trp Thr Tyr Pro Phe
                85                  90                  95

Thr Phe Ala Ser Gly Thr Lys Leu Glu Ile Lys
            100                 105

<210> SEQ ID NO 3
<211> LENGTH: 120
<212> TYPE: PRT
<213> ORGANISM: Mus musculus

<400> SEQUENCE: 3

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Phe
            20                  25                  30

Ser Ile His Trp Val Lys Gln Ala Pro Gly Lys Gly Leu Lys Trp Met
        35                  40                  45

Gly Trp Ile Asn Thr Glu Thr Asp Glu Ser Thr Tyr Ala Asp Asp Phe
    50                  55                  60

Lys Gly Arg Phe Ala Phe Ser Leu Glu Thr Ser Ala Ser Thr Ala Tyr
```

```
                65                  70                  75                  80
Leu Gln Ile Asn Asn Leu Lys Asn Glu Asp Thr Ala Thr Tyr Phe Cys
                        85                  90                  95

Val Lys Ser Arg Gly Trp Thr Tyr Gly Pro Pro Asp Tyr Trp Gly Gln
                100                 105                 110

Gly Thr Thr Leu Thr Val Ser Ser
            115                 120

<210> SEQ ID NO 4
<211> LENGTH: 107
<212> TYPE: PRT
<213> ORGANISM: Artificial Sequence
<220> FEATURE:
<223> OTHER INFORMATION: Humanized antibody sequence

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Arg Thr Ala
                20                  25                  30

Val Val Trp Tyr Gln Gln Lys Pro Gly Lys Ala Pro Lys Leu Leu Ile
            35                  40                  45

Tyr Leu Ala Thr Asn Arg His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln His Trp Thr Tyr Pro Phe
                85                  90                  95

Ser Phe Gly Gly Gly Thr Lys Leu Glu Ile Lys
                100                 105

<210> SEQ ID NO 5
<211> LENGTH: 120
<212> TYPE: PRT
<213> ORGANISM: Artificial Sequence
<220> FEATURE:
<223> OTHER INFORMATION: Humanized antibody sequence

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
                20                  25                  30

Ser Val His Trp Val Arg Gln Ala Pro Gly Gln Gly Leu Glu Trp Met
            35                  40                  45

Gly Trp Ile Asn Thr Glu Thr Asp Glu Thr Ser Tyr Ala Asp Asp Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Val Lys Ser Arg Gly Trp Ser Tyr Gly Pro Pro Asp Tyr Trp Gly Gln
                100                 105                 110

Gly Thr Thr Val Thr Val Ser Ser
            115                 120

<210> SEQ ID NO 6
<211> LENGTH: 107
```

```
<212> TYPE: PRT
<213> ORGANISM: Mus musculus

<400> SEQUENCE: 6

Asp Ile Gln Met Thr Gln Ser Pro Ala Ser Leu Ala Ala Ser Val Gly
1               5                   10                  15

Glu Thr Val Thr Ile Thr Cys Arg Ala Ser Glu Asn Ile Tyr Tyr Ser
            20                  25                  30

Leu Ala Trp Tyr Gln Gln Lys Gln Gly Lys Ser Pro Gln Leu Leu Ile
        35                  40                  45

Tyr Asn Ala Asn Ser Leu Glu Asp Gly Val Pro Ser Arg Phe Ser Gly
50                  55                  60

Ser Gly Ser Gly Thr Gln Tyr Ser Met Lys Ile Asn Ser Ile Gln Pro
65                  70                  75                  80

Glu Asp Thr Ala Thr Tyr Phe Cys Lys Gln Ala Tyr Asp Val Pro Phe
                85                  90                  95

Thr Phe Gly Ser Gly Thr Lys Leu Val Ile Lys
            100                 105

<210> SEQ ID NO 7
<211> LENGTH: 120
<212> TYPE: PRT
<213> ORGANISM: Mus musculus

<400> SEQUENCE: 7

Glu Val Gln Leu Gln Gln Ser Gly Pro Glu Leu Ile Lys Pro Gly Ala
1               5                   10                  15

Ser Val Lys Met Ser Cys Lys Ala Ser Gly Tyr Thr Phe Thr Ser Cys
            20                  25                  30

Leu Ile His Trp Val Lys Leu Lys Pro Gly Gln Gly Leu Glu Trp Ile
        35                  40                  45

Gly Tyr Ile Asn Pro Tyr Asn Asp Gly Thr Lys Tyr Asn Glu Lys Phe
50                  55                  60

Lys Gly Arg Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Met Asp Tyr Gly Asn Leu Trp Tyr Phe Asp Val Trp Gly Ala
            100                 105                 110

Gly Thr Thr Val Thr Val Ser Ser
        115                 120

<210> SEQ ID NO 8
<211> LENGTH: 107
<212> TYPE: PRT
<213> ORGANISM: Artificial Sequence
<220> FEATURE:
<223> OTHER INFORMATION: Humanized antibody sequence

<400> SEQUENCE: 8

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Asn Ile Tyr Tyr Ser
            20                  25                  30

Leu Ala Trp Tyr Gln Gln Lys Pro Gly Gln Ala Pro Arg Leu Leu Ile
        35                  40                  45

Tyr Asn Ala Asn Ser Leu Glu Asp Gly Ile Pro Ala Arg Phe Ser Gly
50                  55                  60
```

```
Ser Gly Ser Gly Thr Asp Phe Thr Leu Thr Ile Ser Ser Leu Glu Pro
 65                  70                  75                  80

Glu Asp Phe Ala Val Tyr Tyr Cys Lys Gln Ala Tyr Asp Val Pro Phe
                 85                  90                  95

Thr Phe Gly Gly Gly Thr Lys Val Glu Ile Lys
            100                 105

<210> SEQ ID NO 9
<211> LENGTH: 120
<212> TYPE: PRT
<213> ORGANISM: Artificial Sequence
<220> FEATURE:
<223> OTHER INFORMATION: Humanized antibody sequence

<400> SEQUENCE: 9

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Ser
                20                  25                  30

Leu Ile His Trp Val Arg Gln Ala Pro Gly Gln Gly Leu Glu Trp Met
             35                  40                  45

Gly Tyr Ile Asn Pro Tyr Asn Asp Gly Thr Lys Tyr Asn Glu Lys Phe
 50                  55                  60

Lys Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Met Asp Tyr Gly Asn Leu Trp Tyr Phe Asp Val Trp Gly Gln
            100                 105                 110

Gly Thr Leu Val Thr Val Ser Ser
            115                 120

<210> SEQ ID NO 10
<211> LENGTH: 107
<212> TYPE: PRT
<213> ORGANISM: Artificial Sequence
<220> FEATURE:
<223> OTHER INFORMATION: Humanized antibody sequence

<400> SEQUENCE: 10

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asn Ile Arg Thr Ala
                20                  25                  30

Val Val Trp Tyr Gln Gln Lys Pro Gly Lys Ala Pro Lys Leu Leu Ile
             35                  40                  45

Tyr Leu Ala Ser Asn Arg His Ser Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Leu Gln His Trp Thr Tyr Pro Phe
                 85                  90                  95

Thr Phe Gly Gly Gly Thr Lys Val Glu Ile Lys
            100                 105

<210> SEQ ID NO 11
<211> LENGTH: 120
<212> TYPE: PRT
```

<213> ORGANISM: Artificial Sequence
<220> FEATURE:
<223> OTHER INFORMATION: Humanized antibody sequence

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Ser Val His Trp Val Arg Gln Ala Pro Gly Gln Gly Leu Glu Trp Met
        35                  40                  45

Gly Trp Ile Asn Thr Glu Thr Asp Gly Thr Ser Tyr Ala Asp Asp Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Val Lys Ser Arg Tyr Trp Ser Tyr Gly Pro Pro Asp Tyr Trp Gly Gln
            100                 105                 110

Gly Thr Thr Val Thr Val Ser Ser
        115                 120

<210> SEQ ID NO 12
<211> LENGTH: 11
<212> TYPE: PRT
<213> ORGANISM: Artificial Sequence
<220> FEATURE:
<223> OTHER INFORMATION: Humanized antibody sequence

<400> SEQUENCE: 12

Lys Ala Ser Gln Asn Val Arg Thr Ala Val Val
1               5                   10

<210> SEQ ID NO 13
<211> LENGTH: 7
<212> TYPE: PRT
<213> ORGANISM: Artificial Sequence
<220> FEATURE:
<223> OTHER INFORMATION: Humanized antibody sequence

<400> SEQUENCE: 13

Leu Ala Ser Asn Arg His Ser
1               5

<210> SEQ ID NO 14
<211> LENGTH: 9
<212> TYPE: PRT
<213> ORGANISM: Artificial Sequence
<220> FEATURE:
<223> OTHER INFORMATION: Humanized antibody sequence

<400> SEQUENCE: 14

Leu Gln His Trp Thr Tyr Pro Phe Thr
1               5

<210> SEQ ID NO 15
<211> LENGTH: 10
<212> TYPE: PRT
<213> ORGANISM: Artificial Sequence
<220> FEATURE:
<223> OTHER INFORMATION: Humanized antibody sequence

<400> SEQUENCE: 15

```
Gly Tyr Thr Phe Thr Asp Phe Ser Ile His
1               5                   10

<210> SEQ ID NO 16
<211> LENGTH: 7
<212> TYPE: PRT
<213> ORGANISM: Artificial Sequence
<220> FEATURE:
<223> OTHER INFORMATION: Humanized antibody sequence

<400> SEQUENCE: 16

Gly Tyr Thr Phe Thr Asp Phe
1               5

<210> SEQ ID NO 17
<211> LENGTH: 5
<212> TYPE: PRT
<213> ORGANISM: Artificial Sequence
<220> FEATURE:
<223> OTHER INFORMATION: Humanized antibody sequence

<400> SEQUENCE: 17

Asp Phe Ser Ile His
1               5

<210> SEQ ID NO 18
<211> LENGTH: 6
<212> TYPE: PRT
<213> ORGANISM: Artificial Sequence
<220> FEATURE:
<223> OTHER INFORMATION: Humanized antibody sequence

<400> SEQUENCE: 18

Asn Thr Glu Thr Asp Glu
1               5

<210> SEQ ID NO 19
<211> LENGTH: 17
<212> TYPE: PRT
<213> ORGANISM: Artificial Sequence
<220> FEATURE:
<223> OTHER INFORMATION: Humanized antibody sequence

<400> SEQUENCE: 19

Trp Ile Asn Thr Glu Thr Asp Glu Ser Thr Tyr Ala Asp Asp Phe Lys
1               5                   10                  15

Gly

<210> SEQ ID NO 20
<211> LENGTH: 11
<212> TYPE: PRT
<213> ORGANISM: Artificial Sequence
<220> FEATURE:
<223> OTHER INFORMATION: Humanized antibody sequence

<400> SEQUENCE: 20

Ser Arg Gly Trp Thr Tyr Gly Pro Pro Asp Tyr
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Humanized antibody sequence

<400> SEQUENCE: 21
```

```
Arg Ala Ser Gln Asn Ile Arg Thr Ala Val Val
1               5                   10

<210> SEQ ID NO 22
<211> LENGTH: 7
<212> TYPE: PRT
<213> ORGANISM: Artificial Sequence
<220> FEATURE:
<223> OTHER INFORMATION: Humanized antibody sequence

<400> SEQUENCE: 22

Leu Ala Thr Asn Arg His Ser
1               5

<210> SEQ ID NO 23
<211> LENGTH: 9
<212> TYPE: PRT
<213> ORGANISM: Artificial Sequence
<220> FEATURE:
<223> OTHER INFORMATION: Humanized antibody sequence

<400> SEQUENCE: 23

Leu Gln His Trp Thr Tyr Pro Phe Ser
1               5

<210> SEQ ID NO 24
<211> LENGTH: 10
<212> TYPE: PRT
<213> ORGANISM: Artificial Sequence
<220> FEATURE:
<223> OTHER INFORMATION: Humanized antibody sequence

<400> SEQUENCE: 24

Gly Tyr Thr Phe Thr Asp Phe Ser Val His
1               5                   10

<210> SEQ ID NO 25
<211> LENGTH: 5
<212> TYPE: PRT
<213> ORGANISM: Artificial Sequence
<220> FEATURE:
<223> OTHER INFORMATION: Humanized antibody sequence

<400> SEQUENCE: 25

Asp Phe Ser Val His
1               5

<210> SEQ ID NO 26
<211> LENGTH: 17
<212> TYPE: PRT
<213> ORGANISM: Artificial Sequence
<220> FEATURE:
<223> OTHER INFORMATION: Humanized antibody sequence

<400> SEQUENCE: 26

Trp Ile Asn Thr Glu Thr Asp Glu Thr Ser Tyr Ala Asp Asp Phe Lys
1               5                   10                  15

Gly

<210> SEQ ID NO 27
<211> LENGTH: 11
<212> TYPE: PRT
<213> ORGANISM: Artificial Sequence
<220> FEATURE:
<223> OTHER INFORMATION: Humanized antibody sequence
```

```
<400> SEQUENCE: 27

Ser Arg Gly Trp Ser Tyr Gly Pro Pro Asp Tyr
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Humanized antibody sequence

<400> SEQUENCE: 28

Arg Ala Ser Glu Asn Ile Tyr Tyr Ser Leu Ala
1               5                   10

<210> SEQ ID NO 29
<211> LENGTH: 7
<212> TYPE: PRT
<213> ORGANISM: Artificial Sequence
<220> FEATURE:
<223> OTHER INFORMATION: Humanized antibody sequence

<400> SEQUENCE: 29

Asn Ala Asn Ser Leu Glu Asp
1               5

<210> SEQ ID NO 30
<211> LENGTH: 9
<212> TYPE: PRT
<213> ORGANISM: Artificial Sequence
<220> FEATURE:
<223> OTHER INFORMATION: Humanized antibody sequence

<400> SEQUENCE: 30

Lys Gln Ala Tyr Asp Val Pro Phe Thr
1               5

<210> SEQ ID NO 31
<211> LENGTH: 10
<212> TYPE: PRT
<213> ORGANISM: Artificial Sequence
<220> FEATURE:
<223> OTHER INFORMATION: Humanized antibody sequence

<400> SEQUENCE: 31

Gly Tyr Thr Phe Thr Ser Cys Leu Ile His
1               5                   10

<210> SEQ ID NO 32
<211> LENGTH: 7
<212> TYPE: PRT
<213> ORGANISM: Artificial Sequence
<220> FEATURE:
<223> OTHER INFORMATION: Humanized antibody sequence

<400> SEQUENCE: 32

Gly Tyr Thr Phe Thr Ser Cys
1               5

<210> SEQ ID NO 33
<211> LENGTH: 5
<212> TYPE: PRT
<213> ORGANISM: Artificial Sequence
<220> FEATURE:
<223> OTHER INFORMATION: Humanized antibody sequence

<400> SEQUENCE: 33
```

```
Ser Cys Leu Ile His
1               5

<210> SEQ ID NO 34
<211> LENGTH: 6
<212> TYPE: PRT
<213> ORGANISM: Artificial Sequence
<220> FEATURE:
<223> OTHER INFORMATION: Humanized antibody sequence

<400> SEQUENCE: 34

Asn Pro Tyr Asn Asp Gly
1               5

<210> SEQ ID NO 35
<211> LENGTH: 17
<212> TYPE: PRT
<213> ORGANISM: Artificial Sequence
<220> FEATURE:
<223> OTHER INFORMATION: Humanized antibody sequence

<400> SEQUENCE: 35

Tyr Ile Asn Pro Tyr Asn Asp Gly Thr Lys Tyr Asn Glu Lys Phe Lys
1               5                   10                  15

Gly

<210> SEQ ID NO 36
<211> LENGTH: 11
<212> TYPE: PRT
<213> ORGANISM: Artificial Sequence
<220> FEATURE:
<223> OTHER INFORMATION: Humanized antibody sequence

<400> SEQUENCE: 36

Met Asp Tyr Gly Asn Leu Trp Tyr Phe Asp Val
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Humanized antibody sequence

<400> SEQUENCE: 37

Gly Tyr Thr Phe Thr Ser Ser Leu Ile His
1               5                   10

<210> SEQ ID NO 38
<211> LENGTH: 7
<212> TYPE: PRT
<213> ORGANISM: Artificial Sequence
<220> FEATURE:
<223> OTHER INFORMATION: Humanized antibody sequence

<400> SEQUENCE: 38

Gly Tyr Thr Phe Thr Ser Ser
1               5

<210> SEQ ID NO 39
<211> LENGTH: 5
<212> TYPE: PRT
<213> ORGANISM: Artificial Sequence
<220> FEATURE:
<223> OTHER INFORMATION: Humanized antibody sequence
```

```
<400> SEQUENCE: 39

Ser Ser Leu Ile His
1               5

<210> SEQ ID NO 40
<211> LENGTH: 11
<212> TYPE: PRT
<213> ORGANISM: Artificial Sequence
<220> FEATURE:
<223> OTHER INFORMATION: Humanized antibody sequence

<400> SEQUENCE: 40

Gln Ala Ser Gln Asn Ile Arg Thr Ala Val Val
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Humanized antibody sequence

<400> SEQUENCE: 41

Ser Arg Tyr Trp Ser Tyr Gly Pro Pro Asp Tyr
1               5                   10

<210> SEQ ID NO 42
<211> LENGTH: 106
<212> TYPE: PRT
<213> ORGANISM: Mus musculus

<400> SEQUENCE: 42

Gln Ile Val Leu Ser Gln Ser Pro Ala Ile Leu Ser Ala Ser Pro Gly
1               5                   10                  15

Glu Lys Val Thr Met Thr Cys Arg Ala Asn Ser Thr Leu Asn Tyr Met
            20                  25                  30

His Trp Tyr Gln Gln Lys Pro Gly Ser Ser Pro Lys Pro Trp Ile Phe
        35                  40                  45

Gly Thr Ser Ile Leu Ala Ser Gly Val Pro Leu Arg Phe Ser Gly Ser
    50                  55                  60

Gly Ser Gly Thr Ser Tyr Ser Leu Thr Ile Ser Arg Val Glu Thr Glu
65                  70                  75                  80

Asp Ala Ala Thr Tyr Tyr Cys Gln Gln Trp Ser Ser Asn Pro Trp Thr
                85                  90                  95

Phe Gly Gly Gly Thr Lys Leu Glu Ile Lys
            100                 105

<210> SEQ ID NO 43
<211> LENGTH: 119
<212> TYPE: PRT
<213> ORGANISM: Mus musculus

<400> SEQUENCE: 43

Asp Val Gln Phe Gln Glu Ser Gly Pro Gly Leu Val Lys Pro Ser Gln
1               5                   10                  15

Ser Leu Ser Leu Thr Cys Thr Val Thr Asp Tyr Ser Phe Thr Ser Asp
            20                  25                  30

Tyr Ala Trp Asn Trp Phe Arg Gln Phe Pro Gly Asn Lys Leu Glu Trp
        35                  40                  45

Met Gly Tyr Ile Asn Tyr Ser Gly Ser Thr Asn Tyr Asn Pro Ser Leu
    50                  55                  60
```

```
Lys Ser Arg Ile Ser Ile Thr Arg Asp Thr Ser Lys Asn Gln Phe Phe
 65                  70                  75                  80

Leu Gln Leu Asn Ser Val Thr Glu Asp Thr Ala Thr Tyr Tyr Cys
             85                  90                  95

Ala Ser Thr Val Val Glu Gly Tyr Tyr Phe Asp Tyr Trp Gly Gln Gly
            100                 105                 110

Thr Thr Leu Thr Val Ser Ser
        115

<210> SEQ ID NO 44
<211> LENGTH: 11
<212> TYPE: PRT
<213> ORGANISM: Artificial Sequence
<220> FEATURE:
<223> OTHER INFORMATION: Humanized antibody sequence

<400> SEQUENCE: 44

Arg Ala Ser Gln Asn Val Arg Thr Ala Val Val
 1               5                  10

<210> SEQ ID NO 45
<211> LENGTH: 11
<212> TYPE: PRT
<213> ORGANISM: Artificial Sequence
<220> FEATURE:
<223> OTHER INFORMATION: Humanized antibody sequence

<400> SEQUENCE: 45

Lys Ala Ser Gln Asn Val Arg Ser Ala Val Val
 1               5                  10

<210> SEQ ID NO 46
<211> LENGTH: 11
<212> TYPE: PRT
<213> ORGANISM: Artificial Sequence
<220> FEATURE:
<223> OTHER INFORMATION: Humanized antibody sequence

<400> SEQUENCE: 46

Lys Ala Ser Gln Asn Val Arg Thr Ala Leu Asn
 1               5                  10

<210> SEQ ID NO 47
<211> LENGTH: 7
<212> TYPE: PRT
<213> ORGANISM: Artificial Sequence
<220> FEATURE:
<223> OTHER INFORMATION: Humanized antibody sequence

<400> SEQUENCE: 47

Leu Ala Thr Asn Arg His Ser
 1               5

<210> SEQ ID NO 48
<211> LENGTH: 7
<212> TYPE: PRT
<213> ORGANISM: Artificial Sequence
<220> FEATURE:
<223> OTHER INFORMATION: Humanized antibody sequence

<400> SEQUENCE: 48

Leu Ala Ser Asn Arg His Gly
 1               5
```

```
<210> SEQ ID NO 49
<211> LENGTH: 9
<212> TYPE: PRT
<213> ORGANISM: Artificial Sequence
<220> FEATURE:
<223> OTHER INFORMATION: Humanized antibody sequence

<400> SEQUENCE: 49

Gln Gln His Trp Thr Tyr Pro Phe Thr
1               5

<210> SEQ ID NO 50
<211> LENGTH: 9
<212> TYPE: PRT
<213> ORGANISM: Artificial Sequence
<220> FEATURE:
<223> OTHER INFORMATION: Humanized antibody sequence

<400> SEQUENCE: 50

Leu Gln His Trp Thr Tyr Pro Phe Ser
1               5

<210> SEQ ID NO 51
<211> LENGTH: 17
<212> TYPE: PRT
<213> ORGANISM: Artificial Sequence
<220> FEATURE:
<223> OTHER INFORMATION: Humanized antibody sequence

<400> SEQUENCE: 51

Trp Ile Asn Thr Glu Ser Asp Glu Ser Thr Tyr Ala Asp Asp Phe Lys
1               5                   10                  15

Gly

<210> SEQ ID NO 52
<211> LENGTH: 17
<212> TYPE: PRT
<213> ORGANISM: Artificial Sequence
<220> FEATURE:
<223> OTHER INFORMATION: Humanized antibody sequence

<400> SEQUENCE: 52

Trp Ile Asn Thr Glu Thr Asp Glu Thr Ser Tyr Ala Asp Asp Phe Lys
1               5                   10                  15

Gly

<210> SEQ ID NO 53
<211> LENGTH: 17
<212> TYPE: PRT
<213> ORGANISM: Artificial Sequence
<220> FEATURE:
<223> OTHER INFORMATION: Humanized antibody sequence

<400> SEQUENCE: 53

Trp Ile Asn Ser Glu Thr Asp Glu Ser Thr Tyr Ala Asp Asp Phe Lys
1               5                   10                  15

Gly

<210> SEQ ID NO 54
<211> LENGTH: 17
<212> TYPE: PRT
<213> ORGANISM: Artificial Sequence
<220> FEATURE:
<223> OTHER INFORMATION: Humanized antibody sequence

<400> SEQUENCE: 54
```

Trp Ile Asn Thr Glu Thr Asp Glu Ser Thr Tyr Ala Gln Asn Phe Gln
1               5                   10                  15

Gly

<210> SEQ ID NO 55
<211> LENGTH: 13
<212> TYPE: PRT
<213> ORGANISM: Artificial Sequence
<220> FEATURE:
<223> OTHER INFORMATION: Humanized antibody sequence

<400> SEQUENCE: 55

Val Lys Ser Arg Gly Trp Ser Tyr Gly Pro Pro Asp Tyr
1               5                   10

<210> SEQ ID NO 56
<211> LENGTH: 13
<212> TYPE: PRT
<213> ORGANISM: Artificial Sequence
<220> FEATURE:
<223> OTHER INFORMATION: Humanized antibody sequence

<400> SEQUENCE: 56

Val Lys Ser Arg Gly Trp Thr Tyr Gly Pro Pro Asp Val
1               5                   10

<210> SEQ ID NO 57
<211> LENGTH: 120
<212> TYPE: PRT
<213> ORGANISM: Artificial Sequence
<220> FEATURE:
<223> OTHER INFORMATION: Humanized antibody sequence

<400> SEQUENCE: 57

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Ser Val His Trp Val Arg Gln Ala Pro Gly Gln Gly Leu Glu Trp Met
        35                  40                  45

Gly Trp Ile Asn Thr Glu Phe Asp Phe Thr Ser Tyr Ala Asp Asp Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Val Lys Ser Arg Gly Trp Ser Tyr Gly Pro Pro Asp Tyr Trp Gly Gln
            100                 105                 110

Gly Thr Thr Val Thr Val Ser Ser
        115                 120

<210> SEQ ID NO 58
<211> LENGTH: 120
<212> TYPE: PRT
<213> ORGANISM: Artificial Sequence
<220> FEATURE:
<223> OTHER INFORMATION: Humanized antibody sequence

<400> SEQUENCE: 58

Gln Val Gln Leu Val Gln Ser Gly Ala Glu Val Lys Lys Pro Gly Ala
1               5                   10                  15

-continued

```
Ser Val Lys Val Ser Cys Lys Ala Ser Gly Tyr Thr Phe Thr Asp Phe
            20                  25                  30

Ser Val His Trp Val Arg Gln Ala Pro Gly Gln Gly Leu Glu Trp Met
        35                  40                  45

Gly Trp Ile Asn Thr Glu Tyr Asp Phe Thr Ser Tyr Ala Asp Asp Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Val Lys Ser Arg Gly Trp Ser Tyr Gly Pro Pro Asp Tyr Trp Gly Gln
            100                 105                 110

Gly Thr Thr Val Thr Val Ser Ser
        115                 120

<210> SEQ ID NO 59
<211> LENGTH: 120
<212> TYPE: PRT
<213> ORGANISM: Artificial Sequence
<220> FEATURE:
<223> OTHER INFORMATION: Humanized antibody sequence

<400> SEQUENCE: 59

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Ser Val His Trp Val Arg Gln Ala Pro Gly Gln Gly Leu Glu Trp Met
        35                  40                  45

Gly Trp Ile Asn Thr Glu Thr Arg Gly Thr Ser Tyr Ala Asp Asp Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Val Lys Ser Arg Gly Trp Ser Tyr Gly Pro Pro Asp Tyr Trp Gly Gln
            100                 105                 110

Gly Thr Thr Val Thr Val Ser Ser
        115                 120

<210> SEQ ID NO 60
<211> LENGTH: 120
<212> TYPE: PRT
<213> ORGANISM: Artificial Sequence
<220> FEATURE:
<223> OTHER INFORMATION: Humanized antibody sequence

<400> SEQUENCE: 60

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Ser Val His Trp Val Arg Gln Ala Pro Gly Gln Gly Leu Glu Trp Met
        35                  40                  45

Gly Trp Tyr Asn Leu Glu Thr Asp Glu Thr Ser Tyr Ala Asp Asp Phe
    50                  55                  60

Lys Gly Arg Val Thr Met Thr Arg Asp Thr Ser Thr Ser Thr Val Tyr
65                  70                  75                  80
```

Met Glu Leu Ser Ser Leu Arg Ser Glu Asp Thr Ala Val Tyr Tyr Cys
              85                  90                  95

Val Lys Ser Arg Gly Trp Ser Tyr Gly Pro Pro Asp Tyr Trp Gly Gln
            100                 105                 110

Gly Thr Thr Val Thr Val Ser Ser
        115                 120

<210> SEQ ID NO 61
<211> LENGTH: 120
<212> TYPE: PRT
<213> ORGANISM: Artificial Sequence
<220> FEATURE:
<223> OTHER INFORMATION: Humanized antibody sequence

<400> SEQUENCE: 61

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Ser Val His Trp Val Arg Gln Ala Pro Gly Gln Gly Leu Glu Trp Met
        35                  40                  45

Gly Trp Ile Asn Leu Glu Phe Asp Glu Thr Ser Tyr Ala Asp Asp Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
              85                  90                  95

Val Lys Ser Arg Gly Trp Ser Tyr Gly Pro Pro Asp Tyr Trp Gly Gln
            100                 105                 110

Gly Thr Thr Val Thr Val Ser Ser
        115                 120

<210> SEQ ID NO 62
<211> LENGTH: 120
<212> TYPE: PRT
<213> ORGANISM: Artificial Sequence
<220> FEATURE:
<223> OTHER INFORMATION: Humanized antibody sequence

<400> SEQUENCE: 62

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Ser Val His Trp Val Arg Gln Ala Pro Gly Gln Gly Leu Glu Trp Met
        35                  40                  45

Gly Trp Ile Asn Thr Glu Phe Asp Tyr Thr Ser Tyr Ala Asp Asp Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
              85                  90                  95

Val Lys Ser Arg Gly Trp Ser Tyr Gly Pro Pro Asp Tyr Trp Gly Gln
            100                 105                 110

Gly Thr Thr Val Thr Val Ser Ser
        115                 120

-continued

```
<210> SEQ ID NO 63
<211> LENGTH: 120
<212> TYPE: PRT
<213> ORGANISM: Artificial Sequence
<220> FEATURE:
<223> OTHER INFORMATION: Humanized antibody sequence

<400> SEQUENCE: 63

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Ser Val His Trp Val Arg Gln Ala Pro Gly Gln Gly Leu Glu Trp Met
        35                  40                  45

Gly Trp Ile Asn Thr Glu Thr Asp Glu Thr Ser Tyr Ala Asp Asp Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Val Glu Ser Leu Tyr Trp Ser Tyr Gly Pro Pro Asp Tyr Trp Gly Gln
            100                 105                 110

Gly Thr Thr Val Thr Val Ser Ser
        115                 120

<210> SEQ ID NO 64
<211> LENGTH: 120
<212> TYPE: PRT
<213> ORGANISM: Artificial Sequence
<220> FEATURE:
<223> OTHER INFORMATION: Humanized antibody sequence

<400> SEQUENCE: 64

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Ser Val His Trp Val Arg Gln Ala Pro Gly Gln Gly Leu Glu Trp Met
        35                  40                  45

Gly Trp Ile Asn Thr Glu Thr Asp Glu Thr Ser Tyr Ala Asp Asp Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Val Lys Ser Leu Tyr Trp Ser Tyr Gly Pro Pro Asp Tyr Trp Gly Gln
            100                 105                 110

Gly Thr Thr Val Thr Val Ser Ser
        115                 120

<210> SEQ ID NO 65
<211> LENGTH: 120
<212> TYPE: PRT
<213> ORGANISM: Artificial Sequence
<220> FEATURE:
<223> OTHER INFORMATION: Humanized antibody sequence

<400> SEQUENCE: 65

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Asp Phe
        20                  25                  30

Ser Val His Trp Val Arg Gln Ala Pro Gly Gln Gly Leu Glu Trp Met
        35                  40                  45

Gly Trp Ile Asn Thr Glu Thr Asp Glu Thr Ser Tyr Ala Asp Asp Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Val Lys Ser Leu Phe Trp Ser Tyr Gly Pro Pro Asp Tyr Trp Gly Gln
            100                 105                 110

Gly Thr Thr Val Thr Val Ser Ser
        115                 120

<210> SEQ ID NO 66
<211> LENGTH: 120
<212> TYPE: PRT
<213> ORGANISM: Artificial Sequence
<220> FEATURE:
<223> OTHER INFORMATION: Humanized antibody sequence

<400> SEQUENCE: 66

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
        20                  25                  30

Ser Val His Trp Val Arg Gln Ala Pro Gly Gln Gly Leu Glu Trp Met
        35                  40                  45

Gly Trp Ile Asn Thr Glu Thr Asp Glu Thr Ser Tyr Ala Asp Asp Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Val Lys Ser Arg Trp Trp Ser Tyr Gly Pro Pro Asp Tyr Trp Gly Gln
            100                 105                 110

Gly Thr Thr Val Thr Val Ser Ser
        115                 120

<210> SEQ ID NO 67
<211> LENGTH: 120
<212> TYPE: PRT
<213> ORGANISM: Artificial Sequence
<220> FEATURE:
<223> OTHER INFORMATION: Humanized antibody sequence

<400> SEQUENCE: 67

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
        20                  25                  30

Ser Val His Trp Val Arg Gln Ala Pro Gly Gln Gly Leu Glu Trp Met
        35                  40                  45

Gly Trp Ile Asn Thr Glu Tyr Asp Phe Thr Ser Tyr Ala Asp Asp Phe
    50                  55                  60

Lys Gly Arg Val Thr Met Thr Arg Asp Thr Ser Thr Ser Thr Val Tyr
```

65                  70                  75                  80
Met Glu Leu Ser Ser Leu Arg Ser Glu Asp Thr Ala Val Tyr Tyr Cys
                    85                  90                  95

Val Glu Ser Leu Tyr Trp Ser Tyr Gly Pro Pro Asp Tyr Trp Gly Gln
                100                 105                 110

Gly Thr Thr Val Thr Val Ser Ser
            115                 120

<210> SEQ ID NO 68
<211> LENGTH: 120
<212> TYPE: PRT
<213> ORGANISM: Artificial Sequence
<220> FEATURE:
<223> OTHER INFORMATION: Humanized antibody sequence

<400> SEQUENCE: 68

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
                20                  25                  30

Ser Val His Trp Val Arg Gln Ala Pro Gly Gln Gly Leu Glu Trp Met
            35                  40                  45

Gly Trp Ile Asn Thr Glu Tyr Asp Phe Thr Ser Tyr Ala Asp Asp Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                    85                  90                  95

Val Lys Ser Leu Phe Trp Ser Tyr Gly Pro Pro Asp Tyr Trp Gly Gln
                100                 105                 110

Gly Thr Thr Val Thr Val Ser Ser
            115                 120

<210> SEQ ID NO 69
<211> LENGTH: 120
<212> TYPE: PRT
<213> ORGANISM: Artificial Sequence
<220> FEATURE:
<223> OTHER INFORMATION: Humanized antibody sequence

<400> SEQUENCE: 69

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
                20                  25                  30

Ser Val His Trp Val Arg Gln Ala Pro Gly Gln Gly Leu Glu Trp Met
            35                  40                  45

Gly Trp Ile Asn Thr Glu Tyr Asp Phe Thr Ser Tyr Ala Asp Asp Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                    85                  90                  95

Val Lys Ser Leu Tyr Trp Ser Tyr Gly Pro Pro Asp Tyr Trp Gly Gln
                100                 105                 110

Gly Thr Thr Val Thr Val Ser Ser
            115                 120

<210> SEQ ID NO 70
<211> LENGTH: 120
<212> TYPE: PRT
<213> ORGANISM: Artificial Sequence
<220> FEATURE:
<223> OTHER INFORMATION: Humanized antibody sequence

<400> SEQUENCE: 70

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Ser Val His Trp Val Arg Gln Ala Pro Gly Gln Gly Leu Glu Trp Met
        35                  40                  45

Gly Trp Ile Asn Thr Glu Tyr Asp Phe Thr Ser Tyr Ala Asp Asp Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Val Lys Ser Arg Trp Trp Ser Tyr Gly Pro Pro Asp Tyr Trp Gly Gln
            100                 105                 110

Gly Thr Thr Val Thr Val Ser Ser
        115                 120
```

<210> SEQ ID NO 71
<211> LENGTH: 120
<212> TYPE: PRT
<213> ORGANISM: Artificial Sequence
<220> FEATURE:
<223> OTHER INFORMATION: Humanized antibody sequence

<400> SEQUENCE: 71

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Ser Val His Trp Val Arg Gln Ala Pro Gly Gln Gly Leu Glu Trp Met
        35                  40                  45

Gly Trp Ile Asn Thr Glu Thr Arg Gly Thr Ser Tyr Ala Asp Asp Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Val Glu Ser Leu Tyr Trp Ser Tyr Gly Pro Pro Asp Tyr Trp Gly Gln
            100                 105                 110

Gly Thr Thr Val Thr Val Ser Ser
        115                 120
```

<210> SEQ ID NO 72
<211> LENGTH: 120
<212> TYPE: PRT
<213> ORGANISM: Artificial Sequence
<220> FEATURE:
<223> OTHER INFORMATION: Humanized antibody sequence

<400> SEQUENCE: 72

```
Gln Val Gln Leu Val Gln Ser Gly Ala Glu Val Lys Lys Pro Gly Ala
```

```
                1               5                  10                  15
Ser Val Lys Val Ser Cys Lys Ala Ser Gly Tyr Thr Phe Thr Asp Phe
                20                  25                  30

Ser Val His Trp Val Arg Gln Ala Pro Gly Gln Gly Leu Glu Trp Met
            35                  40                  45

Gly Trp Ile Asn Thr Glu Thr Arg Gly Thr Ser Tyr Ala Asp Asp Phe
        50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Val Lys Ser Leu Phe Trp Ser Tyr Gly Pro Pro Asp Tyr Trp Gly Gln
                100                 105                 110

Gly Thr Thr Val Thr Val Ser Ser
            115                 120

<210> SEQ ID NO 73
<211> LENGTH: 120
<212> TYPE: PRT
<213> ORGANISM: Artificial Sequence
<220> FEATURE:
<223> OTHER INFORMATION: Humanized antibody sequence

<400> SEQUENCE: 73

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
                20                  25                  30

Ser Val His Trp Val Arg Gln Ala Pro Gly Gln Gly Leu Glu Trp Met
            35                  40                  45

Gly Trp Ile Asn Thr Glu Thr Arg Gly Thr Ser Tyr Ala Asp Asp Phe
        50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Val Lys Ser Leu Tyr Trp Ser Tyr Gly Pro Pro Asp Tyr Trp Gly Gln
                100                 105                 110

Gly Thr Thr Val Thr Val Ser Ser
            115                 120

<210> SEQ ID NO 74
<211> LENGTH: 120
<212> TYPE: PRT
<213> ORGANISM: Artificial Sequence
<220> FEATURE:
<223> OTHER INFORMATION: Humanized antibody sequence

<400> SEQUENCE: 74

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
                20                  25                  30

Ser Val His Trp Val Arg Gln Ala Pro Gly Gln Gly Leu Glu Trp Met
            35                  40                  45

Gly Trp Ile Asn Thr Glu Thr Arg Gly Thr Ser Tyr Ala Asp Asp Phe
        50                  55                  60
```

```
Lys Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Val Lys Ser Arg Trp Trp Ser Tyr Gly Pro Pro Asp Tyr Trp Gly Gln
            100                 105                 110

Gly Thr Thr Val Thr Val Ser Ser
        115                 120

<210> SEQ ID NO 75
<211> LENGTH: 120
<212> TYPE: PRT
<213> ORGANISM: Artificial Sequence
<220> FEATURE:
<223> OTHER INFORMATION: Humanized antibody sequence

<400> SEQUENCE: 75

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Ser Val His Trp Val Arg Gln Ala Pro Gly Gln Gly Leu Glu Trp Met
        35                  40                  45

Gly Trp Tyr Asn Leu Glu Thr Asp Glu Thr Ser Tyr Ala Asp Asp Phe
    50                  55                  60

Lys Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Val Glu Ser Leu Tyr Trp Ser Tyr Gly Pro Pro Asp Tyr Trp Gly Gln
            100                 105                 110

Gly Thr Thr Val Thr Val Ser Ser
        115                 120

<210> SEQ ID NO 76
<211> LENGTH: 120
<212> TYPE: PRT
<213> ORGANISM: Artificial Sequence
<220> FEATURE:
<223> OTHER INFORMATION: Humanized antibody sequence

<400> SEQUENCE: 76

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Ser Val His Trp Val Arg Gln Ala Pro Gly Gln Gly Leu Glu Trp Met
        35                  40                  45

Gly Trp Tyr Asn Leu Glu Thr Asp Glu Thr Ser Tyr Ala Asp Asp Phe
    50                  55                  60

Lys Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Val Lys Ser Leu Phe Trp Ser Tyr Gly Pro Pro Asp Tyr Trp Gly Gln
            100                 105                 110

Gly Thr Thr Val Thr Val Ser Ser
        115                 120
```

```
<210> SEQ ID NO 77
<211> LENGTH: 120
<212> TYPE: PRT
<213> ORGANISM: Artificial Sequence
<220> FEATURE:
<223> OTHER INFORMATION: Humanized antibody sequence

<400> SEQUENCE: 77

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
                20                  25                  30

Ser Val His Trp Val Arg Gln Ala Pro Gly Gln Gly Leu Glu Trp Met
            35                  40                  45

Gly Trp Tyr Asn Leu Glu Thr Asp Glu Thr Ser Tyr Ala Asp Asp Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Val Lys Ser Leu Tyr Trp Ser Tyr Gly Pro Pro Asp Tyr Trp Gly Gln
                100                 105                 110

Gly Thr Thr Val Thr Val Ser Ser
            115                 120

<210> SEQ ID NO 78
<211> LENGTH: 120
<212> TYPE: PRT
<213> ORGANISM: Artificial Sequence
<220> FEATURE:
<223> OTHER INFORMATION: Humanized antibody sequence

<400> SEQUENCE: 78

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
                20                  25                  30

Ser Val His Trp Val Arg Gln Ala Pro Gly Gln Gly Leu Glu Trp Met
            35                  40                  45

Gly Trp Tyr Asn Leu Glu Thr Asp Glu Thr Ser Tyr Ala Asp Asp Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Val Lys Ser Arg Trp Trp Ser Tyr Gly Pro Pro Asp Tyr Trp Gly Gln
                100                 105                 110

Gly Thr Thr Val Thr Val Ser Ser
            115                 120

<210> SEQ ID NO 79
<211> LENGTH: 107
<212> TYPE: PRT
<213> ORGANISM: Artificial Sequence
<220> FEATURE:
<223> OTHER INFORMATION: Humanized antibody sequence

<400> SEQUENCE: 79
```

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asn Ile Arg Thr Ala
            20                  25                  30

Val Val Trp Tyr Gln Gln Lys Pro Gly Lys Ala Pro Lys Leu Leu Ile
            35                  40                  45

Tyr Leu Ala Ser Asn Arg His Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln His Trp Thr Tyr Pro Phe
                85                  90                  95

Thr Phe Gly Gly Gly Thr Lys Val Glu Ile Lys
            100                 105
```

<210> SEQ ID NO 80
<211> LENGTH: 120
<212> TYPE: PRT
<213> ORGANISM: Artificial Sequence
<220> FEATURE:
<223> OTHER INFORMATION: Humanized antibody sequence

<400> SEQUENCE: 80

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Ser Val His Trp Val Arg Gln Ala Pro Gly Gln Gly Leu Glu Trp Met
            35                  40                  45

Gly Trp Ile Asn Thr Glu Tyr Asp Phe Thr Ser Tyr Ala Asp Asp Phe
50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Val Lys Ser Leu Tyr Trp Ser Tyr Gly Pro Pro Asp Tyr Trp Gly Gln
            100                 105                 110

Gly Thr Thr Val Thr Val Ser Ser
            115                 120
```

<210> SEQ ID NO 81
<211> LENGTH: 120
<212> TYPE: PRT
<213> ORGANISM: Artificial Sequence
<220> FEATURE:
<223> OTHER INFORMATION: Humanized antibody sequence

<400> SEQUENCE: 81

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Ser Val His Trp Val Arg Gln Ala Pro Gly Gln Gly Leu Glu Trp Met
            35                  40                  45

Gly Trp Ile Asn Thr Glu Tyr Asp Phe Thr Ser Tyr Ala Gln Lys Phe
50                  55                  60

Gln Gly Arg Val Thr Met Thr Arg Asp Thr Ser Thr Ser Thr Val Tyr
65                  70                  75                  80
```

```
Met Glu Leu Ser Ser Leu Arg Ser Glu Asp Thr Ala Val Tyr Tyr Cys
                85                  90                  95

Val Lys Ser Leu Tyr Trp Ser Tyr Gly Pro Pro Asp Tyr Trp Gly Gln
            100                 105                 110

Gly Thr Leu Val Thr Val Ser Ser
        115                 120

<210> SEQ ID NO 82
<211> LENGTH: 120
<212> TYPE: PRT
<213> ORGANISM: Artificial Sequence
<220> FEATURE:
<223> OTHER INFORMATION: Humanized antibody sequence

<400> SEQUENCE: 82

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Ser Val His Trp Val Arg Gln Ala Pro Gly Gln Gly Leu Glu Trp Met
        35                  40                  45

Gly Trp Ile Asn Thr Glu Tyr Asp Phe Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Val Lys Ser Leu Tyr Trp Ser Tyr Gly Pro Pro Asp Tyr Trp Gly Gln
            100                 105                 110

Gly Thr Leu Val Thr Val Ser Ser
        115                 120

<210> SEQ ID NO 83
<211> LENGTH: 120
<212> TYPE: PRT
<213> ORGANISM: Artificial Sequence
<220> FEATURE:
<223> OTHER INFORMATION: Humanized antibody sequence

<400> SEQUENCE: 83

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Ser Val His Trp Val Arg Gln Ala Pro Gly Gln Gly Leu Glu Trp Met
        35                  40                  45

Gly Trp Ile Asn Thr Glu Thr Asp Glu Thr Ser Tyr Ala Asp Asp Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Val Lys Ser Leu Tyr Trp Ser Tyr Gly Pro Pro Asp Tyr Trp Gly Gln
            100                 105                 110

Gly Thr Thr Val Thr Val Ser Ser
        115                 120
```

<210> SEQ ID NO 84
<211> LENGTH: 120
<212> TYPE: PRT
<213> ORGANISM: Artificial Sequence
<220> FEATURE:
<223> OTHER INFORMATION: Humanized antibody sequence

<400> SEQUENCE: 84

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Ser Val His Trp Val Arg Gln Ala Pro Gly Gln Gly Leu Glu Trp Met
        35                  40                  45

Gly Trp Ile Asn Thr Glu Thr Arg Gly Thr Ser Tyr Ala Asp Asp Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Val Lys Ser Leu Tyr Trp Ser Tyr Gly Pro Pro Asp Tyr Trp Gly Gln
            100                 105                 110

Gly Thr Thr Val Thr Val Ser Ser
        115                 120
```

<210> SEQ ID NO 85
<211> LENGTH: 120
<212> TYPE: PRT
<213> ORGANISM: Artificial Sequence
<220> FEATURE:
<223> OTHER INFORMATION: Humanized antibody sequence

<400> SEQUENCE: 85

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Ser Val His Trp Val Arg Gln Ala Pro Gly Gln Gly Leu Glu Trp Met
        35                  40                  45

Gly Trp Ile Asn Thr Glu Tyr Asp Phe Thr Ser Tyr Ala Asp Asp Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Val Lys Ser Arg Tyr Trp Ser Tyr Gly Pro Pro Asp Tyr Trp Gly Gln
            100                 105                 110

Gly Thr Thr Val Thr Val Ser Ser
        115                 120
```

<210> SEQ ID NO 86
<211> LENGTH: 120
<212> TYPE: PRT
<213> ORGANISM: Artificial Sequence
<220> FEATURE:
<223> OTHER INFORMATION: Humanized antibody sequence

<400> SEQUENCE: 86

```
Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Asp Phe
            20                  25                  30

Ser Val His Trp Val Arg Gln Ala Pro Gly Gln Gly Leu Glu Trp Met
            35                  40                  45

Gly Trp Ile Asn Thr Glu Thr Asp Glu Thr Ser Tyr Ala Asp Asp Phe
 50                  55                  60

Lys Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
            85                  90                  95

Val Lys Ser Arg Tyr Trp Ser Tyr Gly Pro Pro Asp Tyr Trp Gly Gln
            100                 105                 110

Gly Thr Thr Val Thr Val Ser Ser
            115                 120

<210> SEQ ID NO 87
<211> LENGTH: 446
<212> TYPE: PRT
<213> ORGANISM: Artificial Sequence
<220> FEATURE:
<223> OTHER INFORMATION: Humanized antibody sequence

<400> SEQUENCE: 87

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Phe
            20                  25                  30

Ser Val His Trp Val Arg Gln Ala Pro Gly Gln Gly Leu Glu Trp Met
            35                  40                  45

Gly Trp Ile Asn Thr Glu Thr Asp Glu Thr Ser Tyr Ala Asp Asp Phe
 50                  55                  60

Lys Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
            85                  90                  95

Val Lys Ser Arg Tyr Trp Ser Tyr Gly Pro Pro Asp Tyr Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
 130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
            195                 200                 205

Pro Ser Asn Thr Lys Val Asp Lys Thr Val Glu Arg Lys Cys Cys Val
 210                 215                 220

Glu Cys Pro Pro Cys Pro Ala Pro Val Ala Gly Pro Ser Val Phe
225                 230                 235                 240

Leu Phe Pro Pro Lys Pro Lys Asp Thr Leu Met Ile Ser Arg Thr Pro
            245                 250                 255
```

```
Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 88
<211> LENGTH: 445
<212> TYPE: PRT
<213> ORGANISM: Artificial Sequence
<220> FEATURE:
<223> OTHER INFORMATION: Humanized antibody sequence

<400> SEQUENCE: 88

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Ser Val His Trp Val Arg Gln Ala Pro Gly Gln Gly Leu Glu Trp Met
        35                  40                  45

Gly Trp Ile Asn Thr Glu Thr Asp Glu Thr Ser Tyr Ala Asp Asp Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Val Lys Ser Arg Tyr Trp Ser Tyr Gly Pro Pro Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

```
Leu Gln Ser Ser Gly Leu Tyr Ser Leu Ser Val Val Thr Val Pro
            180                 185                 190

Ser Ser Asn Phe Gly Thr Gln Thr Tyr Thr Cys Asn Val Asp His Lys
                195                 200                 205

Pro Ser Asn Thr Lys Val Asp Lys Thr Val Glu Arg Lys Cys Cys Val
210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Gln Phe Asn Trp Tyr Val Asp Gly Val Glu Val His Asn Ala Lys Thr
                275                 280                 285

Lys Pro Arg Glu Glu Gln Phe Asn Ser Thr Phe Arg Val Val Ser Val
            290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Thr Lys Gly Gln Pro Arg Glu Pro Gln Val Tyr Thr Leu Pro Pro
                340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
                435                 440                 445

<210> SEQ ID NO 89
<211> LENGTH: 214
<212> TYPE: PRT
<213> ORGANISM: Artificial Sequence
<220> FEATURE:
<223> OTHER INFORMATION: Humanized antibody sequence

<400> SEQUENCE: 89

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asn Ile Arg Thr Ala
            20                  25                  30

Val Val Trp Tyr Gln Gln Lys Pro Gly Lys Ala Pro Lys Leu Leu Ile
        35                  40                  45

Tyr Leu Ala Ser Asn Arg His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln His Trp Tyr Pro Phe
                85                  90                  95
```

```
Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 90
<211> LENGTH: 11
<212> TYPE: PRT
<213> ORGANISM: Artificial Sequence
<220> FEATURE:
<223> OTHER INFORMATION: Humanized antibody sequence
<220> FEATURE:
<221> NAME/KEY: VARIANT
<222> LOCATION: (1)..(1)
<223> OTHER INFORMATION: Xaa can be K or R
<220> FEATURE:
<221> NAME/KEY: VARIANT
<222> LOCATION: (6)..(6)
<223> OTHER INFORMATION: Xaa can be V or I
<220> FEATURE:
<221> NAME/KEY: VARIANT
<222> LOCATION: (8)..(8)
<223> OTHER INFORMATION: Xaa can be T or S
<220> FEATURE:
<221> NAME/KEY: VARIANT
<222> LOCATION: (10)..(10)
<223> OTHER INFORMATION: Xaa can be V or L
<220> FEATURE:
<221> NAME/KEY: VARIANT
<222> LOCATION: (11)..(11)
<223> OTHER INFORMATION: Xaa can be V or N

<400> SEQUENCE: 90

Xaa Ala Ser Gln Asn Xaa Arg Xaa Ala Xaa Xaa
1               5                   10
```

```
<210> SEQ ID NO 91
<211> LENGTH: 7
<212> TYPE: PRT
<213> ORGANISM: Artificial Sequence
<220> FEATURE:
<223> OTHER INFORMATION: Humanized antibody sequence
<220> FEATURE:
<221> NAME/KEY: VARIANT
<222> LOCATION: (3)..(3)
<223> OTHER INFORMATION: Xaa can be S or T
<220> FEATURE:
<221> NAME/KEY: VARIANT
<222> LOCATION: (7)..(7)
<223> OTHER INFORMATION: Xaa can be S or G

<400> SEQUENCE: 91

Leu Ala Xaa Asn Arg His Xaa
1               5
```

```
<210> SEQ ID NO 92
<211> LENGTH: 9
<212> TYPE: PRT
<213> ORGANISM: Artificial Sequence
<220> FEATURE:
<223> OTHER INFORMATION: Humanized antibody sequence
<220> FEATURE:
<221> NAME/KEY: VARIANT
<222> LOCATION: (1)..(1)
<223> OTHER INFORMATION: Xaa can be  L or Q
<220> FEATURE:
<221> NAME/KEY: VARIANT
<222> LOCATION: (5)..(5)
<223> OTHER INFORMATION: Xaa can be  T or S
<220> FEATURE:
<221> NAME/KEY: VARIANT
<222> LOCATION: (9)..(9)
<223> OTHER INFORMATION: Xaa can be  T or S

<400> SEQUENCE: 92

Xaa Gln His Trp Xaa Tyr Pro Phe Xaa
1               5

<210> SEQ ID NO 93
<211> LENGTH: 17
<212> TYPE: PRT
<213> ORGANISM: Artificial Sequence
<220> FEATURE:
<223> OTHER INFORMATION: Humanized antibody sequence
<220> FEATURE:
<221> NAME/KEY: VARIANT
<222> LOCATION: (4)..(4)
<223> OTHER INFORMATION: Xaa can be T or S
<220> FEATURE:
<221> NAME/KEY: VARIANT
<222> LOCATION: (6)..(6)
<223> OTHER INFORMATION: Xaa can be T or S
<220> FEATURE:
<221> NAME/KEY: VARIANT
<222> LOCATION: (9)..(9)
<223> OTHER INFORMATION: Xaa can be T or S
<220> FEATURE:
<221> NAME/KEY: VARIANT
<222> LOCATION: (10)..(10)
<223> OTHER INFORMATION: Xaa can be S or T
<220> FEATURE:
<221> NAME/KEY: VARIANT
<222> LOCATION: (13)..(13)
<223> OTHER INFORMATION: Xaa can be D or Q
<220> FEATURE:
<221> NAME/KEY: VARIANT
<222> LOCATION: (14)..(14)
<223> OTHER INFORMATION: Xaa can be D or N
<220> FEATURE:
<221> NAME/KEY: VARIANT
<222> LOCATION: (16)..(16)
<223> OTHER INFORMATION: Xaa can be K or Q

<400> SEQUENCE: 93

Trp Ile Asn Xaa Glu Xaa Asp Glu Xaa Xaa Tyr Ala Xaa Xaa Phe Xaa
1               5                   10                  15

Gly

<210> SEQ ID NO 94
<211> LENGTH: 11
<212> TYPE: PRT
<213> ORGANISM: Artificial Sequence
<220> FEATURE:
<223> OTHER INFORMATION: Humanized antibody sequence
<220> FEATURE:
<221> NAME/KEY: VARIANT
<222> LOCATION: (5)..(5)
<223> OTHER INFORMATION: Xaa can be T or S
```

```
<220> FEATURE:
<221> NAME/KEY: VARIANT
<222> LOCATION: (11)..(11)
<223> OTHER INFORMATION: Xaa can be Y or V

<400> SEQUENCE: 94

Ser Arg Gly Trp Xaa Tyr Gly Pro Pro Asp Xaa
1               5                   10
```